(12) United States Patent
Kondo et al.

(10) Patent No.: US 6,231,934 B1
(45) Date of Patent: *May 15, 2001

(54) ALKENYL COMPOUND, LIQUID CRYSTAL COMPOSITION, AND LIQUID CRYSTAL DISPLAY DEVICE

(75) Inventors: Tomoyuki Kondo; Shuichi Matsui; Kazutoshi Miyazawa; Yasuko Sekiguchi; Etsuo Nakagawa, all of Chiba (JP)

(73) Assignee: Chisso Corporation, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/155,348
(22) PCT Filed: Mar. 27, 1997
(86) PCT No.: PCT/JP97/01047
§ 371 Date: Sep. 28, 1998
§ 102(e) Date: Sep. 28, 1998
(87) PCT Pub. No.: WO97/35822
PCT Pub. Date: Feb. 10, 1997

(30) Foreign Application Priority Data

Mar. 28, 1996 (JP) .................................................. 8-099251

(51) Int. Cl.⁷ .......................... C09K 19/34; C09K 19/30; C07D 239/02; C07D 319/06; C07C 25/13
(52) U.S. Cl. ............... 428/1.1; 252/299.61; 252/299.63; 252/299.66; 544/242; 546/350; 549/369; 570/128; 570/129; 570/130; 570/131
(58) Field of Search .......... 252/299.01, 299.61, 252/299.63, 299.66; 428/1.1; 544/242, 336; 546/350; 549/369; 570/128, 129, 130, 311

(56) References Cited

U.S. PATENT DOCUMENTS 5,776,367 * 7/1998 Matsui et al. ................... 252/299.63
6,001,275 * 12/1999 Onishi et al. ................... 252/299.01

FOREIGN PATENT DOCUMENTS

| | | |
|---|---|---|
| 4441963 | 11/1995 | (DE) . |
| 19505189 | 6/1996 | (DE) . |
| 0064193 | 11/1982 | (EP) . |
| 0750028 | 12/1996 | (EP) . |
| 0805134 | 11/1997 | (EP) . |
| 5-9297 * | 1/1993 | (JP) . |
| 8-325173 * | 12/1996 | (JP) . |
| WO 95/30723 | 11/1995 | (WO) . |
| 96/22261 | 7/1996 | (WO) . |
| 96/37451 | 11/1996 | (WO) . |

OTHER PUBLICATIONS

Harold et al., "Coupling of Terminal Olefins by Molybdenum(VI) Imido ALkylidene Complexes", Organometallics, 13(2), pp. 635–639, 1994.*

* cited by examiner

Primary Examiner—Shean C. Wu
(74) Attorney, Agent, or Firm—Wenderoth, Lind & Ponack, L.L.P.

(57) ABSTRACT

The liquid crystalline compound is expressed by the general formula (1)

$$Ra\text{-}A_1\text{-}Z_1\text{-}A_2\text{-}Z_2\text{-}A_3\text{-}Z_3\text{-}A_4\text{-}Rb \qquad (1)$$

wherein Ra represents an alkenyl group having 2 to 20 carbon atoms or an alkyl group having 1 to 20 carbon atoms any methylene group ($-CH_2-$) in the alkenylene or alkyl group may be replaced by $-O-$, $-S-$, $-CO-$, $-CH=CH-$, or $-C\equiv C-$, but in no case $-O-$ and/or $-S-$ continues, and any hydrogen atom in Ra may be replaced by a halogen atom; Rb represents Ra, a halogen atom, or cyano group provided that at least one of Ra and Rb represents a group having double bond; $A_1$, $A_2$, $A_3$, and $A_4$ independently represent trans-1,4-cyclohexylene group, 1,4-phenylene group any hydrogen atom on the ring may be replaced by fluorine atom or cyano group, cyclohexenediyl group, pyridine-2,5-diyl group, pyrimidine-2,5-diyl group, or 1,3-dioxane-2,5-diyl group; and $Z_1$, $Z_2$, and $Z_3$ independently represent an alkenylene group having 2 to 4 carbon atoms, $-(CH_2)_2-$, $-COO-$, $-OCO-$, $-C\equiv C-$, $-CH_2O-$, $-OCH_2-$, or single bond any hydrogen atom in the groups may be replaced by a halogen atom provided that at least one of $Z_1$, $Z_2$, and $Z_3$ represents an alkenylene group having 2 to 4 carbon atoms.

16 Claims, No Drawings

ALKENYL COMPOUND, LIQUID CRYSTAL COMPOSITION, AND LIQUID CRYSTAL DISPLAY DEVICE

This application is a 371 of PCT/JP97/01047, filed Mar. 27, 1997.

The present invention relates to liquid crystalline compounds and liquid crystal compositions. More specifically, it relates to liquid crystalline compounds having one or more double bonds simultaneously in each of a terminal group and a bonding group; liquid crystal compositions comprising the liquid crystalline compound; and liquid crystal display devices comprising the liquid crystal composition.

BACKGROUND ART

In the present specification and claims, the term "liquid crystalline compound" is used as general name for the compounds which exhibit liquid crystal phase and the compounds which do not exhibit liquid crystal phase but are used as component of liquid crystal compositions.

Liquid crystal display devices utilizing liquid crystalline compounds are widely used in such displays as watches, tabletop calculators, and word processors. These liquid crystal display devices utilize the optical anisotropy and dielectric anisotropy of liquid crystalline compounds.

Liquid crystal phase includes nematic phase, smectic phase, and cholesteric phase. Among them, nematic liquid crystal phase is most widely employed for display devices. On the other hand, there have been developed many display modes such as dynamic scattering (DS) mode, deformation of aligned phases (DAP) mode, guest/host (GH) mode, twist nematic (TN) mode, super twist nematic (STN) mode, and thin film transistor (TFT).

Liquid crystalline compounds used in these display modes are required to exhibit a wide temperature range of liquid crystal phase with room temperature being its center, to be sufficiently stable under conditions in which display devices are used, and to have characteristics sufficient to drive display devices. However, no liquid crystalline compounds which satisfy such requirements by a single compound have been found up to now. Accordingly, it is an actual circumstance that several kind or several tens kind of liquid crystalline compounds are mixed to produce liquid crystal compositions having required characteristics. These liquid crystal compositions are required to be stable against moisture, light, heat, and air which usually exist under the conditions in which display devices are used, to be stable against electric field and electromagnetic radiation, and further to be chemically stable against compounds to be mixed. Liquid crystal compositions are required to have a proper optical anisotropy ($\Delta n$) and dielectric anisotropy ($\Delta \epsilon$) depending on the display mode and the shape of display devices. Further, it is important that each component in the liquid crystal compositions has an excellent miscibility with one another.

In recent years, demand for the compounds exhibiting liquid crystal phase at a wider temperature range, particularly for the compounds exhibiting a high transition temperature to isotropic phase is elevated in keeping with diversification of environments in which liquid crystal display devices are used. Besides, in order to expand the size of screen and improve the quality of display, it is preferable that the compounds have a low viscosity. As such compounds, ones expressed by the formula (a), (b), or (c) are disclosed in Japanese Patent Publication No. Sho 62-46527, Japanese patent Publication no. Hei 4-28693, or Japanese Patent Publication No Hei 2-1811, respectively. Also, a compound having an alkenylene group as bonding group and expressed by the formula (d) is known (24th FREIBURGER ARBEITSTAGUNG FLUSSIGKRISTALLE P01 (1995)).

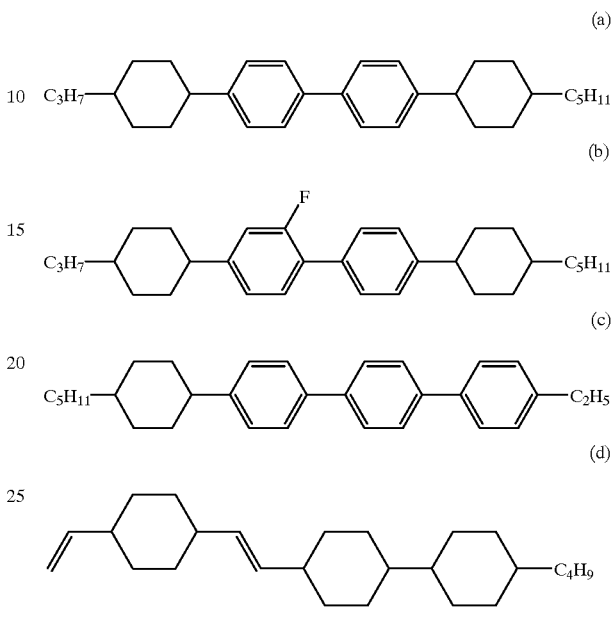

Whereas the compounds of the formula (a) or (b) have a comparatively high transition temperature to isotropic phase, their viscosity can not be said to be sufficiently low. Compound of the formula (c) has a strong smectic property and the miscibility with other liquid crystal materials is poor. Compound of the formula (d) has a problem that the transition temperature to isotropic phase is low.

Therefore, development of liquid crystalline compounds having a wider temperature range of liquid crystal phase, low viscosity, and excellent miscibility with other liquid crystal materials are long-awaited.

DISCLOSURE OF THE INVENTION

An object of the present invention is to solve the defects in the prior art described above. Another object of the present invention is to provide liquid crystalline compounds having a wide temperature range of liquid crystal phase, low viscosity, excellent chemical stability, and superior miscibility with other liquid crystal materials; liquid crystal compositions comprising the liquid crystalline compound; and liquid crystal display devices utilizing the liquid crystal compositions therein.

In order to attain the objects of the present invention described above, the present invention is summarized as follows:

(1) A liquid crystalline compound expressed by the general formula (1)

$$Ra\text{-}A_1\text{-}Z_1\text{-}A_2\text{-}Z_2\text{-}A_3\text{-}Z_3\text{-}A_4\text{-}Rb \tag{1}$$

wherein Ra represents an alkenyl group having 2 to 20 carbon atoms or an alkyl group having 1 to 20 carbon atoms any methylene group (—CH$_2$—) in the alkenyl or alkyl group may be replaced by —O—, —S—, —CO—, —CH=CH—, or —C≡C—, but in no case —O— and/or —S— continues, and any hydrogen atom in Ra may be replaced by a halogen atom; Rb represents Ra, a halogen atom, or cyano group provided that at least one of Ra and Rb represents a group having double bond; $A_1$, $A_2$, $A_3$, and $A_4$ independently represent trans-1,4-cyclohexylene group, 1,4-phenylene group any hydrogen atom on the ring may be replaced by fluorine atom or cyano group, cyclohexenediyl group, pyridine-2,5-diyl group, pyrimidine-2,5-diyl group, or 1,3-dioxane-2,5-diyl group; and $Z_1$, $Z_2$, and $Z_3$ independently represent an alkenylene group having 2 to 4 carbon atoms, —$(CH_2)_2$—, —COO—, —OCO—, —C≡C—, —$CH_2$O—, —$OCH_2$—, or single bond any hydrogen atom in the groups may be replaced by a halogen atom provided that at least one of $Z_1$, $Z_2$, and $Z_3$ represents an alkenylene group having 2 to 4 carbon atoms.

(2) The liquid crystalline compound recited in paragraph (1) above wherein Ra in an alkenyl group.

(3) The liquid crystalline compound recited in paragraph (2) above wherein $Z_1$ is an alkenylene group having 2 to 4 carbon atoms.

(4) The liquid crystalline compound recited in paragraph (2) above wherein $Z_2$ is an alkenylene group having 2 to 4 carbon atoms.

(5) The liquid crystalline compound recited in paragraph (2) above wherein $Z_3$ is an alkenylene group having 2 to 4 carbon atoms.

(6) The liquid crystalline compound recited in paragraph (3) above wherein $A_1$, $A_2$, $A_3$, and $A_4$ are independently trans-1,4-cyclohexylene group, or 1,4-phenylene group any hydrogen atom on the ring may be replaced by fluorine atom or cyano group.

(7) The liquid crystalline compound recited in paragraph (4) above wherein $A_1$, $A_2$, $A_3$, and $A_4$ are independently trans-1,4-cyclohexylene group, 1,4-phenylene group any hydrogen atom on the ring may be replaced by fluorine atom or cyano group.

(8) The liquid crystalline compound recited in paragraph (5) above wherein $A_1$, $A_2$, $A_3$, and $A_4$ are independently trans-1,4-cyclohexylene group, 1,4-phenylene group any hydrogen atom on the ring may be replaced by fluorine atom or cyano group.

(9) A liquid crystal compositions comprising at least one liquid crystalline compound recited in any one of paragraphs (1) to (8) above.

(10) A liquid crystal compositions comprising, as a first component, at least one liquid crystalline compound recited in any one of paragraphs (1) to (8) above, and comprising, as a second component, at least one compound selected from the group consisting of the compounds expressed by any one of the general formulas (2), (3), and (4)

(2)

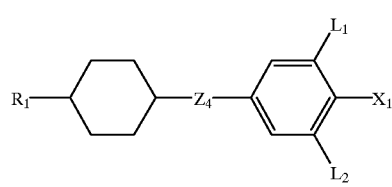

(3)

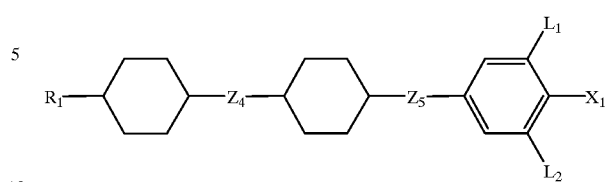

(4)

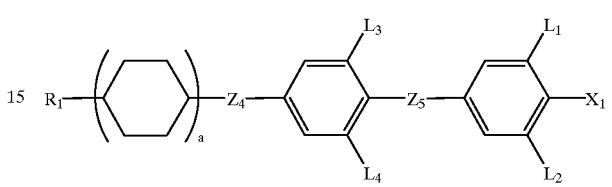

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$, and $L_4$ independently represent H or F; $Z_4$ and $Z_5$ independently represent —$(CH_2)_2$—, —CH=CH—, or a single bond; and a is 1 or 2.

(11) A liquid crystal composition comprising, as a first component, at least one liquid crystalline compound recited in any one of paragraphs (1) to (8) above, and comprising, as a second component, as least one compound selected from the group consisting of the compounds expressed by any one of the general formulas (5), (6), (7), (8), and (9), (5)

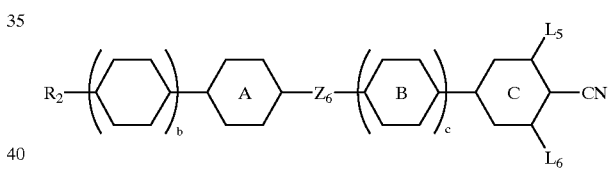

wherein $R_2$ represents F, an alkyl group having 1 to 10 carbon atoms, or an alkenyl group having 2 to 10 carbon atoms any methylene group (—$CH_2$—) in the groups may be replaced by oxygen atom, but in no case two or more methylene groups are continuously replaced by oxygen atom; ring A represents trans-1,4-cyclohexylene group, 1,4-phenylene group, or 1,3-dioxane-2,5-phenylene group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —$(CH_2)_2$—, —COO—, or single bond; $L_5$ and $L_6$ independently represent H or F; and b and c are independently or 1, (6)

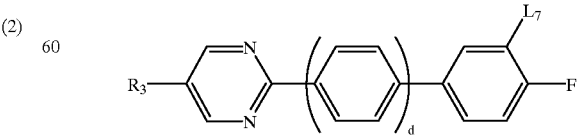

wherein $R_3$ represents an alkyl group having 1 to 10 carbon atom; $L_7$ represents H or F; and d is 0 or 1, (7)

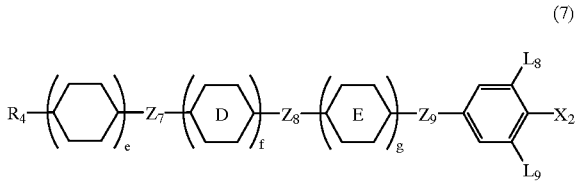

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or single bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$; and e, f, and g are independently 0 or 1, (8)

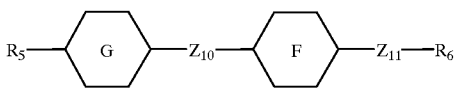

wherein $R_5$ and $R_6$ independently represent an alkyl group having 1 to 10 carbon atoms or an alkenyl group having 2 to 10 carbon atoms any methylene group (—$CH_2$—) in the alkyl or alkenyl group may be replaced by oxygen atom (—O—), but in no case two or more methylene groups are continuously replaced by oxygen atom; ring G represents trans-1,4-cyclohexylene group, 1,4-phenylene group, or pyrimidine-2,5-diyl group; ring F represents trans-1,4-cyclohexylene group or 1,4-phenylene group; $Z_{10}$ represents —C≡C—, —COO—, —($CH_2$)$_2$—, —CH=CH—C≡C—, or single bond; and $Z_{11}$ represents —COO— or single bond, (9)

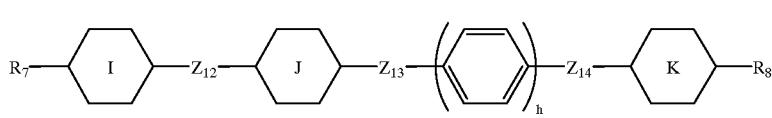

wherein $R_7$ and $R_8$ independently represent an alkyl group having 1 to 10 carbon atoms or an alkenyl group having 2 to 10 carbon atoms any methylene group (—$CH_2$—) in the alkyl or alkenyl group may be replaced by oxygen atom (—O—), but in no case two or more methylene groups are continuously replaced by oxygen atom; ring I represents trans-1,4-cyclohexylene group, 1,4-phenylene group, or pyrimidine-2,5diyl group; ring J represents trans-1,4-cyclohexylene group, 1,4-phenylene group any hydrogen atom on the ring may be replaced by F, or pyrimidine-2,5-diyl group; ring K represents trans-1,4-cyclohexylene group or 1,4-phenylene group; $Z_{12}$ and $Z_{14}$ independently represent —COO—, —($CH_2$)$_2$—, or single bond; $Z_{13}$ represents —CH=CH—, —C≡C—, —COO—, or single bond; and h is 0 or 1.

(12) A liquid crystal composition comprising, as a first component, at least one liquid crystalline compound recited in any one of paragraphs (1) to (8) above, comprising, as a part of a second component, at least one compound selected from the group consisting of the compounds expressed by any one of the general formulas (2), (3), and (4) recited in paragraph (10) above, and comprising, as another part of the second component, at least one compound selected from the group consisting of the compounds expressed by any one of the general formulas (5), (6), (7), (8), and (9) recited in paragraph (11) above.

(13) A liquid crystal display device utilizing a liquid crystal composition recited in any one of paragraphs (9) to (12) above.

Liquid crystalline compounds of the present invention expressed by the general formula (1) have a wide temperature range of liquid crystal phase, low viscosity, and excellent miscibility with other liquid crystal materials. These liquid crystalline compounds are sufficiently stable chemically and physically under the conditions in which display devices are ordinarily used. Further, compounds having desired physical properties can be produced by selecting proper six-membered rings, substituents and/or bonding groups as molecule constituting element. Accordingly, when the compounds of the present invention are used as component of liquid crystal compositions, novel liquid crystal compositions having preferable characteristics can be provided.

Compounds of the present invention are expressed by the following general formula (1):

$$Ra-A_1-Z_1-A_2-Z_2-A_3-Z_3-A_4-Rb \qquad (1)$$

In the general formula (1), Ra is a straight chain or branched alkenyl group having 2 to 20 carbon atoms or an alkyl group having 1 to 20 carbon atoms. Specifically, a straight chain alkenyl group such as vinyl, propenyl, butenyl, pentenyl, hexenyl, decenyl, and icosenyl; a branched alkenyl group such as isopropenyl, isopentenyl, isoheptenyl, 3-ethyloctenyl, 3,5-dimethyltetra-decenyl, and 5-ethyl-5-methylnonadecenyl; a straight chain alkyl group such as methyl, ethyl, propyl, butyl, pentyl, hexyl, heptyl, decyl, pentadecyl, and icosyl; and a branched alkyl group such as isopropyl, sec-butyl, tert-butyl, 2-methylbutyl, isopentyl, isohexyl, 3-ethyloctyl, 3,8-dimethyltetradecyl, and 5-ethyl-5-methylnonadecyl can be mentioned as examples. The alkenyl group and alkyl group described above may be ones which exhibit an optical activity.

Any methylene group (—$CH_2$—) in these alkenyl or alkyl grouops may be replaced by —O—, —S—, —CO—, —CH=CH—, or —C≡C—, unless —O— and/or —S— continues. As examples in which methylene group is replaced by —O—, an alkenyloxy group, alkoxyalkenyl group, alkoxy group, and alkoxyalkyl group can be mentioned; as examples in which methylene group is replaced by —S—, an alkylthioalkyl group; as examples in which methylene group is replaced by —CH=CH—, an alkadienyl group; as examples in which mthylene group is replaced by —C≡C—, an alkynyl group, alkynyloxy group, and alkoxyalkynyl group can be mentioned, respectively. Any hydrogen atom in the alkenyl group or alkyl group may be replaced by a halogen atom, and as such examples, a halogen substituted alkenyl group, halogen substituted alkyl group, halogen substituted alkenyloxy group, halogen substituted alkoxy group, halogen substituted alkoxyalkenyl group, halogen substituted alkoxyalkyl group, and halogen substituted alkynyl group can be mentioned.

These groups can be mentioned more specifically as follows:

As the groups in which —$CH_2$— is replaced by —O—, alkoxyalkenyl groups such as methoxypropenyl, ethoxypropenyl, pentyloxypropenyl, methoxybutenyl, ethoxybutenyl, pentyloxybutenyl, methoxypentenyl, propoxypentenyl, methoxyhexenyl, propoxyhexenyl, methoxyheptenyl, and methoxyoctenyl, alkenyloxy groups such as propenyloxy, butenyloxy, pentenylosxy, octenyloxy, and propenyloxymethyl, alkoxyalkenyl groups such as propenyloxyethyl, propenyloxybutyl, butenyloxymethyl, butenyloxyethyl, butenyloxypentyl, pentenyloxymethyl, pentenyloxypropyl, hexenyloxymethyl, hexenyloxyethyl, heptenyloxymethyl, and octenyloxymethyl, alkoxy groups such as methoxy, ethoxy, propoxy, butoxy, pentyloxy, and nonyloxy, and alkoxyalkyl groups such as methoxymethyl, methoxyethyl, methoxypropyl, methosybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, heyxloxypropyl, heptyloxymethyl, and octyloxymethyl.

Further, the followings can be mentioned:

Alkadienyl groups such as butadienyl, pentadienyl, hexadienyl, heptadienyl, octadienyl, and icosadienyl, halogen substituted alkenyl groups such as 3-fluoropropenyl, 4-fluoro-1-butenyl, 4-fluoro-2-butenyl, 5-fluoro-1-pentenyl, 5-fluoro-2-pentenyl, 5-fluoro-3-pentenyl, 6-fluoro-1-hexenyl, 6-fluoro-3-hexenyl, 7-fluoro-5-heptenyl, 2,2-difluorovinyl, 1,2-difluorovinyl, 2-chloro-2-fluorovinyl, 2-bromo-2-fluorovinyl, 2-fluoro-2-cyanovinyl, 3,3-difluoro-2-propenyl, 3-chloro-3-fluoro-1 propenyl, 2,3-diflluoro-1-propenyl, 1,3-difluoro-2-propenyl, 1,3,3-trifluoro-2-propenyl, 1,2,4,4-tetrafluoro-3-butenyl, 5,5-difluoro-4-pentenyl, 3,3-difluoro-5-hexenyl, and 8,8difluoro-7octenyl, halogen substituted alkyl groups such as fluoromethyl difluoromethyl, trifluoromethyl, 2-fluoroethyl, 1,2-difluoroethyl, 1,1,2,2-tetrafluoroethyl, 2-bromo-1,2-difluoroethyl, 3-fluoropropyl, 1,2,3,3-tetrafluoropropyl, 1,1,2,3,3,3-hexafluoropropyl, 4-fluorobutyl, 1,1,2,4-tetrafluorobutyl, 5-fluoropentyl, 2,3,3,4,5-pentafluoropentyl, 6-fluorohexyl, 2,3,4,6-tetrafluorohexyl, 7-fluoroheptyl, and 8,8-difluorooctyl, halogen substituted alkoxy groups such as difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 1,1,2,3,3,3-hexafluoropropoxy, and perfluoropropoxy, alkylthioalkyl groups such as methylthiomethyl, methylthioethyl, methylthiopropyl, methylthiobutyl, methylthiooctyl, ethylthiomethyl, ethylthioethyl, ethylthioheptyl, propylthiomethyl, propylthioethyl, propylthiopropyl, porpylthiopentyl, hexylthiomethyl, and heptylthioethyl, groups such as methycarbonyl, ethylcarbonyl, propycarbonyl, methoxycarbonyl, ethoxycarbonyl, propoxycarbonyl, butoxycarbonyl, heptyloxycarbonyl, 2-oxopropyl, 2-oxobutyl, 3-oxobutyl, 2-oxopentyl, 4-oxopentyl, 3-oxohexyl, 5-oxohexyl, 2-oxoheptyl, 3-oxoheptyl, 6-oxoheptyl, 2-oxooctyl, 4-oxooctyl, 7-oxoctyl, 3-oxononyl, 6-oxononyl, 8-oxononyl, 2-oxodecyl, 5-oxodecyl, and 9-oxodecyl, alkynyl groups such as ethynyl, propynyl, butynyl, pentynyl, and octynyl, alkynyloxy groups such as ethynyloxy, propynyloxy, butynyloxy, pentynyloxy, and tetradecynyloxy, and alkoxyalkynyl groups such as methoxypropynyl, methoxypentynyl, ethoxybutynyl, propoxypropynyl, hexyloxyheptynyl, methoxymethylbutynyl, methoxypropylethynyl, and butoxymethylpropynyl.

In the general formula (1), while Rb is an atom or group selected from the Ra described above, a halogen atom including F, Cl, Br, and I, and cyano group, Rb is preferably an atom or group other than Br and I from the viewpoints of chemical stability of the liquid crystalline compounds to be obtained and other factors.

In the general formula (1), $A_1$, $A_2$, $A_3$, and $A_4$ independently represent trans-1,4-cyclohexylene group, 1,4-phenylene group any hydrogen atom on the ring may be replaced by fluorine atom or cyano group, cyclohexenediyl group, pyridine-2,5-diyl group, pyrimidine-2,5-diyl group, or 1,3-dioxane-2,5-diyl group.

As examples of the group in which hydrogen atom on the ring is replaced by a halogen atom or cyano group, 2-fluoro-1,4-phenylene, 3-fluoro-1,4-phenylene, 2,3-difluoro-1,4-phenylene, 3,5-difluoro-1,4-phenylene, 2,3,5-trifluoro-1,4-phenylene, 2-chloro-1,4-phenylene, 3-chloro-1,4-phenylene, 2,3-dichloro-1,4-phenylene, 3,5-dichloro-1,4-phenylene, 3-bromo-1,4-phenylene, 2-iodo-1,4-phenylene, 2-chloro-3-fluoro-1,4-phenylene, 3-fluoro-5-chloro-1,4-phenylene, 2-cyano-1,4-phenylene, 3-cyano-1,4-phenylene, and 2,3-dicyano-1,4-phenylene can be mentioned.

In the general formula (1), $Z_1$, $Z_2$, and $Z_3$ independently represent an alkenylene group having 2 to 4 carbon atoms, —$(CH_2)_2$—, —COO—, —OCO—, —C≡C—, —$CH_2O$—, —$OCH_2$—, or single bond, and at least one of $Z_1$, $Z_2$, and $Z_3$ is an alkenyl group. Preferable alkenylene group is vinylene or butenylene, and a more preferable one is a trans-alkenylene group.

One or more hydrogen atoms in $Z_1$, $Z_2$, and $Z_3$ may be replaced by a halogen atom. As their examples, fluoromethyleneoxy, oxyfluoromethylene, difluoromethyleneoxy, oxydifluoromethylene, 2,2-difluoroethylene, 1,2-difluorovinylene, 1-fluorovinylene, 1-bromo-2-fluorovinylene, and 1-chloro-2-fluorovinylene can be mentioned.

While any compounds of the present invention constituted by the groups selected from each of the Ra, Rb, $A_1$ to $A_4$, and $Z_1$ to $Z_3$ described above and expressed by the general formula (1) has preferable characteristics, the compounds expressed by one of the formulas (1a) to (1v) can be mentioned as examples of more preferable compounds.

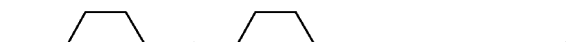

(1-a)

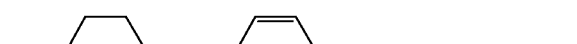

(1-b)

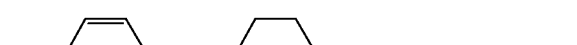

(1-c)

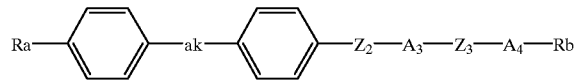
(1-d)

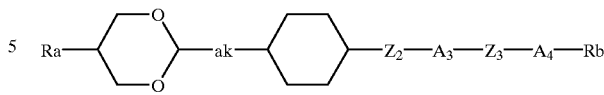
(1-n)

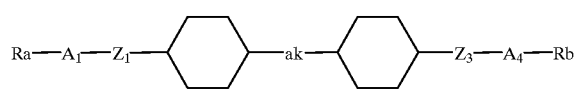
(1-e)

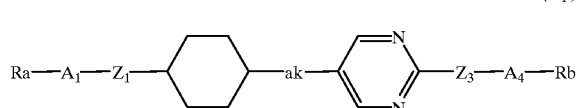
(1-o)

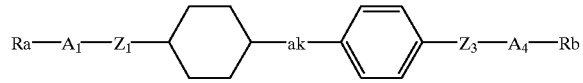
(1-f)

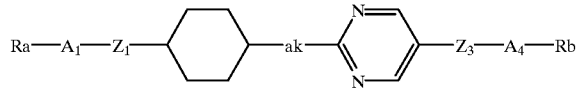
(1-p)

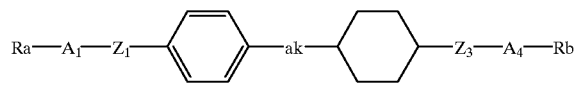
(1-g)

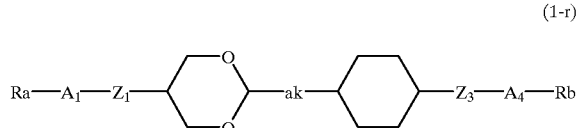
(1-q)

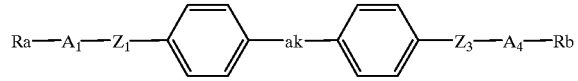
(1-h)

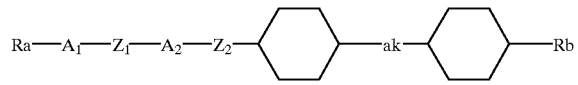
(1-i)

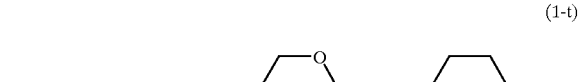
(1-r)

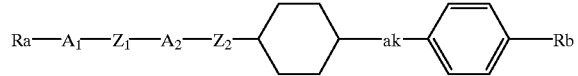
(1-j)

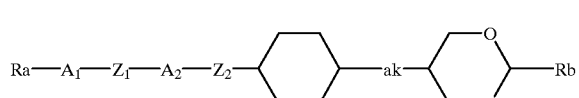
(1-s)

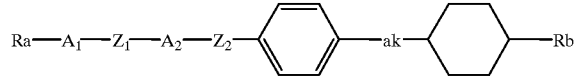
(1-k)

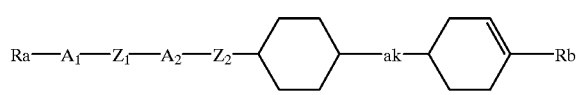
(1-t)

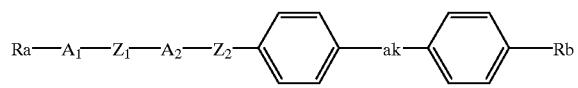
(1-l)

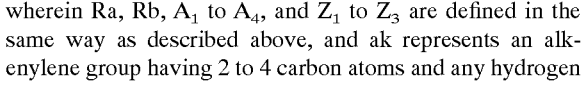
(1-u)

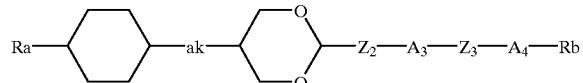
(1-m)

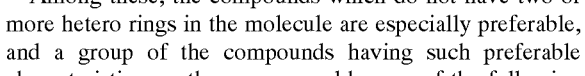
(1-v)

wherein Ra, Rb, $A_1$ to $A_4$, and $Z_1$ to $Z_3$ are defined in the same way as described above, and ak represents an alkenylene group having 2 to 4 carbon atoms and any hydrogen atom on the ring may be replaced by a halogen atom or cyano group.

Among these, the compounds which do not have two or more hetero rings in the molecule are especially preferable, and a group of the compounds having such preferable characteristics are those expressed by one of the following formulas (1—1) to (1-77).

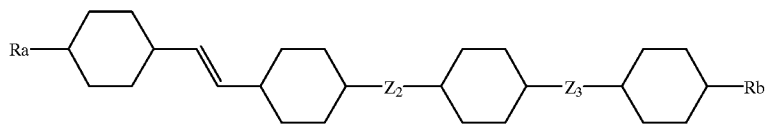
(1-1)
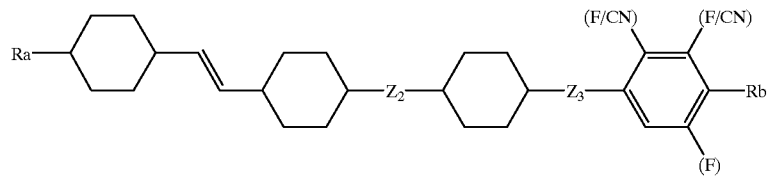
(1-2)
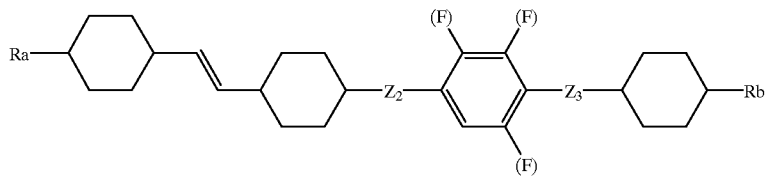
(1-3)
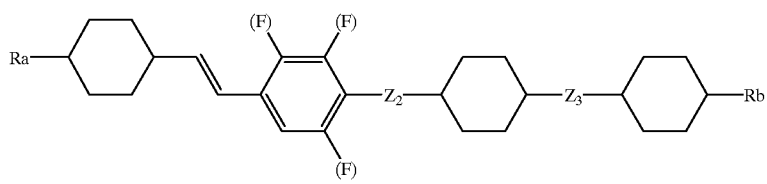
(1-4)
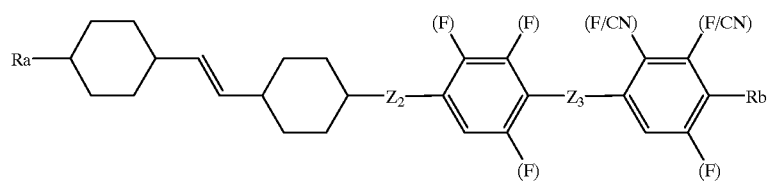
(1-5)
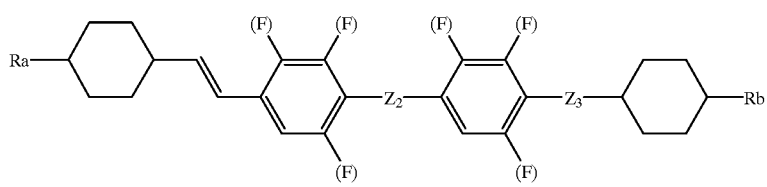
(1-6)
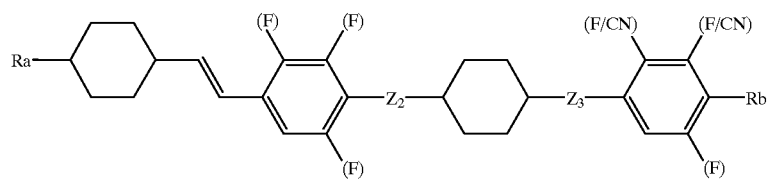
(1-7)
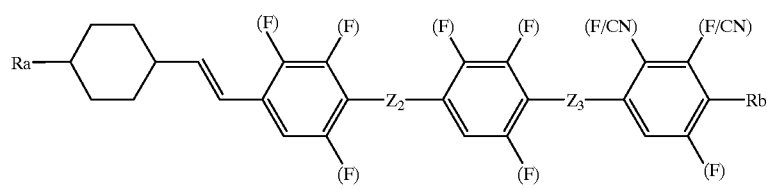
(1-8)

(1-9)
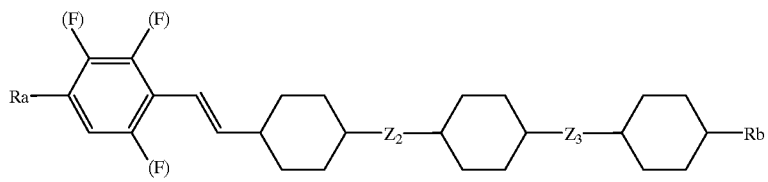
(1-10)
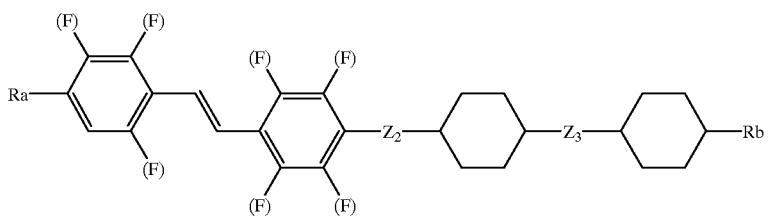
(1-11)
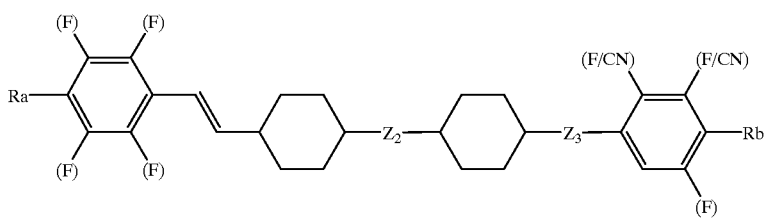
(1-12)
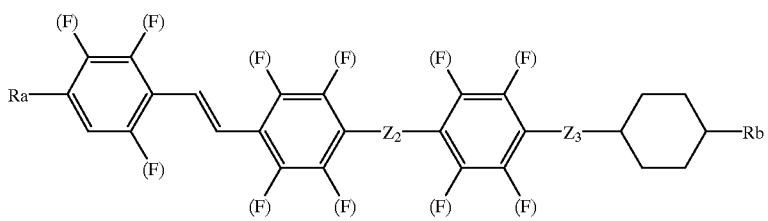
(1-13)
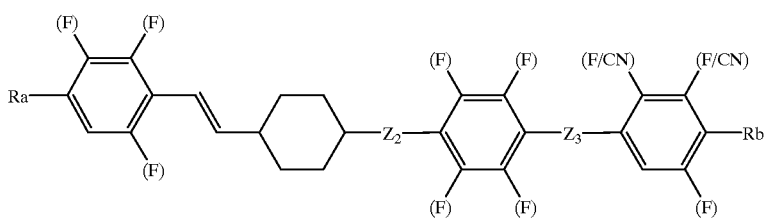
(1-14)
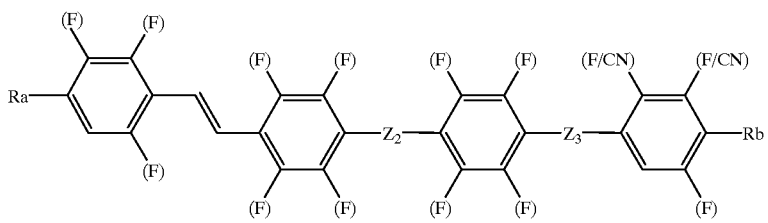
(1-15)
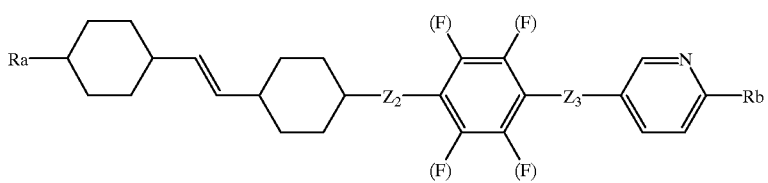

-continued
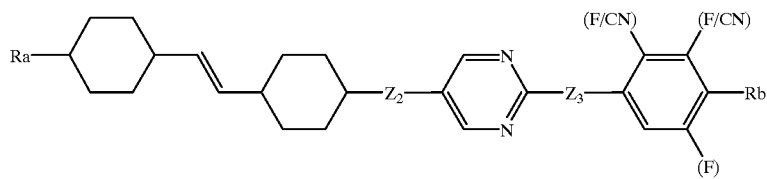
(1-16)
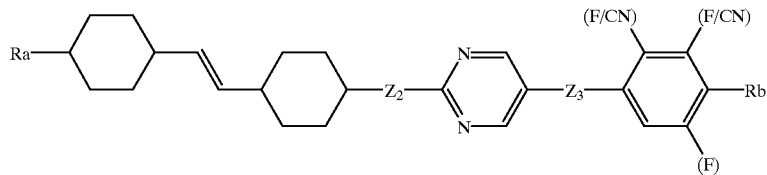
(1-17)
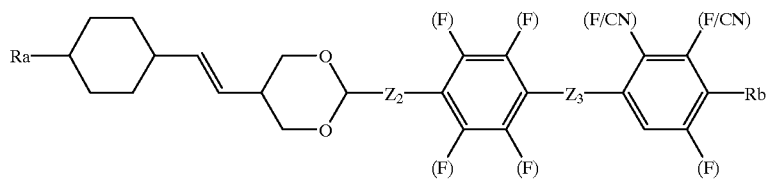
(1-18)
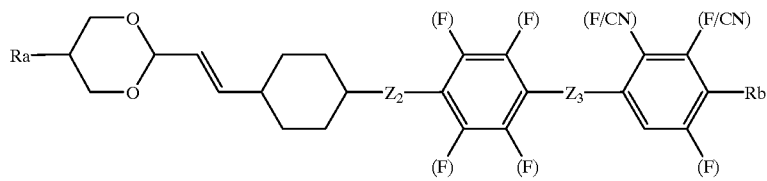
(1-19)
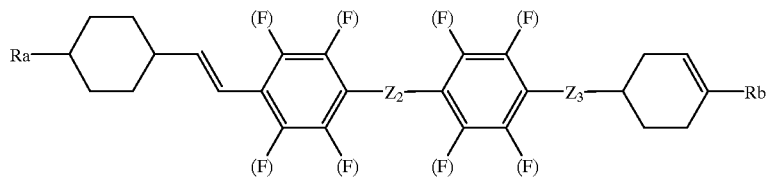
(1-20)
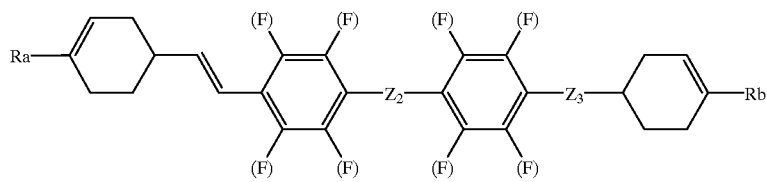
(1-21)
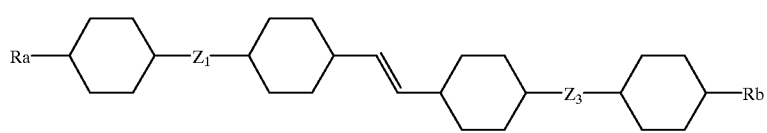
(1-22)
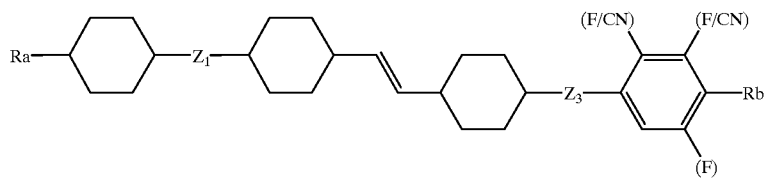
(1-23)

-continued
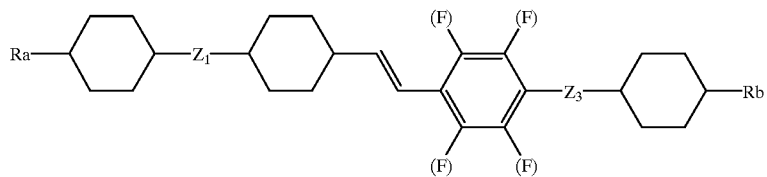
(1-24)
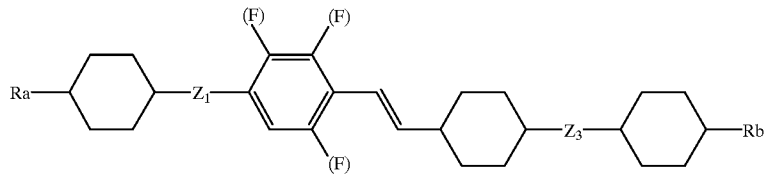
(1-25)
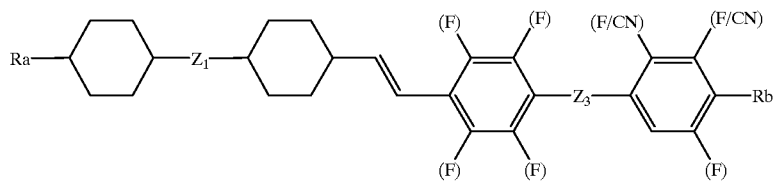
(1-26)
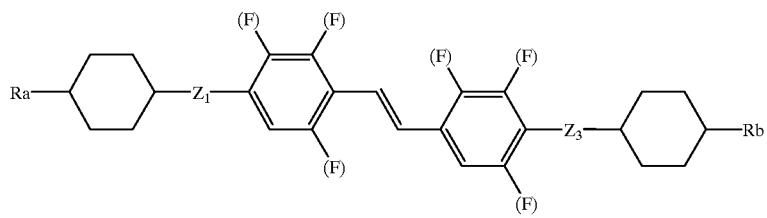
(1-27)
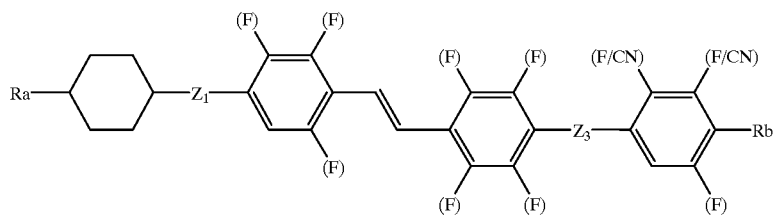
(1-28)
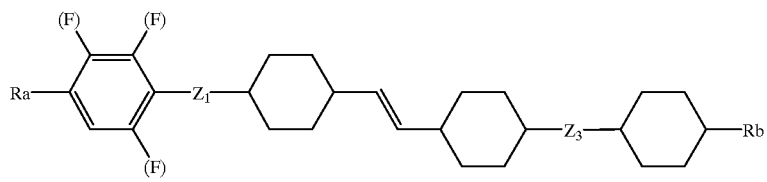
(1-29)
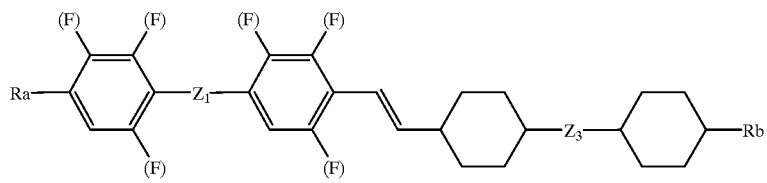
(1-30)

-continued
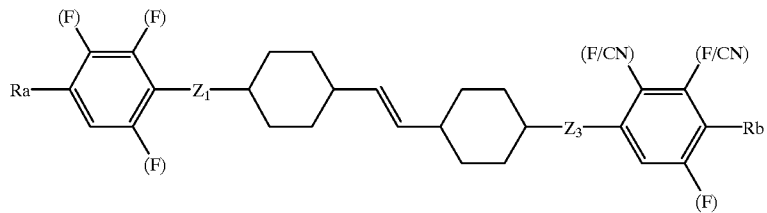
(1-31)
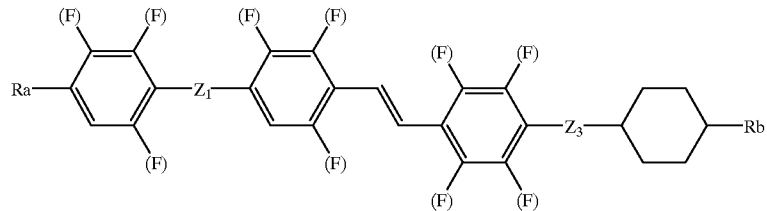
(1-32)
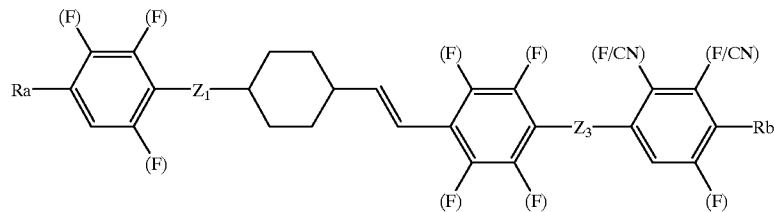
(1-33)
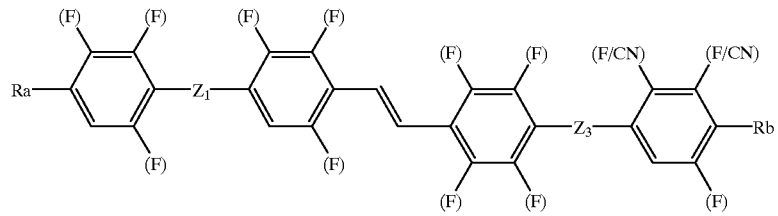
(1-34)
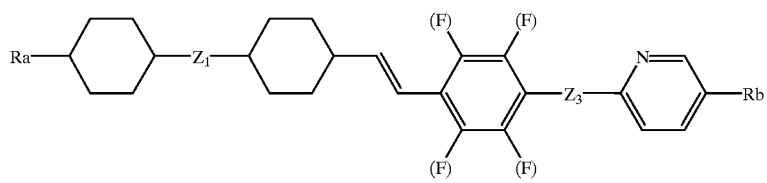
(1-35)
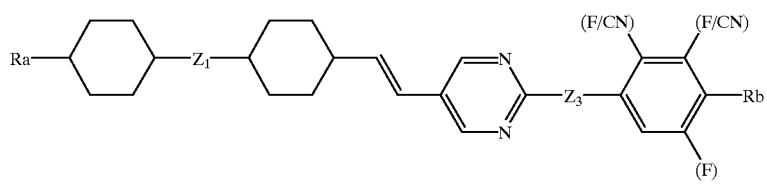
(1-36)
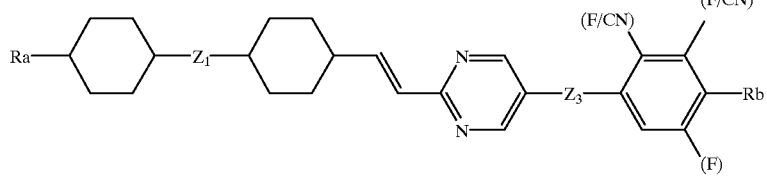
(1-37)

(1-38)
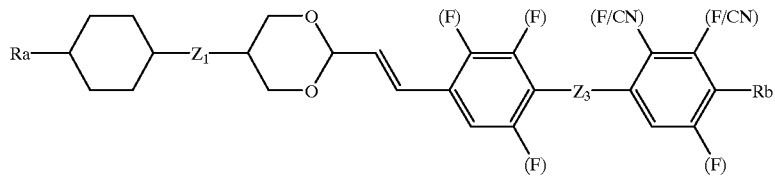
(1-39)
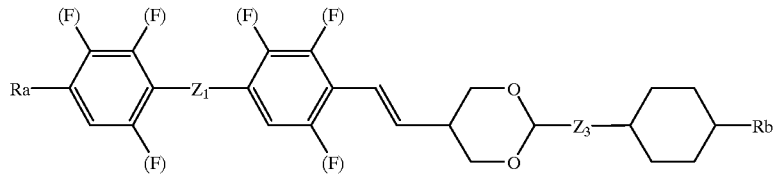
(1-40)
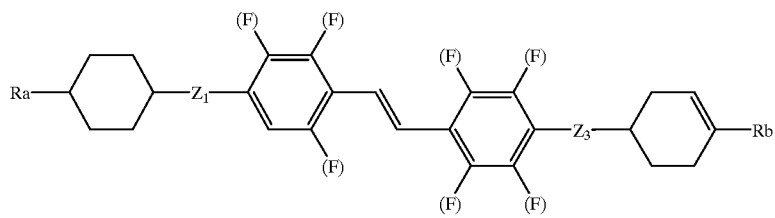
(1-41)
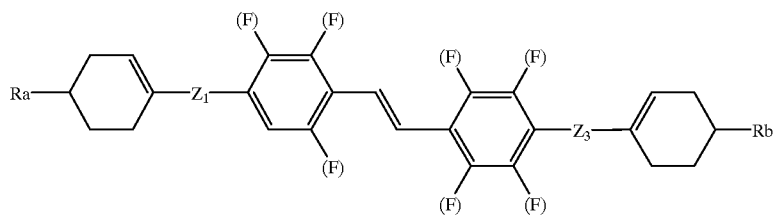
(1-42)
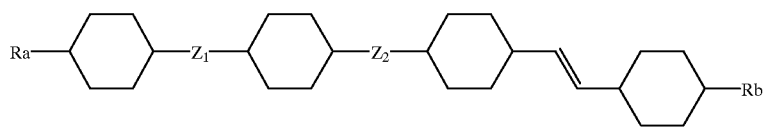
(1-43)
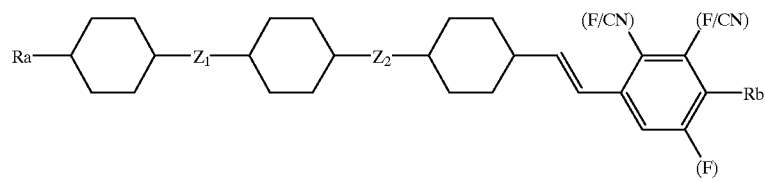
(1-44)
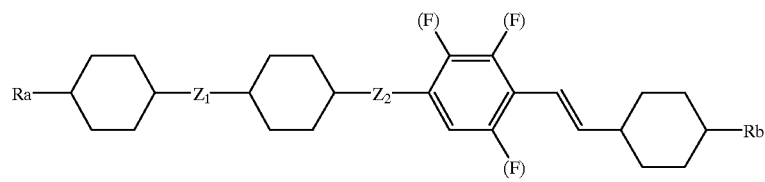
(1-45)
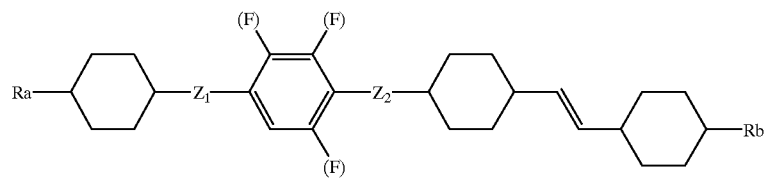

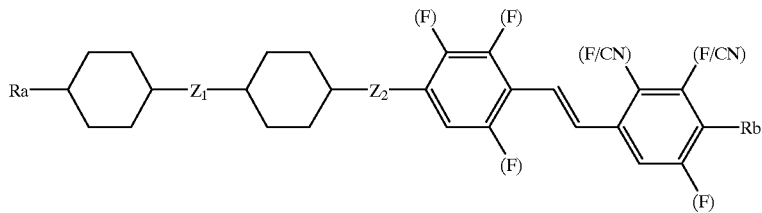
(1-46)
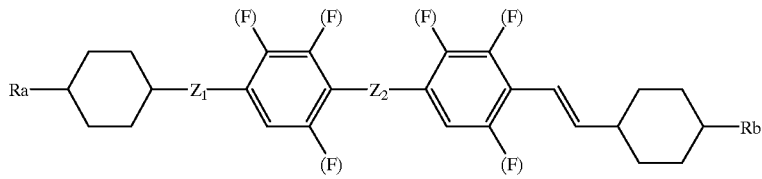
(1-47)
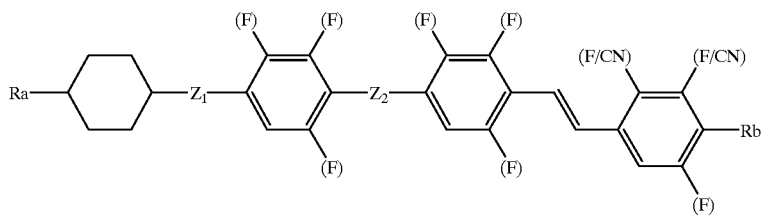
(1-48)
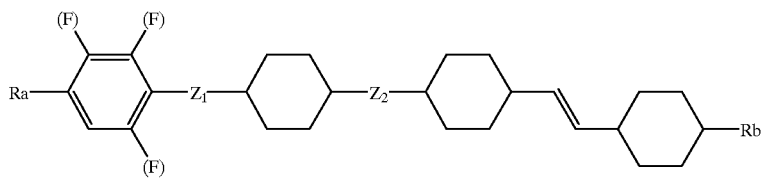
(1-49)
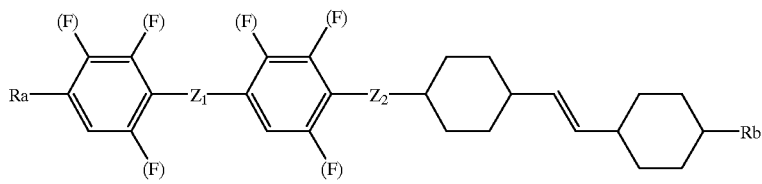
(1-50)
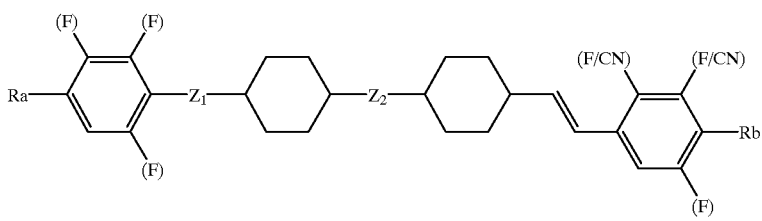
(1-52)
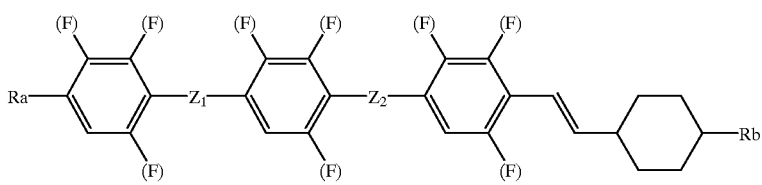
(1-53)

-continued
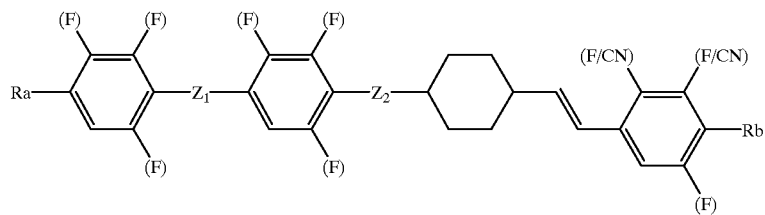
(1-54)
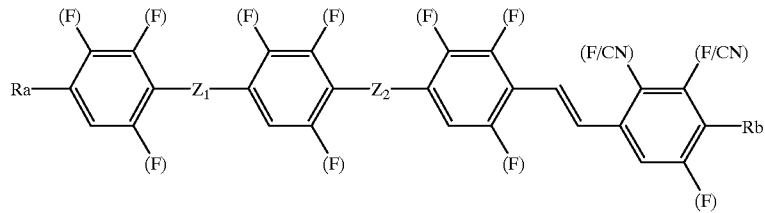
(1-55)
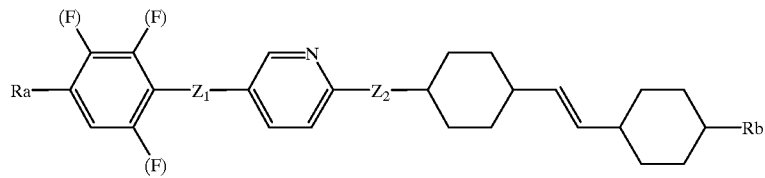
(1-56)
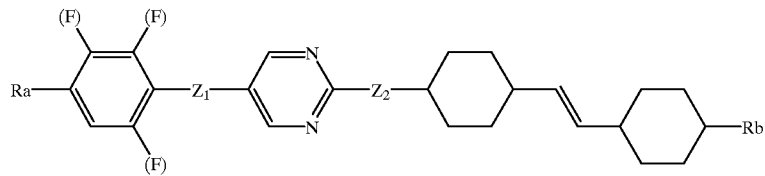
(1-57)
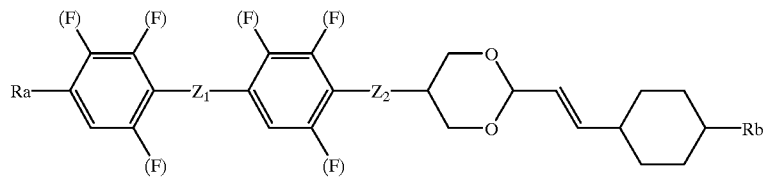
(1-58)
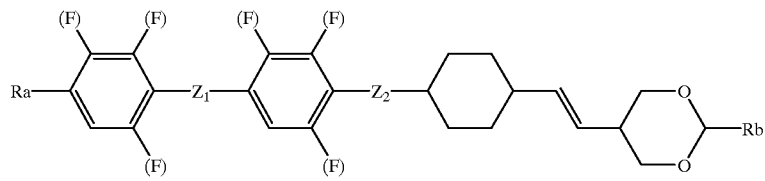
(1-59)
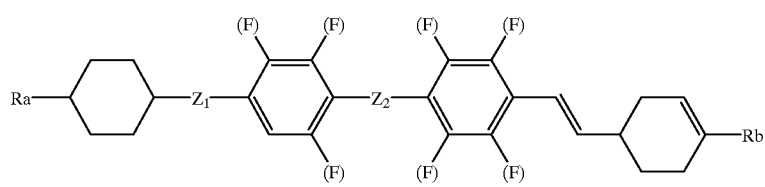
(1-60)

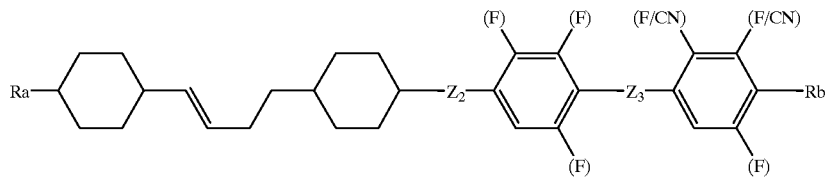
(1-61)
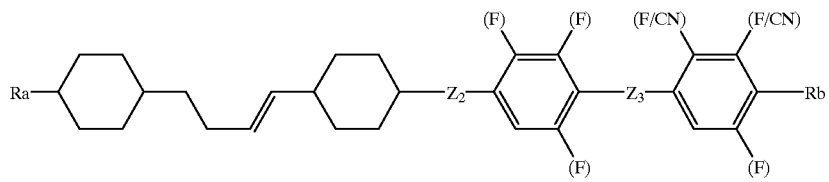
(1-62)
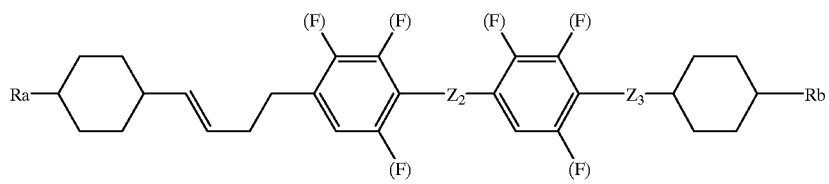
(1-63)
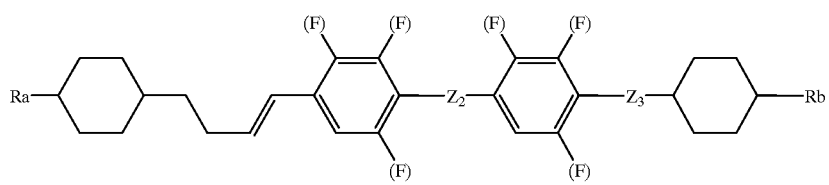
(1-64)
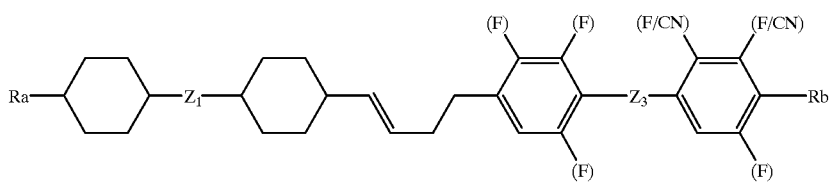
(1-65)
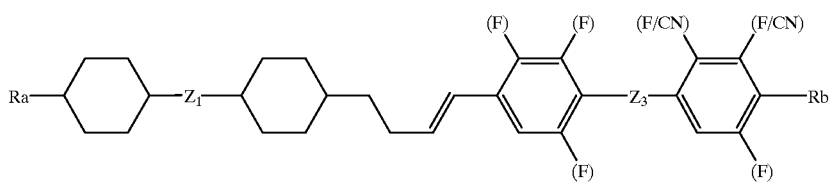
(1-66)
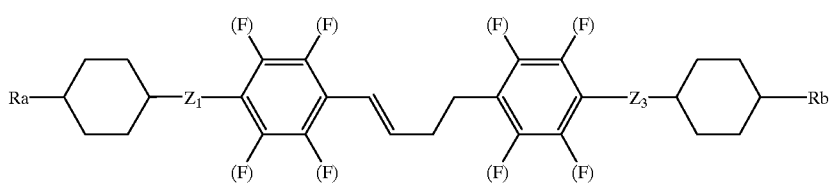
(1-67)

(1-68)
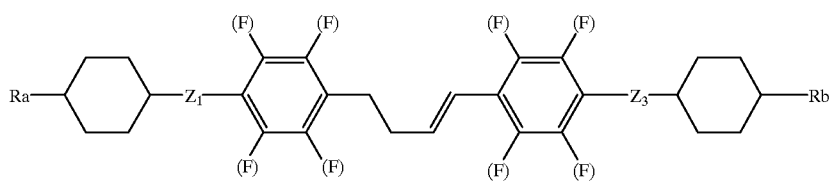
(1-69)
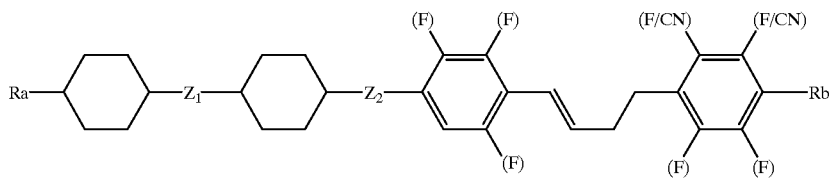
(1-70)
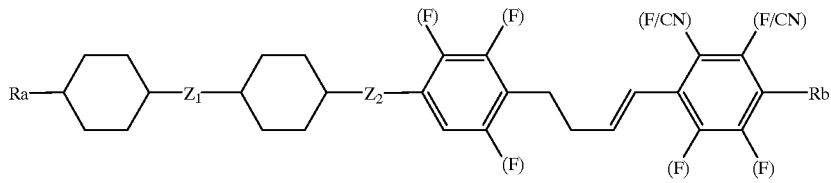
(1-71)
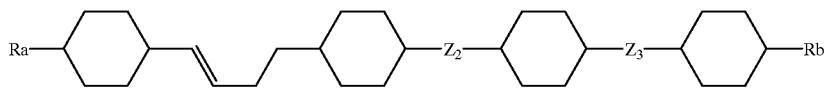
(1-72)
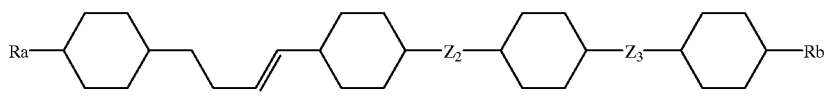
(1-73)
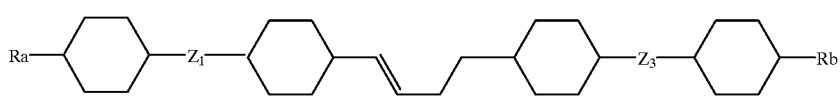
(1-74)
(1-75)
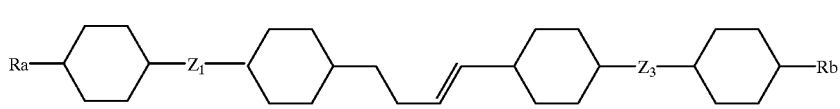
(1-76)
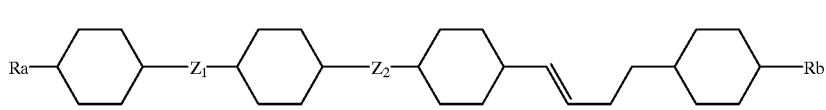
(1-77)
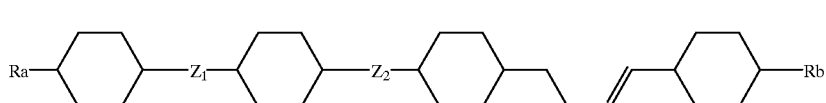

wherein Ra, Rb, and $Z_1$ to $Z_3$ are defined in the same way as described above, and the hydrogen atom on 1,4-phenylene group may independently be replaced by the atom or group described in the parentheses.

While the liquid crystalline compounds of the present invention expressed by the general formula (1) can be produced by general methods in organic synthesis known in public, the compounds can conveniently be produced by the following methods:

For instance, double bond can readily be introduced in the molecule by the Wittig reaction (Organic Reactions, Vol. 14, Chapter 3), the Wittig-Schlosser Reaction (M. Schlosser et al., Angewandte Chemie International Edition in English, 5, 126 (1966)), or the Wittig-Horner Reaction (J. I. G. Cadgan, Organophosphorus Reagents in Organic Synthesis, Academic (1979).

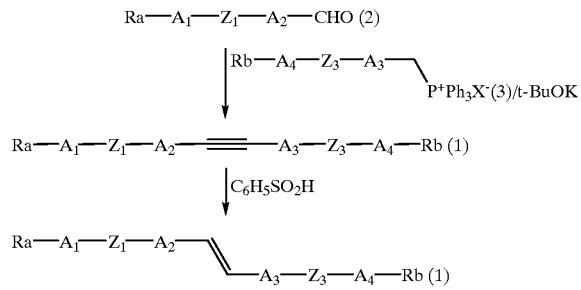

wherein Ra, Rb, $A_1$ to $A_4$, and $Z_1$ to $Z_3$ are defined in the same way as described above, and X represents a halogen atom.

That is, aldehydes (2) can be reacted with phosphonium salts (3) in a solvent such as tetrahydrofuran and diethyl ether in the presence of a base such as potassium-tert-butoxide (t-BuOK) and n-butyl lithium to produce examples of the compounds (1) of the present invention. This reaction is preferably conducted under an inert gas atmosphere at a temperature in the range of $-5°$ C. to the boiling point of the solvent. Besides, it is possible to isomerize the compounds thus obtained by treating with benzenesulfinic acid or p-toluenesulfinic acid.

Further, the compounds can be produced by a method in which a vinyl Grignard reagent is subjected to a coupling reaction with a halide in the presence of a catalyst such as $Pd(PPh_3)_4$, $PdCl_2(PPh_3)_2$, $NiCl_2$ (dpp) (T. V. Lee et al., Tetrahedron Letters, 46, 921 (1990)), or a method in which an aldehyde is reacted with a Grignard reagent and then heated to dehydrate in a solvent such as toluene or xylene in the presence of an acidic catalyst such as p-toluenesulfinic acid.

Aldehydes (2) which are starting materials can be produced by known general methods in organic synthesis or their combination. For instance, the aldehydes can readily be produced by various methods such as the Jones oxidation (A. Bowers et al., Journal of the Chemical Society, 2548, 1953), the Collins oxidation (J. C. Collins et al., Organic Synthesis, VI, 644 (1988)), oxidation of alcohol derivatives with pyridinium chlorochromate (E. J. Corey et al., Tetrahedron Letters, 2647 (1975)), pyridinium dichromate (E. J. Corey et al., Tetrahedron Letters, 399 (1979)), the Swern oxidation (A. J. Mancuso et al., Synthesis, 165, (1981)), or activated manganese dioxide (A. J. Fatiadi et al., Synthesis, 65 (1976)), reduction of ester derivatives with diisobutylaluminium hydride (DIBAL) (E. Winterfeldt, Synthesis, 617 (1975)), sodium bis(2-methoxyethoxy)aluminum hydride (J. Malek, Organic Reactions, 26, 249 (1988)), sodium aluminium hydride (L. I. Zakharkin et al., Tetrahedron Letters, 2087 (1963)), or bis(N-methylpiparazino)aluminium hydride (M. Muradi et al., chemistry Letters, 215 (1975)), reduction of nitrile derivatives with DIBAL (N. M. Yoon et al., The Journal of Organic Chemistry, 50, 2443 (1985), or triethoxyaluminium hydride (H. C. Brown et al., Journal of the American Chemical Society, 86, 1085 (1964)), and reaction of a Grignard reagent or lithium compound with a formylating reagent such as dimethylformamide (W. J. Dale et al., The Journal of Organic Chemistry, 26, 2225 (1961); G. Boss et al., Chemisch Berichte, 1199 (1989)) and N-formylpiperazine (G. A. Olah et al., Organic Synthesis, 64, 114 (1985)).

Phosphonium salts (3) which are other starting materials can be produced by reacting a corresponding halide with triphenylphosphine in a solvent such as toluene or xylene, or in the absence of a solvent.

Compounds expressed by the general formula (1) wherein Ra, Rb, $Z_1$, $Z_2$, or $Z_3$ is —C≡C— can be produced, for instance, by the method of W. Tao et al., (The Journal of Organic Chemistry, 55, 63 (1990)). That is, the compounds can be produced by reacting an acetylene derivative with a halide in an alkylamine solvent such as diethylamine and triethylamine in the presence of copper iodide and a Pd catalyst such as $Pd(PPh_3)_4$ and $PdCl_2(PPh_3)_2$. This reaction is preferably conducted under an inert gas atmosphere at a temperature in the range of room temperature to the boiling point of the solvent. The compounds can also be produced by performing the Castro reaction (M. D. Raush et al., The Journal of Organic Chemistry, 34, 468 (1969)).

Compounds expressed by the general formula (1) wherein Ra, Rb, $Z_1$, $Z_2$, or $Z_3$ is —COO— can be produced, for instance, by the process of J. Corey et al., (The Journal of Organic Chemistry, 38, 3223 (173)). That is, the compounds can be produced by converting a carboxylic acid into an acid halide with a halogenating agent such as thionyl chloride in a solvent such as toluene and benzene, or in the absence of solvent, and then reacting the acid halide with an alcohol derivative. This reaction is preferably conducted under an inert gas atmosphere at a temperature in the range of room temperature to the boiling point of the solvent, and more preferably conducted in the presence of a base such as pyridine, triethylamine (B. Iselin et al., Helvetica Chimica Acta, 40, 373 (1957)), dimethylaniline (C. Raha, Organic Synthesis, IV, 263 (1963)), or tetramethylurea (M. S. Newman et al., Tetrahedron Letters, 3267 (1967)) to accelerate the reaction. Alternatively, the compounds can be produced by reacting a carboxylic acid with an alcohol derivative in a solvent such as dichloromethane and chloroform in the presence of a dehydrating agent such as dicyclohexylcarbodiimide, and 4-dimethylamino-pyridine (B. Neises et al., Organic Synthesis, 63, 183 (1985).

Compounds expressed by the general formula (1) wherein Ra, Rb, $Z_1$, $Z_2$, or $Z_3$ is —O— can be produced, for instance, by reacting a halide with an alcohol derivative in a solvent such as dimethyl sulfoxide, dimethylformamide, 1,2-dimethoxymethane, tetrahydrofuran, hexamethylphosphoric acid triamide, or toluene in the presence of a base such as sodium amide (J. B. Wright et al., Journal of the American Chemical Society, 70, 3098 (1948)), potassium carbonate (W. T. Olson et al., Journal of the American Chemical Society, 69, 2451 (1947)), triethylamine (R. L. Merker et al., The Journal of Organic Chemistry, 26, 5180 (1961)), sodium hydroxide (C. Wilkins, Synthesis, 156 (1973)), potassium hydroxide (J. Rebek et al., The journal of Organic Chemistry, 44, 1485 (1979)), barium hydroxide (Kawabe et al., The Journal of Organic Chemistry, 37, 4210 (1972), or sodium hydride (C. J. Stark, Tetrahedron Letters, 22, 2089 (1981); Takai et al., Tetrahedron Letters, 21, 1657 (1980)).

Whereas general methods for producing the compounds of the present invention are described above, production of aldehyde derivatives which are starting materials are described below with reference to more specific examples.

BEST MODE FOR CARRYING OUT THE INVENTION

Scheme 1

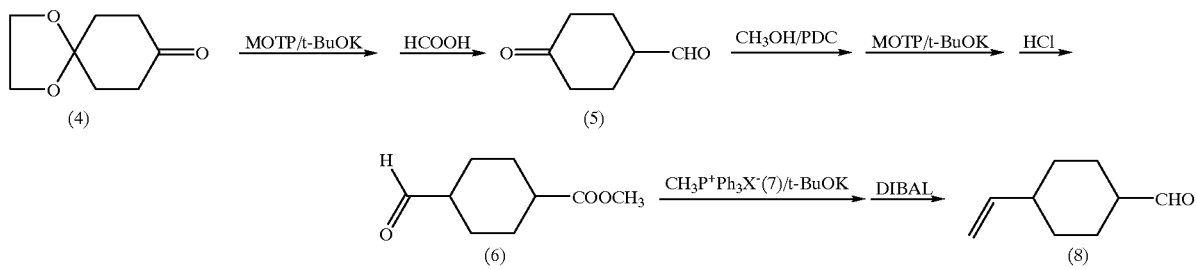

Scheme 2

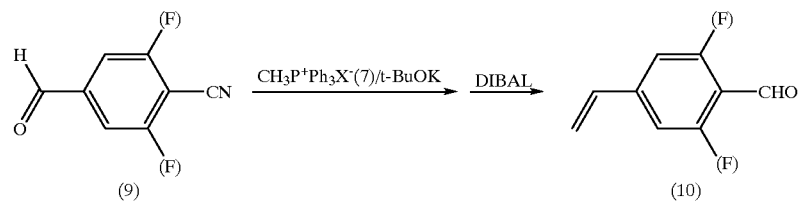

Scheme 3

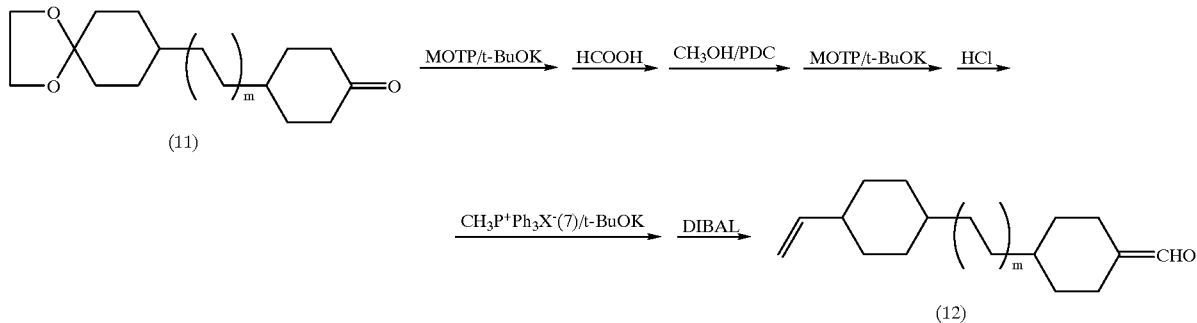

Scheme 4

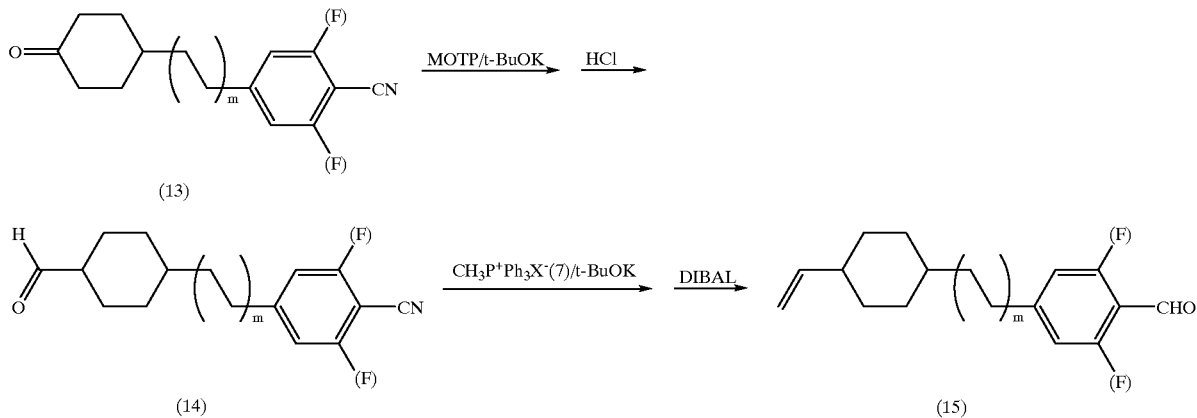

Scheme 5

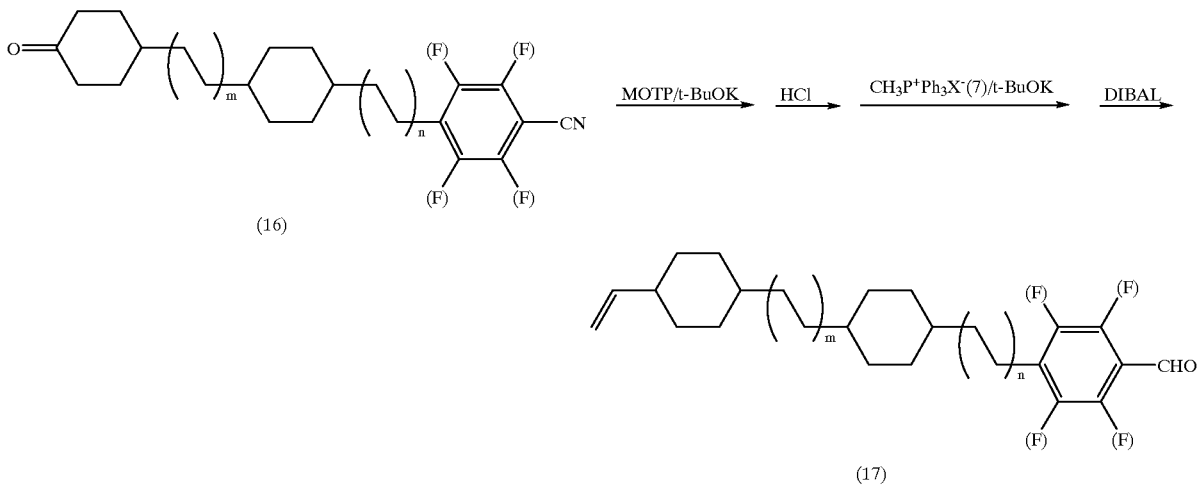

Scheme 6

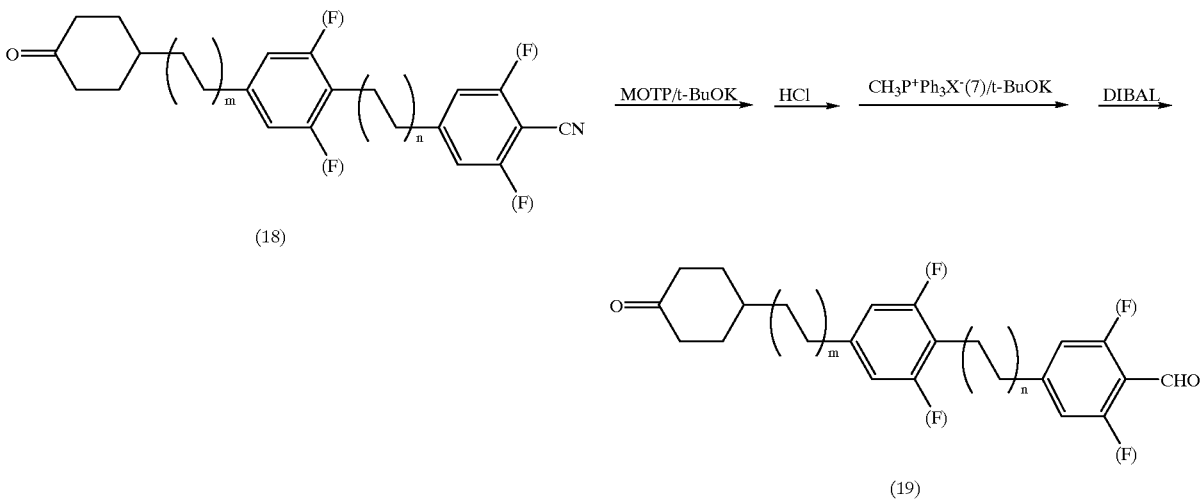

wherein X represents a halogen atom, m and n are independently an integer of 0 or 1, and the hydrogen atoms on 1,4-phenylene group may independently be replaced by fluorine atom.

As shown in scheme 1, cyclohexanedionemonocyclic acetal (4) and methoxymethyltriphenylphosphonium chloride (MOTP) are subjected to the Wittig reaction and then subjected to deprotection with hydrochloric acid, formic acid, acetic acid, or the like to produce compound (5). Subsequently, the compound (5) is reacted with an alcohol such as methanol and ethanol in the presence of pyridinium dichromate (PDC) and then subjected to the Wittig reaction and deprotection to form compound (6). An aldehyde derivative having a carbon chain of a desired length can be produced by repeating the Wittig reaction of the compound (6) with MOTP.

Aldehyde derivative (8) can be produced by subjecting compound (6) and phosphonium salt (7) to the Wittig reaction, and then reducing with a reducing agent such as DIBAL.

As shown in scheme 2, aldehyde derivative (10) can be produced by subjecting compound (9) and phosphonium salt (7) to the Wittig reaction and then reducing with a reducing agent such as DIBAL.

As shown in scheme 3, aldehyde derivative (12) can be produced in the same way as in scheme 1 with the exception that compound (4) is replaced by compound (11).

As shown in scheme 4, compound (13) is subjected to the Wittig reaction and then subjected to deprotection to convert into compound (14). Aldehyde derivative (15) can be produced by subjecting the compound (14) and phosphonium (7) to the Wittig reaction and then reducing with a reducing agent such as DIBAL.

As shown in scheme 5, aldehyde derivative (17) can be produced in the same way as in scheme 4 with the exception that compound (13) is replaced by compound (16).

Further, as shown in scheme 6, aldehyde derivative (19) can be produced in the same way as in scheme 4 with the exception that compound (13) is replaced by compound (18).

The phosphonium salt can be produced by the method as follows:

Scheme 7

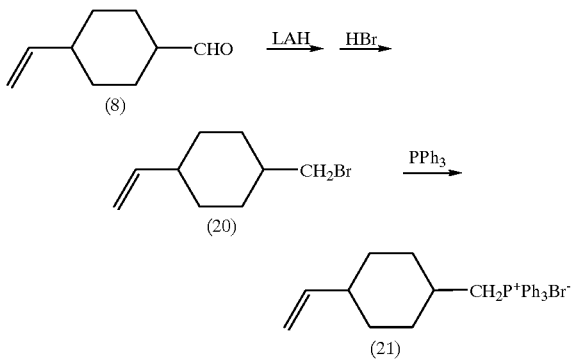

That is, as shown in scheme 7, the aldehyde derivative (8) described above is reduced with a reducing agent such as lithium aluminum hydride (LAH) and then halogenated with a halogenating reagent such as hydrobromic acid and hydroiodic acid to form compound (20). Phosphonium salt (21) can be produced by reacting the compound (20) with triphenylphosphine.

Further, by using the aldehyde derivative (10), (12), (15), (17), or (19) described above in place of aldehyde derivative (8), a corresponding phosphonium salt can be produced, respectively.

Whereas the reactions described above are all known in public, it is needless to say that other known reactions can be used when necessary in addition to the above described reactions.

Various kind of the liquid crystalline compounds of the present invention expressed by the general formula (1) can be produced from various kind of aldehyde derivatives and phosphonium salts thus obtained.

Liquid crystalline compounds of the present invention obtained by such methods are wide in temperature range in which the compounds exhibit liquid crystal phase, low in viscosity, readily mixed with various liquid crystal materials, and excellent in miscibility even at low temperatures. Besides, the compounds exhibit a suitable value of $\Delta\epsilon$ and $\Delta n$. The liquid crystalline compounds of the present invention are sufficiently stable physically and chemically under conditions in which liquid crystal display devices are ordinarily used, and thus are remarkably excellent as component of nematic liquid crystal compositions.

Also, the compounds of the present invention can preferably be used as component in liquid crystal compositions for TN, STN, or TFT.

Among the compounds expressed by the general formula (1), the compounds having two or more cyclohexane rings in the molecule exhibit a comparatively low $\Delta n$ and a low viscosity, and the compounds having two or more aromatic rings exhibit an especially wide temperature range of liquid crystal phase, and a particularly high transition temperature to isotropic phase and high $\Delta n$. Further, the compounds having pyridine ring, pyrimidine ring, or dioxane ring exhibit a comparatively high $\Delta\epsilon$.

Since the compounds of the present invention expressed by the general formula (1) have a large elastic constant ratio (bend elastic constant/splay elastic constant), liquid crystal compositions which are steep in the change of transmittance of the T-V curve can be produced and display devices having a high contrast can be provided by using the compounds as component of liquid crystal composition for STN.

Moreover, the compounds of the present invention can be made into more preferable liquid crystalline compounds as component of liquid crystal compositions for STN by introducing double bond into both Ra and Rb.

Compounds expressed by the general formula (1) wherein group Ra or group Rb is an optically active group are particularly useful as chiral dopant. In the case where Rb is a halogen atom, halogen substituted alkyl group, or halogen substituted alkoxy group, the compounds exhibit a high $\Delta\epsilon$, and in the case where it is cyano group, the compounds exhibit an especially high $\Delta\epsilon$.

It is possible to make $\Delta\epsilon$ higher by replacing the hydrogen atom on the ring structure by fluorine atom, and mutual solubility can be improved at the same time.

Compounds expressed by the general formula (1) wherein any one of $Z_1$, $Z_2$, and $Z_3$ is triple bond exhibit a high $\Delta n$. Compounds in which any one of $Z_1$, $Z_2$, and $Z_3$ is difluoromethyleneoxy (—$CF_2O$—) or oxydifluoromethylene (—$OCF_2$—) exhibit a comparatively high $\Delta\epsilon$ and low viscosity, and the compounds in which it is 1,2-difluorovinylene (—CF=CF—) exhibit a remarkably low viscosity.

From these facts, it can be seen that novel liquid crystalline compounds having desired physical properties can be obtained by selecting a proper ring, substituent and/or bonding group.

While the liquid crystal compositions provided according to the present invention are ones comprising at least one liquid crystalline compound expressed by the general formula (1), they are preferably mixtures comprising a first component comprising at least one liquid crystalline compound expressed by the general formula (1) and a second component comprising at least one compound (hereinafter referred to as second component A) selected from the group consisting of the compounds expressed by any one of the general formulas (2), (3), and (4) and/or at least one compound (hereinafter referred to as second component B) selected from the group consisting of the compounds expressed by any one of the general formulas (5), (6), (7), (8), and (9). Further, known compounds can be mixed, as a third component, to the first component and the second component described above for the purpose of adjusting threshold voltage, temperature range of liquid crystal phase, optical anisotropy value, dielectric anisotropy value, and viscosity.

Among the second component A described above, compounds expressed by one of the formulas (2-1) to (2-15) can be mentioned as preferable examples of the compounds expressed by the general formula (2); compounds expressed by one of the formulas (3-1) to (3-48) can be mentioned as preferable examples of the compounds expressed by the general formula (3); and the compounds expressed by one of the formulas (4-1) to (4-55) can be mentioned as preferable examples of the compounds expressed by the general formula (4), respectively.

(2-1)

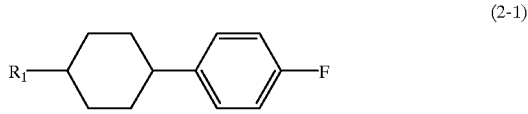

(2-2) 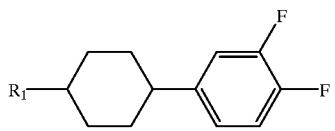
(2-3) 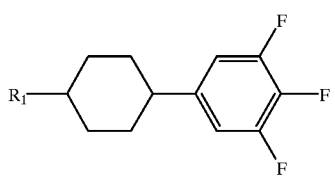
(2-4) 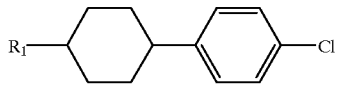
(2-5) 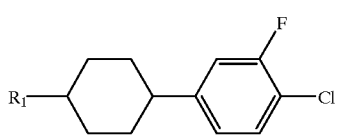
(2-6) 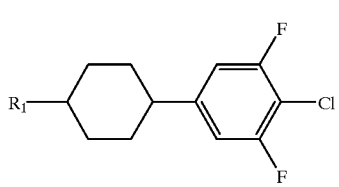
(2-7) 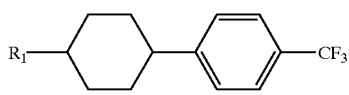
(2-8) 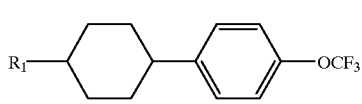
(2-9) 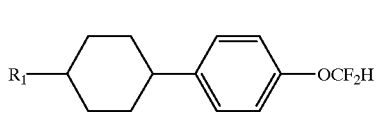
(2-10) 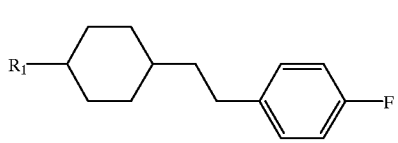
(2-11) 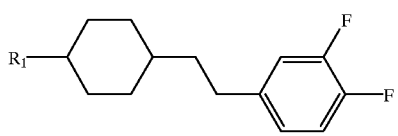
(2-12) 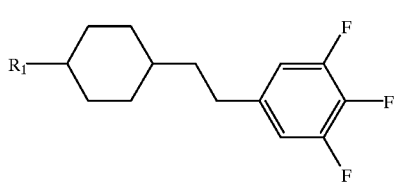
(2-13) 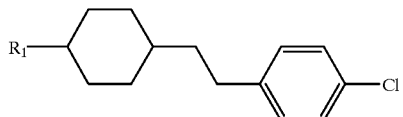
(2-14) 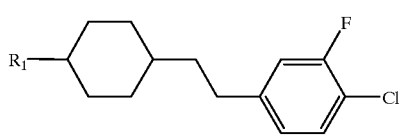
(2-15) 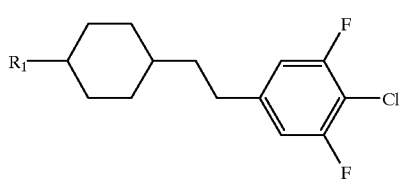
(3-1) 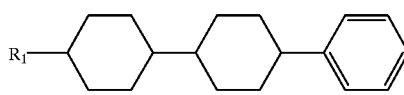
(3-2) 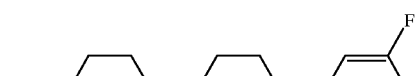
(3-3) 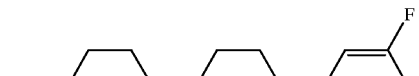
(3-4) 
(3-5) 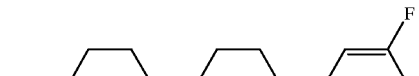
(3-6) 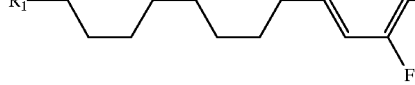
(3-7) 

(3-8)
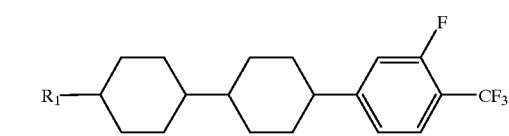
(3-9)
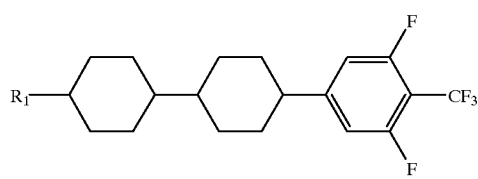
(3-10)
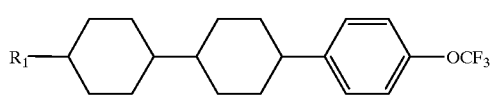
(3-11)
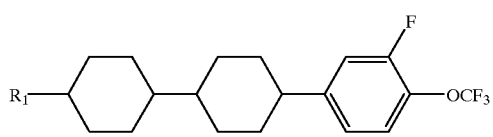
(3-12)
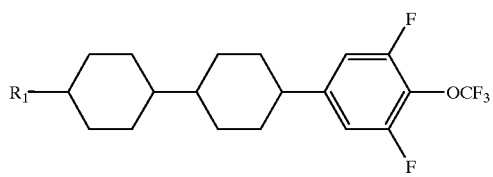
(3-13)
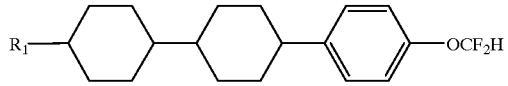
(3-14)
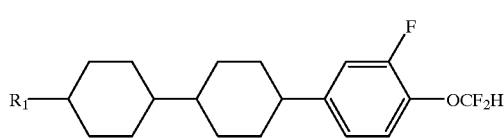
(3-15)
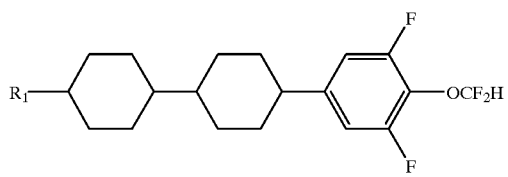
(3-16)
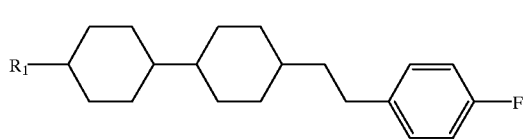
(3-17)
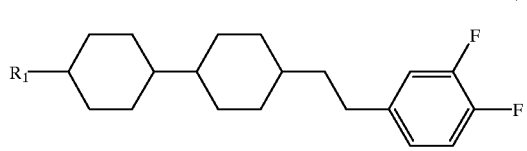
(3-18)
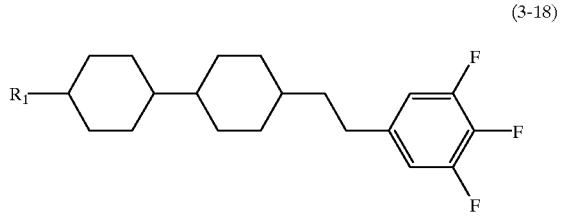
(3-19)
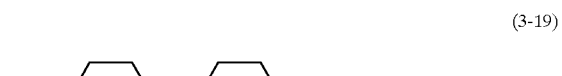
(3-20)
(3-21)
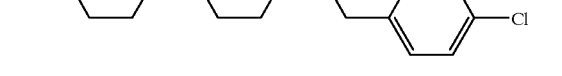
(3-22)
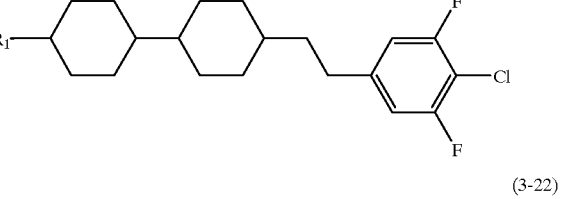
(3-23)
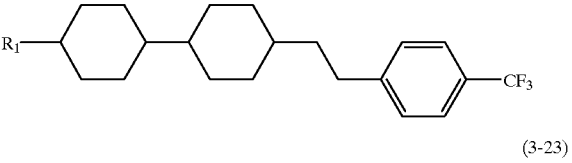
(3-24)
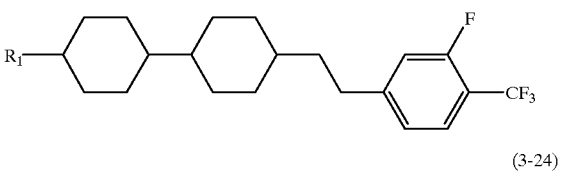

-continued
(3-25)
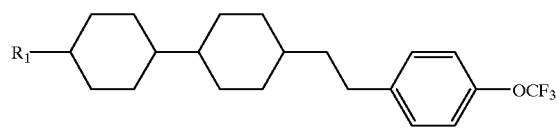
(3-26)
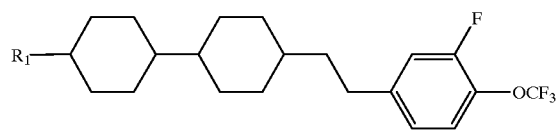
(3-27)
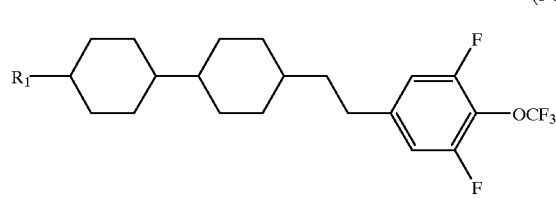
(3-28)
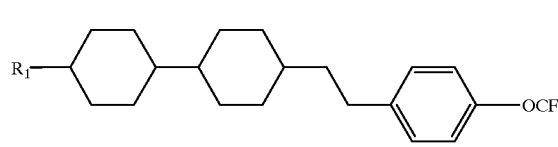
(3-29)
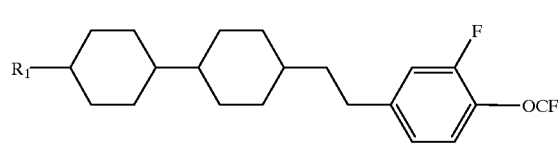
(3-30)
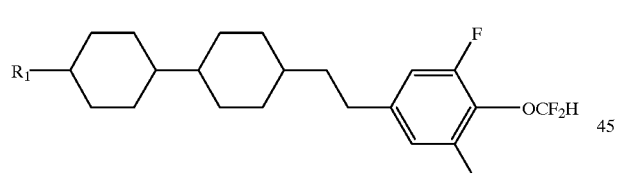
(3-31)
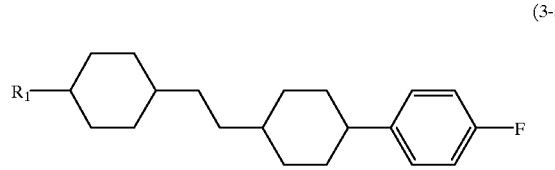
(3-32)
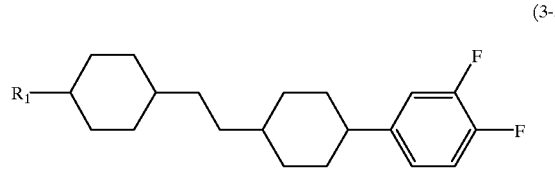
-continued
(3-33)
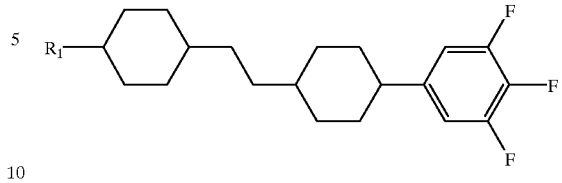
(3-34)
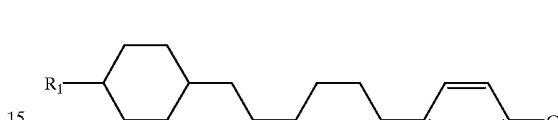
(3-35)
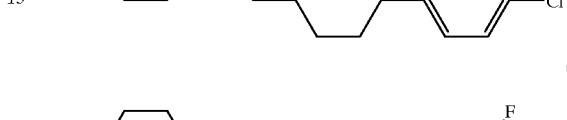
(3-36)
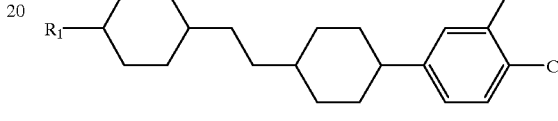
(3-37)
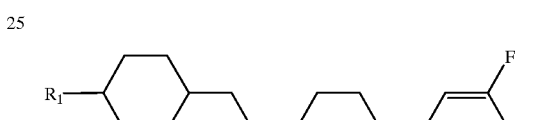
(3-38)
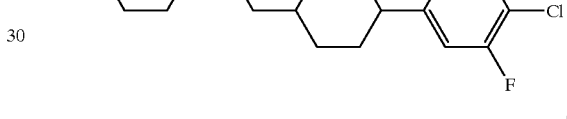
(3-39)
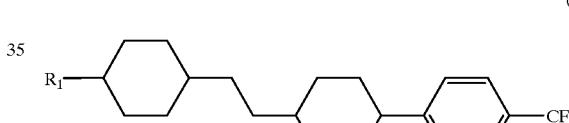
(3-40)
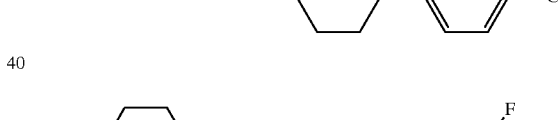

(3-41) 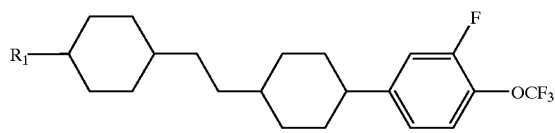
(3-42) 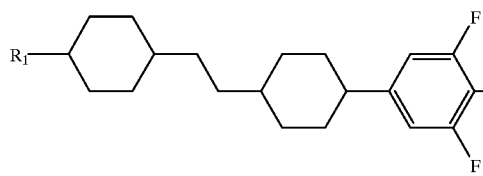
(3-43) 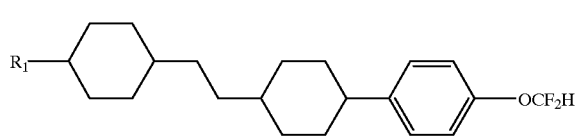
(3-44) 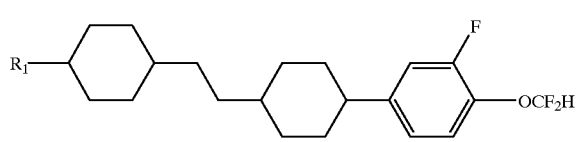
(3-45) 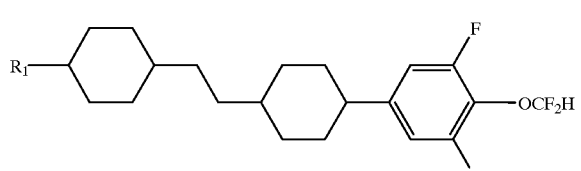
(3-46) 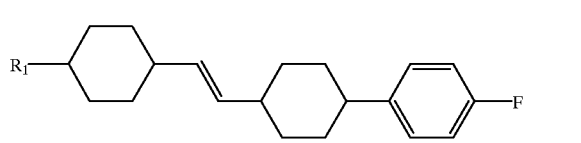
(3-47) 
(3-48) 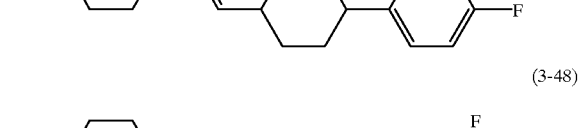
(4-1) 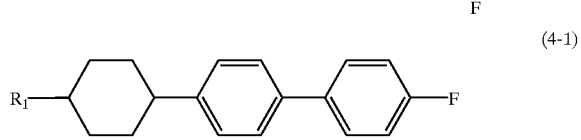
(4-2) 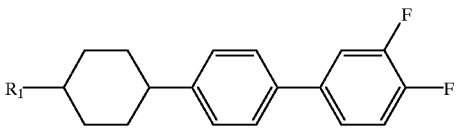
(4-3) 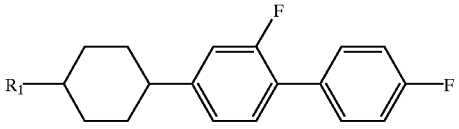
(4-4) 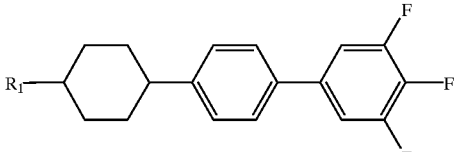
(4-5) 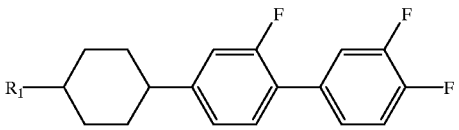
(4-6) 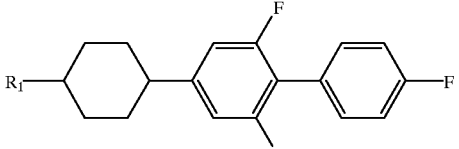
(4-7) 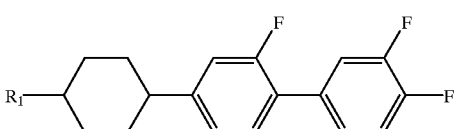
(4-8) 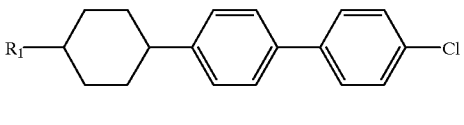
(4-9) 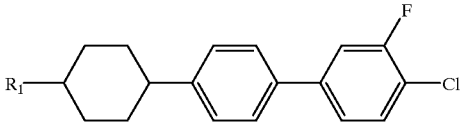
(4-10) 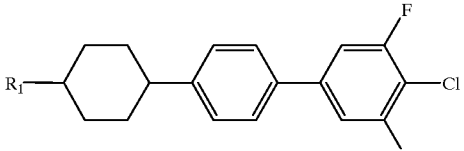
(4-11) 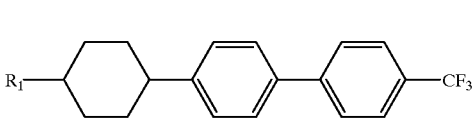

-continued
(4-12)
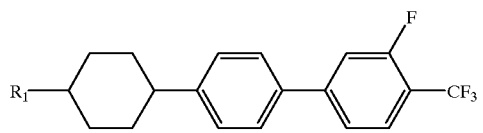
(4-13)
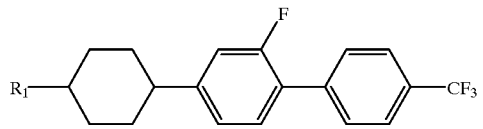
(4-14)
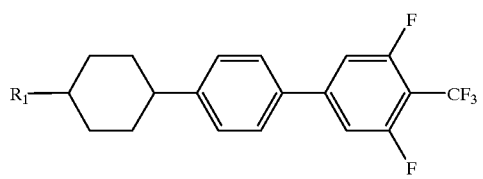
(4-15)
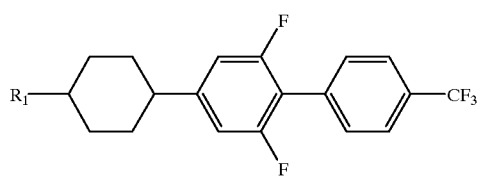
(4-16)
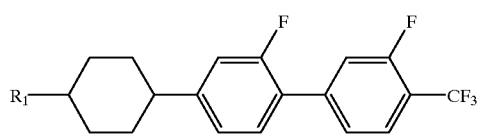
(4-17)
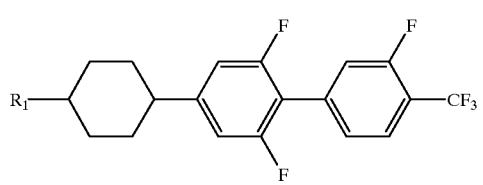
(4-18)
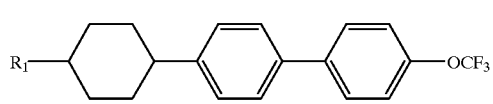
(4-19)
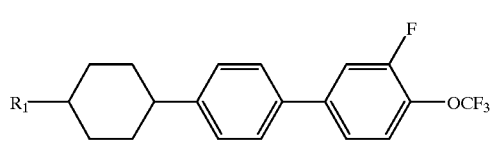
(4-20)
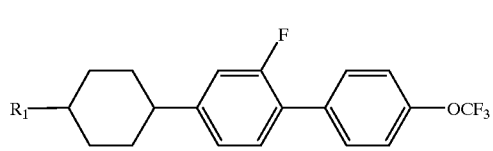
-continued
(4-21)
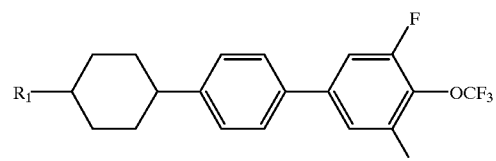
(4-22)
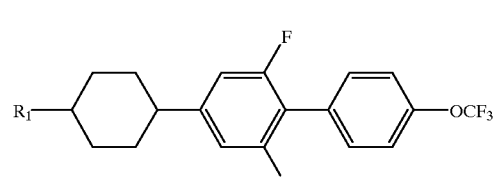
(4-23)
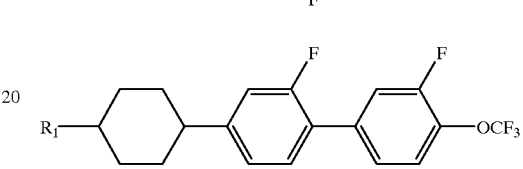
(4-24)
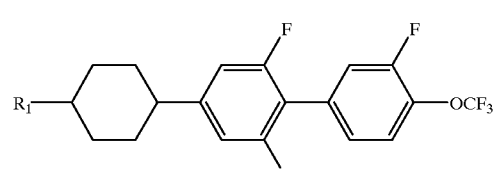
(4-25)
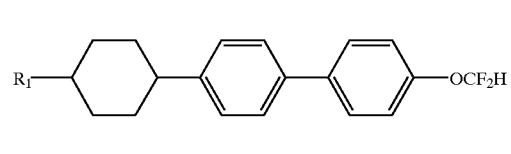
(4-26)
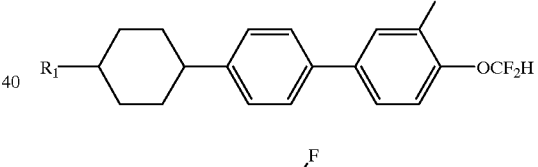
(4-27)
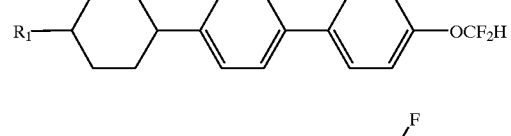
(4-28)
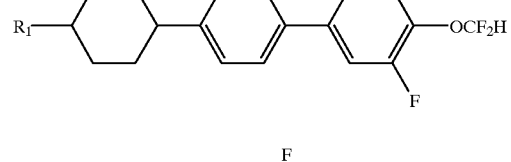
(4-29)
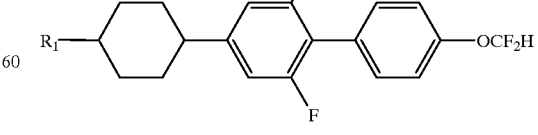

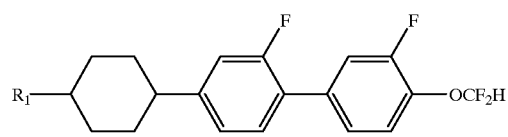 (4-30)
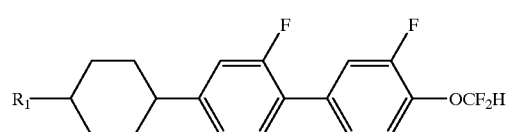 (4-31)
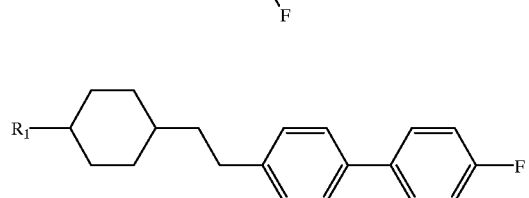 (4-32)
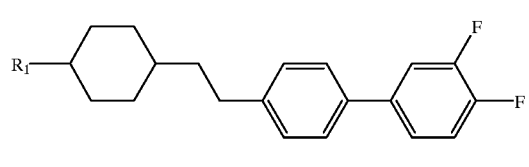 (4-33)
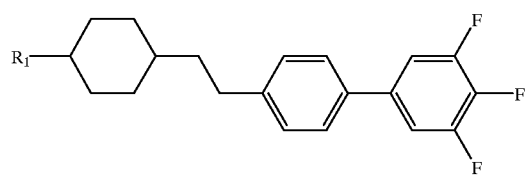 (4-34)
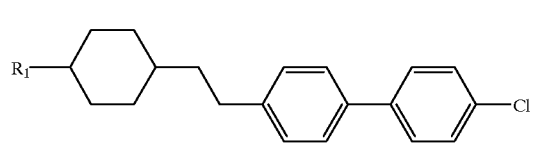 (4-35)
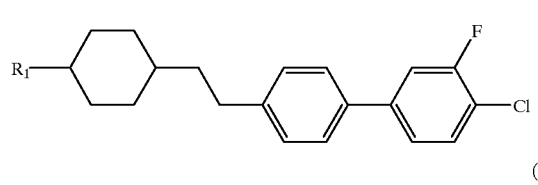 (4-36)
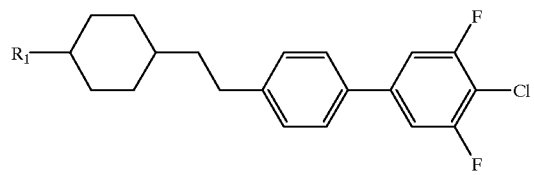 (4-37)
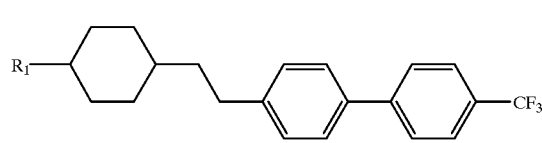 (4-38)
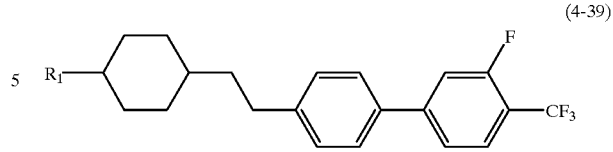 (4-39)
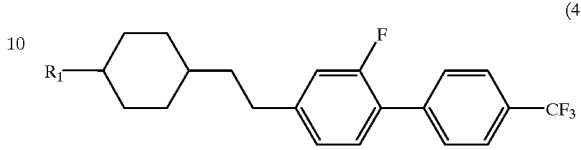 (4-40)
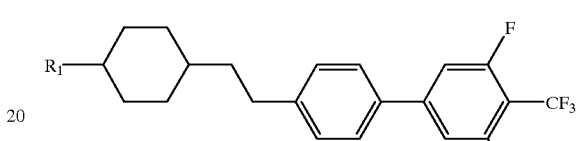 (4-41)
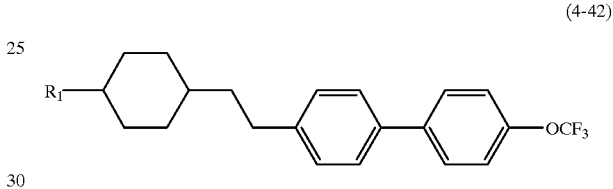 (4-42)
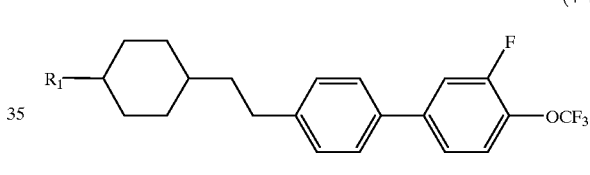 (4-43)
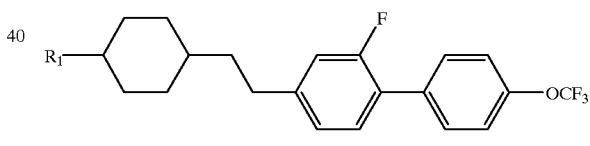 (4-44)
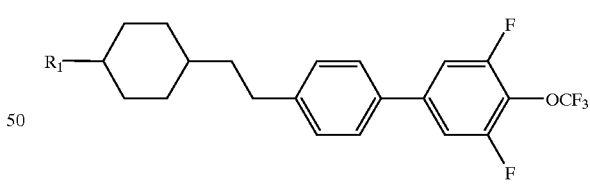 (4-45)
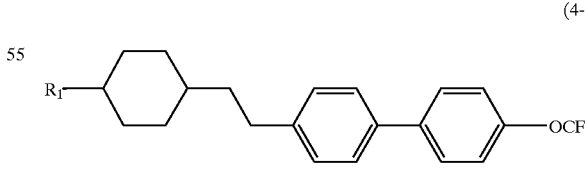 (4-46)
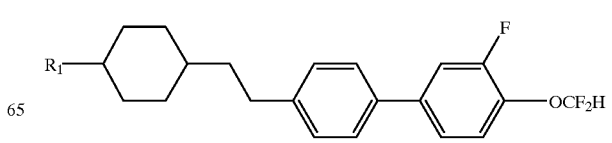 (4-47)

-continued (4-48)
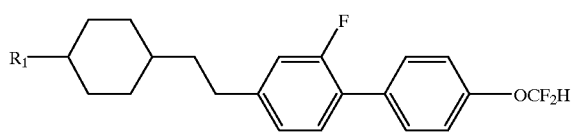

(4-49)

(4-50)

(4-51)

(4-52)

(4-53)

(4-54)

(4-55)

Compounds expressed by one of the general formulas (2) to (4) have a positive value of dielectric anisotropy and are remarkably excellent in thermal stability and chemical stability.

Amount of these compounds to be contained in the liquid crystal compositions of the present invention is suitably in the range of 1 to 99% by weight, preferably 10 to 97% by weight, and more desirably 40 to 95% by weight based on the total amount of liquid crystal composition.

Next, among the second component B described above, compounds expressed by one of the formulas (5-1) to (5-24), (6-1) to (6-3), or (7-1) to (7-28) can be mentioned as preferable examples of the compounds expressed by the general formula (5), (6), or (7), respectively.

(5-1)
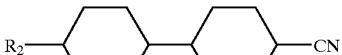

(5-2)
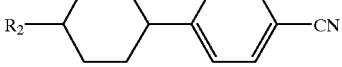

(5-3)
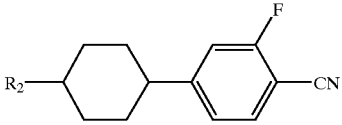

(5-4)

(5-5)
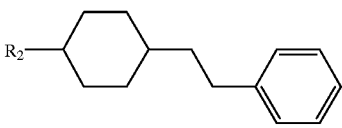

(5-6)
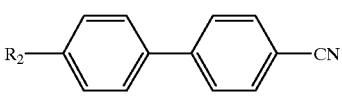

(5-7)
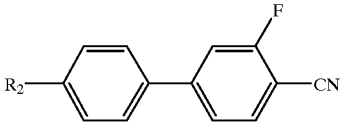

(5-8)

(5-9)
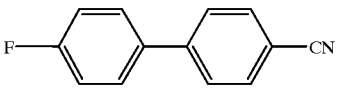

(5-10)
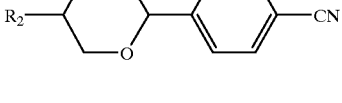

(5-11)
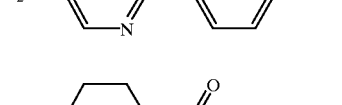

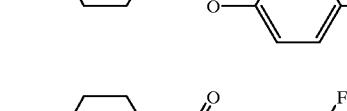

(5-12) 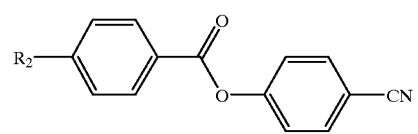
(5-13) 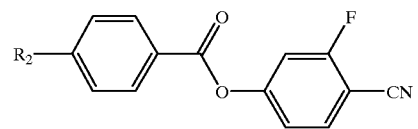
(5-14) 
(5-15) 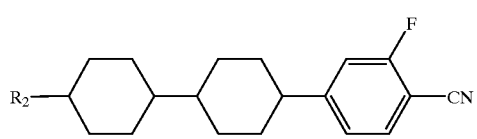
(5-16) 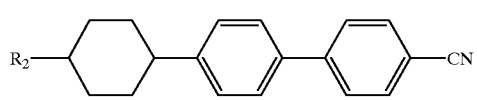
(5-17) 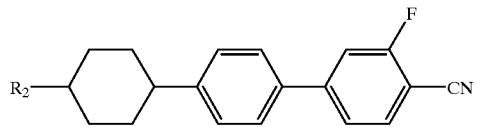
(5-18) 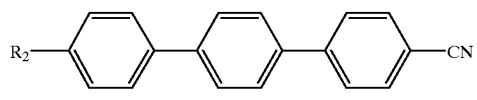
(5-19) 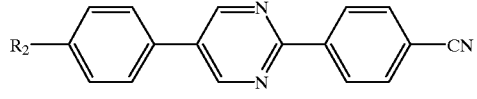
(5-20) 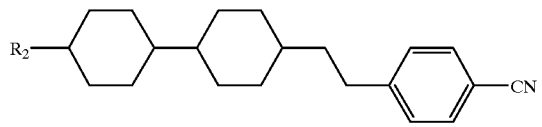
(5-21) 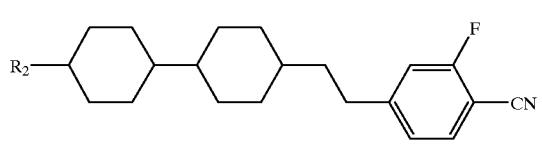
(5-22) 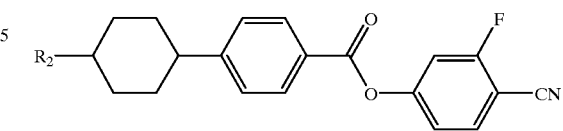
(5-23) 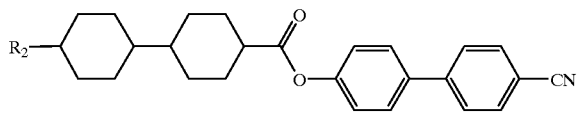
(5-24) 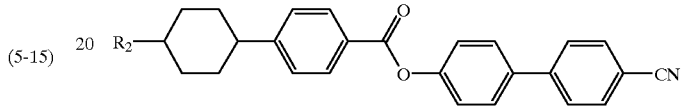
(6-1) 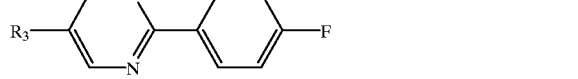
(6-2) 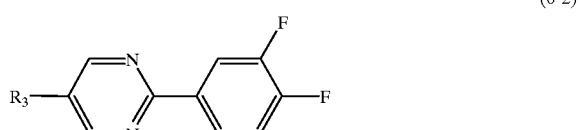
(6-3) 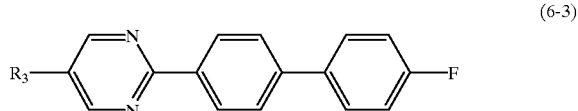
(7-1) 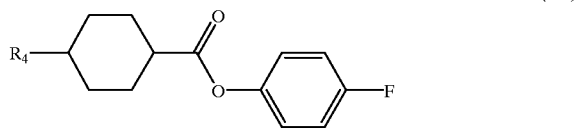
(7-2) 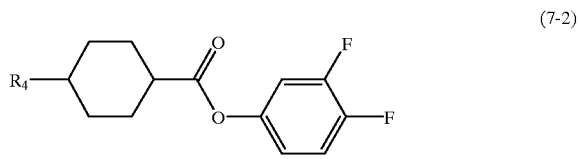
(7-3) 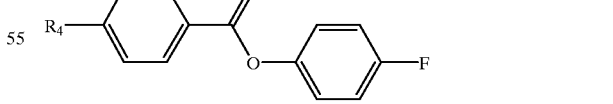
(7-4) 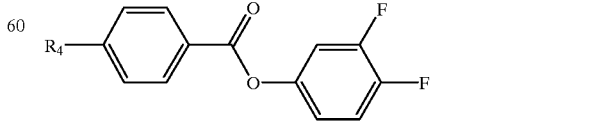

(7-5), (7-6), (7-7), (7-8), (7-9), (7-10), (7-11), (7-12), (7-13), (7-14), (7-15), (7-16), (7-17), (7-18), (7-19), (7-20)

-continued (7-21)
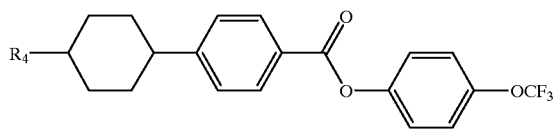

(7-22)
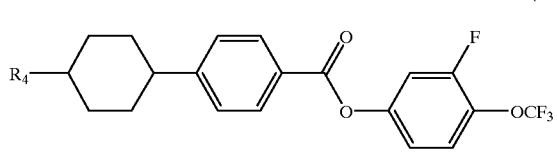

(7-23)
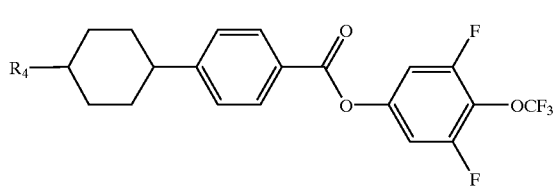

(7-24)
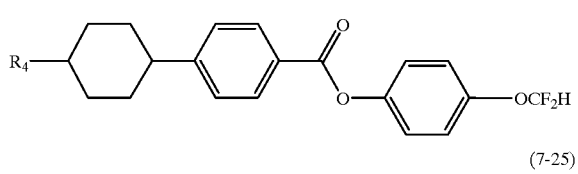

(7-25)
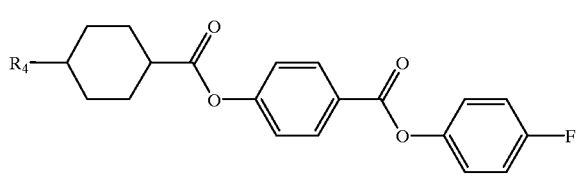

(7-26)
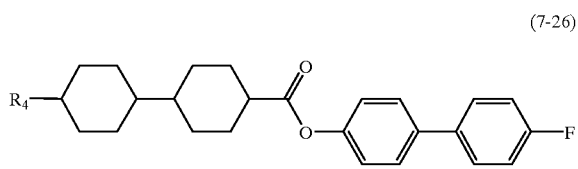

(7-27)
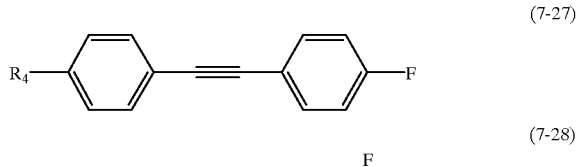

(7-28)
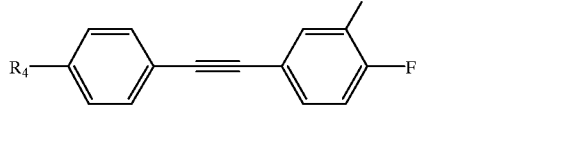

Compounds expressed by one of the general formulas (5) to (7) have a large positive value of dielectric anisotropy and are used as component for lowering threshold voltage of liquid crystal compositions. Also, they are used for the purpose of adjusting viscosity, adjusting optical anisotropy value, and widening the temperature range of liquid crystal phase, and further for the purpose of improving the steepness of T-V curve.

Among the second component B, the compounds expressed by one of the formulas (8-1) to (8—8) and (9-1) to (9-12) can be mentioned as preferable examples of the compounds expressed by the general formula (8) or (9).

(8-1)
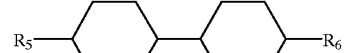

(8-2)
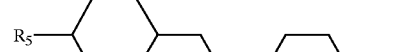

(8-3)
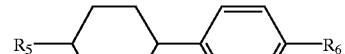

(8-4)
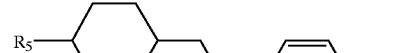

(8-5)
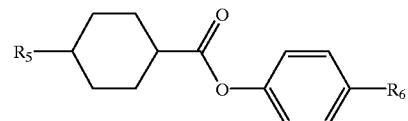

(8-6)
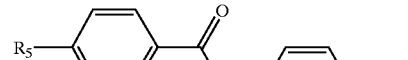

(8-7)

(8-8)
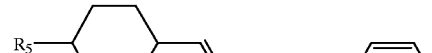

(9-1)

(9-2)
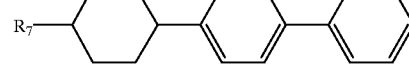

(9-3)
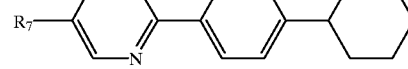

(9-4)
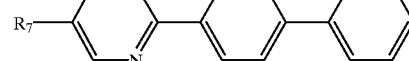

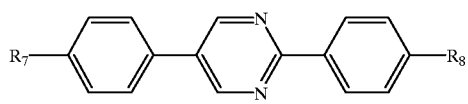 (9-5)

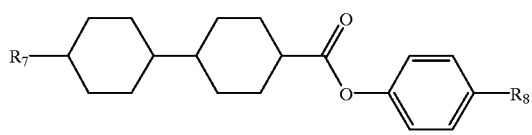 (9-6)

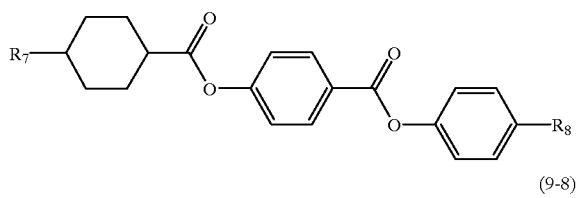 (9-7)

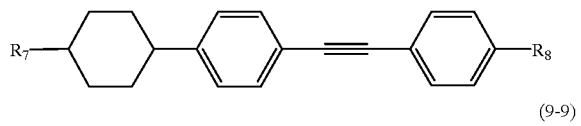 (9-8)

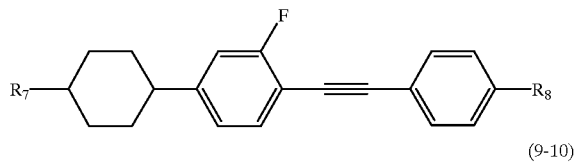 (9-9)

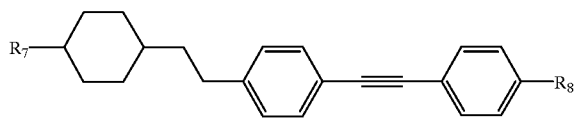 (9-10)

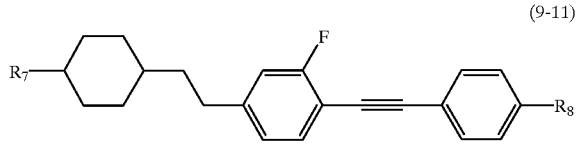 (9-11)

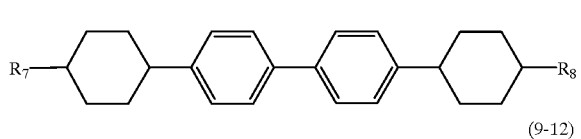 (9-11)

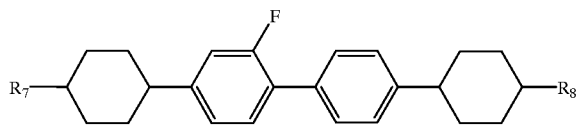 (9-12)

Compounds expressed by the general formula (8) or (9) have a negative or small positive dielectric anisotropy value. Compounds expressed by the general formula (8) are used for the purpose of principally reducing viscosity of liquid crystal compositions or for the purpose of adjusting optical anisotropy value, and the compounds expressed by the general formula (9) are used for the purpose of widening temperature range of liquid crystal phase and/or for the purpose of adjusting optical anisotropy value.

Compounds expressed by one of the general formulas (5) to (9) are useful when liquid crystal compositions for STN display or TN display are produced. Content of these compounds in the liquid crystal compositions of the present invention is suitably in the range of 1 to 99% by weight, preferably 10 to 97% by weight, and more desirably 40 to 95% by weight based on the total amount of liquid crystal composition when liquid crystal compositions for the STN display or TN display are produced.

Liquid crystal compositions provided according to the present invention preferably comprises at least one liquid crystalline compound expressed by the general formula (1) in the ration of 0.1 to 99% by weight to develop excellent characteristics.

Liquid crystal compositions of the present invention can be produced by methods which are known in public by themselves, for instance, by a method wherein various components are dissolved in each other at a high temperature. Liquid crystal compositions of the present invention are improved and optimized depending on intended uses by adding a suitable additive when necessary. Such an additive is well known in the art and described in the literature in detail. Usually, a chiral dopant or the like having such an effect as of inducing the helical structure of liquid crystals thereby adjust a required twisting angle, and of avoiding reverse-twist is added. As its specific examples, the following compounds can be mentioned.

Symbol: C15

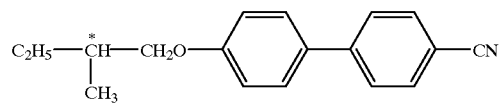

Symbol: CB15

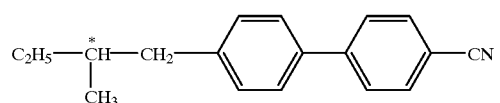

Symbol: CM21

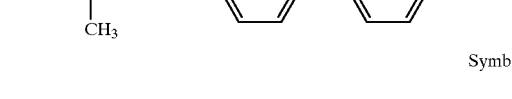

Symbol: CM33

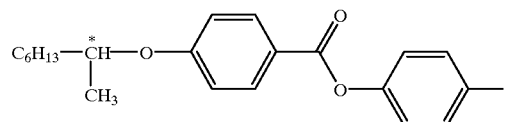

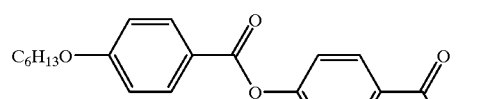

Symbol: CM43L

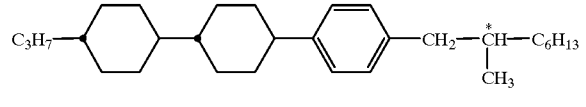

-continued

Symbol: CM45
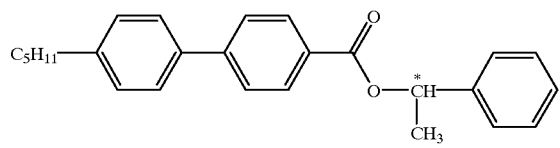

Symbol: CM47
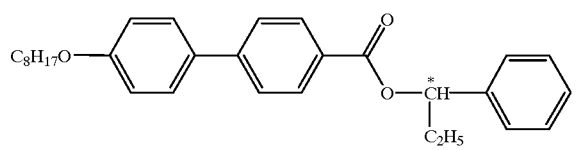

Symbol: CN
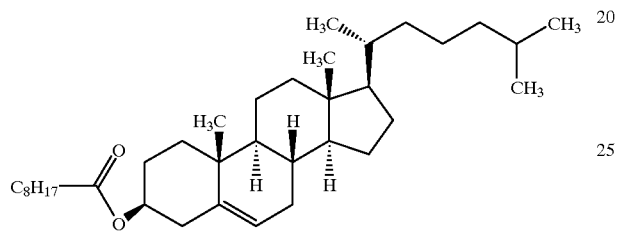

Liquid crystal compositions of the present invention can be used as ones for guest-host (GH) mode by adding a dichroic dye such as merocyanine type, styryl type, azo type, azomethine type, azoxy type, quinphthalone type, anthraquinone type, or tetrazine type dye. Liquid crystal compositions of the present invention can also be used as ones for NCAP which is prepared by the microencapsulation of a nematic liquid crystal, or for a polymer dispersed liquid crystal display device (PDLCD) prepared by forming polymers of three-dimensional reticulated structure in a liquid crystal, including, for example, a polymer network liquid crystal display device (PNLCD). In addition, the liquid crystal compositions of the present invention can be used as ones for electrically controlled birefringence (ECB) mode or dynamic scattering (DS) mode.

As examples of liquid crystal compositions comprising the compounds of the present invention, the followings can be mentioned. In the composition examples, compounds are expressed by the symbols according to the definitions shown below. Number of compounds are the same as those shown in the Examples described below.

| Left side terminal group Rc | | Bonding group Za—Zn | | |
|---|---|---|---|---|
| $C_aH_{2a+1}$— | a- | —$CH_2CH_2$— | 2 | |
| $C_aH_{2a+1}O$— | aO- | —COO— | E | |
| $C_aH_{2a+1}OC_bH_{2b}$— | aOb- | —C≡C— | T | |
| $CH_2$=$CHC_aH_{2a}$— | Va- | —CH=CH— | V | |
| $C_aH_{2a+1}CH$=$CHC_bH_{2b}$— | aVb- | —$CF_2O$— | CF2O | |
| $C_aH_{2a+1}CH$=$CHC_bH_{2b}CH$=$CHC_cH_{2c}$— | aVbVc- | —$OCF_2$— | OCF2 | |
| $FC_aH_{2a}$— | Fa- | | | |
| $FC_aH_{2a}CH$=$CHC_bH_{2b}$— | FaVb- | | | |

| Ring structure | | Right side terminal group Rd | | |
|---|---|---|---|---|
| ⎯⌬⎯ | B | —F | | —F |
| ⎯⌬(F)⎯ | B(F) | —Cl<br>—CN | | —CL<br>—C |
| ⎯⌬(F,F)⎯ | B(F,F) | —$CF_3$<br>—$OCF_3$ | | —CF3<br>—OCF3 |

-continued

| Structure | Symbol | Group | Group |
|---|---|---|---|
| cyclohexyl | H | —OCF$_2$H | —OCF2H |
| pyrimidinyl | Py | —C$_w$H$_{2w+1}$<br>—OC$_w$H$_{2w+1}$ | —w<br>—Ow |
| dioxanyl | D | —C$_w$H$_{2w}$CH=CH$_2$<br>—C$_w$H$_{2w}$CH=CHC$_x$H$_{2x+1}$ | —wV<br>—wVx |
| cyclohexenyl | Ch | —COOCH$_3$ | —EMe |

Composition Example 1

| | | |
|---|---|---|
| V-HVHBB-4 | (Compound No. 1) | 3.0% by weight |
| V2-HB-C | | 10.0% by weight |
| 1V2-HB-C | | 10.0% by weight |
| 3-HB-C | | 26.0% by weight |
| 5-HB-C | | 12.0% by weight |
| 3-HB(F)-C | | 8.0% by weight |
| 2-BEB-C | | 3.0% by weight |
| V2-HHB-1 | | 8.0% by weight |
| 3-HHB-O1 | | 4.0% by weight |
| 3-HHB-3 | | 10.0% by weight |
| 3-H2BTB-2 | | 2.0% by weight |
| 3-H2BTB-3 | | 2.0% by weight |
| 3-H2BTB-4 | | 2.0% by weight |

Composition Example 2

| | | |
|---|---|---|
| V-HHVBB-3 | (Compound No. 41) | 3.0% by weight |
| 1V-HHVBB-3 | (Compound No. 50) | 3.0% by weight |
| 1V2-BEB(F,F)-C | | 11.0% by weight |
| 2O1-BEB(F)-C | | 5.0% by weight |
| 3O1-BEB(F)-C | | 9.0% by weight |
| 3-HB(F)-C | | 5.0% by weight |
| 3-HH-4 | | 3.0% by weight |
| 1O1-HH-3 | | 3.0% by weight |
| 4-BTB-O2 | | 6.0% by weight |
| 2-HHB(F)-C | | 13.0% by weight |
| 3-HHB(F)-C | | 14.0% by weight |
| 3-H2BTB-2 | | 2.0% by weight |
| 3-H2BTB-3 | | 2.0% by weight |
| 3-H2BTB-4 | | 2.0% by weight |
| 2-BTB-1 | | 3.0% by weight |
| 3-HH-2V | | 3.0% by weight |
| 4-HH-V | | 3.0% by weight |

Composition Example 3

| | | |
|---|---|---|
| 2V-HBVBH-2 | (Compound No. 52) | 2.0% by weight |
| 1V2-HB(F)VBH-3 | (Compound No. 53) | 2.0% by weight |
| F2V-HBVBH-V | (Compound No. 54) | 2.0% by weight |
| 2-BB-C | | 3.0% by weight |

-continued

| | | |
|---|---|---|
| 3O-BB-C | | 3.0% by weight |
| 2O2O-BB-C | | 3.0% by weight |
| 1O1-HB-C | | 10% by weight |
| 2O1-HB-C | | 7.0% by weight |
| 2-BEB-C | | 12.0% by weight |
| 5-PyB-F | | 6.0% by weight |
| 2-PyB-2 | | 2.0% by weight |
| 3-PyB-2 | | 2.0% by weight |
| 4-PyB-2 | | 2.0% by weight |
| 6-PyB-O2 | | 2.0% by weight |
| V-HHB-1 | | 5.0% by weight |
| 3-HHB-1 | | 7.0% by weight |
| 3-HHB-3 | | 6.0% by weight |
| 2-PyBH-3 | | 4.0% by weight |
| 3-PyBH-3 | | 4.0% by weight |
| 4-PyBH-3 | | 7.0% by weight |
| 3-PyBB-F | | 3.0% by weight |
| 4-PyBB-F | | 3.0% by weight |
| 6-PyBB-2 | | 3.0% by weight |

Composition Example 4

| | | |
|---|---|---|
| V-HVBBH-5 | (Compound No. 10) | 3.0% by weight |
| 3-PyB(F)-F | | 6.0% by weight |
| 2-BEB-C | | 12.0% by weight |
| 3-BEB-C | | 4.0% by weight |
| 3-DB-C | | 10.0% by weight |
| 4-DB-C | | 10.0% by weight |
| 3-HEB-O4 | | 12.0% by weight |
| 4-HEB-O2 | | 9.0% by weight |
| 5-HEB-O1 | | 9.0% by weight |
| 3-HHB-1 | | 6.0% by weight |
| 3-HHEBB-C | | 2.0% by weight |
| 3-HBEBB-C | | 2.0% by weight |
| 5-HBEBB-C | | 2.0% by weight |
| 1O-BEB-2 | | 3.0% by weight |
| 4-HEB-3 | | 5.0% by weight |
| 5-HEB-1 | | 5.0% by weight |

Composition Example 5

| | | |
|---|---|---|
| V-HVHBB-4 | (Compound No. 1) | 3.0% by weight |
| V-HHVBB-3 | (Compound No. 41) | 2.0% by weight |
| 1V-HHVBB-2V | (Compound No. 51) | 2.0% by weight |
| 3-HB-C | | 18.5% by weight |
| 3-HHB-1 | | 5.0% by weight |
| 3-HHB-3 | | 5.0% by weight |
| 5-HEB-F | | 2.5% by weight |
| 7-HEB-F | | 2.5% by weight |
| 3-HHEB-F | | 1.0% by weight |
| 5-HHEB-F | | 1.0% by weight |
| 3-HEB-O4 | | 4.0% by weight |
| 4-HEB-O2 | | 3.0% by weight |
| 5-HEB-O1 | | 3.0% by weight |
| 3-HEB-O2 | | 2.5% by weight |
| 5-HEB-O2 | | 2.0% by weight |
| 3-HB(F)TB-2 | | 6.0% by weight |
| 3-HB(F)TB-3 | | 6.0% by weight |
| 3-HB(F)VB-4 | | 6.0% by weight |
| 3-H2BTB-2 | | 4.0% by weight |
| 3-H2BTB-3 | | 4.0% by weight |
| 3-H2BTB-4 | | 4.0% by weight |
| 5-HHEBB-C | | 3.0% by weight |
| 3-HBEBB-C | | 3.0% by weight |
| 3-HEBEB-F | | 2.0% by weight |
| 3-HH-COOMe | | 3.0% by weight |
| 1O1-HBBH-3 | | 2.0% by weight |

Composition Example 6

| | | |
|---|---|---|
| V-HHVBB-3 | (Compound No. 41) | 5.0% by weight |
| 5-PyB(F)-F | | 13.0% by weight |
| 2-HB(F)-C | | 10.0% by weight |
| 3-HB(F)-C | | 12.0% by weight |
| 3O-BB-C | | 8.0% by weight |
| 2-HHB-C | | 5.0% by weight |
| 3-HHB-C | | 5.0% by weight |
| 4-HHB-C | | 5.0% by weight |
| 5-HHB-C | | 5.0% by weight |
| 2-HHB(F)-C | | 7.0% by weight |
| 3-HHB(F)-C | | 7.0% by weight |
| 3-PyBB-F | | 5.0% by weight |
| 4-PyBB-F | | 5.0% by weight |
| 5-HHB-C | | 4.0% by weight |
| 3-HB(F)EB(F)-C | | 4.0% by weight |

Composition Example 7

| | | |
|---|---|---|
| V-HVHBB-4 | (Compound No. 1) | 5.0% by weight |
| 1V2-HB(F)VBH-3 | (Compound No. 53) | 5.0% by weight |
| 5-H2B(F)-F | | 4.0% by weight |
| 7-HB(F)-F | | 10.0% by weight |
| 2-HHB(F)-F | | 11.0% by weight |
| 3-HHB(F)-F | | 11.0% by weight |
| 5-HHB(F)-F | | 11.0% by weight |
| 2-H2HB(F)-F | | 12.0% by weight |
| 3-H2HB(F)-F | | 6.0% by weight |
| 5-H2HB(F)-F | | 12.0% by weight |
| 2-HBB(F)-F | | 2.0% by weight |
| 3-HBB(F)-F | | 2.0% by weight |
| 5-HBB(F)-F | | 4.0% by weight |
| 3-HHB-F | | 5.0% by weight |

Composition Example 8

| | | |
|---|---|---|
| 1V-HHVBB-3 | (Compound No. 50) | 2.0% by weight |
| V-HVBBH-5 | (Compound No. 10) | 2.0% by weight |
| 7-HB(F,F)-F | | 5.0% by weight |
| 3-HBB(F,F)-F | | 8.0% by weight |
| 5-HBB(F,F)-F | | 8.0% by weight |
| 3-HHB(F,F)-F | | 7.0% by weight |
| 5-HHB(F,F)-F | | 5.0% by weight |
| 3-HH2B(F,F)-F | | 10.0% by weight |
| 5-HH2B(F,F)-F | | 5.0% by weight |
| 3-H2HB(F,F)-F | | 9.0% by weight |
| 4-H2HB(F,F)-F | | 9.0% by weight |
| 5-H2HB(F,F)-F | | 8.0% by weight |
| 3-HHEB(F,F)-F | | 8.0% by weight |
| 4-HHEB(F,F)-F | | 3.0% by weight |
| 5-HHEB(F,F)-F | | 3.0% by weight |
| 3-HBEB(F,F)-F | | 2.0% by weight |
| 5-HBEB(F,F)-F | | 2.0% by weight |
| 3-HHHB(F,F)-F | | 2.0% by weight |
| 5-HH2BB(F,F)-F | | 2.0% by weight |

Composition Example 9

| | | |
|---|---|---|
| V-HVHBB-4 | (Compound No. 1) | 6.0% by weight |
| 7-HB(F,F)-F | | 5.0% by weight |
| 2-HHB(F)-F | | 12.0% by weight |
| 3-HHB(F)-F | | 12.0% by weight |
| 5-HHB(F)-F | | 12.0% by weight |
| 2-H2HB(F)-F | | 4.0% by weight |
| 3-H2HB(F)-F | | 2.0% by weight |
| 5-H2HB(F)-F | | 4.0% by weight |
| 3-HHB(F,F)-F | | 8.0% by weight |
| 4-HHB(F,F)-F | | 4.0% by weight |
| 3-H2HB(F,F)-F | | 6.0% by weight |
| 4-H2HB(F,F)-F | | 5.0% by weight |
| 5-H2HB(F,F)-F | | 5.0% by weight |
| 3-HH2B(F,F)-F | | 8.0% by weight |
| 5-HH2B(F,F)-F | | 7.0% by weight |

Composition Example 10

| | | |
|---|---|---|
| V-HVHBB-4 | (Compound No. 1) | 2.0% by weight |
| V-HVBBH-5 | (Compound No. 10) | 2.0% by weight |
| F2V-HBVBH-V | (Compound No. 53) | 2.0% by weight |
| 5-HB-F | | 2.0% by weight |
| 7-HB(F)-F | | 3.0% by weight |
| 2-HHB(F)-F | | 15.0% by weight |
| 3-HHB(F)-F | | 15.0% by weight |
| 5-HHB(F)-F | | 15.0% by weight |
| 3-HB-O2 | | 15.0% by weight |
| 3-HHB-F | | 4.0% by weight |
| 3-HHB-1 | | 6.0% by weight |
| 2-HBB-F | | 6.0% by weight |
| 3-HBB-F | | 5.0% by weight |
| 3-HHEB-F | | 2.0% by weight |
| 5-HHEB-F | | 2.0% by weight |
| 3-HBEB-F | | 2.0% by weight |
| 3-HHEBB-F | | 2.0% by weight |

Composition Example 11

| | | |
|---|---|---|
| V-HVHBB-4 | (Compound No. 1) | 3.0% by weight |
| V-HHVBB-3 | (Compound No. 41) | 3.0% by weight |
| V-HVBBH-5 | (Compound No. 10) | 2.0% by weight |

-continued

| | | |
|---|---|---|
| 2V-HBVBH-2 | (Compound No. 52) | 2.0% by weight |
| 1V2-HB(F)VBH-3 | (Compound No. 53) | 2.0% by weight |
| 7-HB(F,F)-F | | 7.0% by weight |
| 3-HB-CL | | 7.0% by weight |
| 7-HB-CL | | 3.0% by weight |
| 2-BTB-O1 | | 12.0% by weight |
| 2-HBB(F)-F | | 2.5% by weight |
| 3-HBB(F)-F | | 2.5% by weight |
| 5-HBB(F)-F | | 5.0% by weight |
| 3-HBB(F,F)-F | | 8.0% by weight |
| 5-HBB(F,F)-F | | 8.0% by weight |
| 2-HHB-CL | | 8.0% by weight |
| 3-HHB-CL | | 5.0% by weight |
| 3-HB(F)TB-2 | | 3.0% by weight |
| 3-HB(F)TB-3 | | 3.0% by weight |
| 3-HB(F)TB-4 | | 3.0% by weight |
| 3-H2BTB-2 | | 3.0% by weight |
| 3-H2BTB-3 | | 3.0% by weight |
| 3-H2HB(F)-CL | | 2.0% by weight |
| 3-H2BB(F,F)-F | | 3.0% by weight |

Composition Example 12

| | | |
|---|---|---|
| 1V2-HB(F)VBH-3 | (Compound No. 53) | 5.0% by weight |
| F2V-HBVBH-V | (Compound No. 54) | 5.0% by weight |
| 5-HB-F | | 10.0% by weight |
| 6-HB-F | | 5.0% by weight |
| 7-HB-F | | 5.0% by weight |
| 2-HHB-OCF3 | | 7.0% by weight |
| 3-HHB-OCF3 | | 7.0% by weight |
| 5-HHB-OCF3 | | 6.0% by weight |
| 3-HH2B-OCF3 | | 6.0% by weight |
| 5-HH2B-OCF3 | | 6.0% by weight |
| 3-HB(F)B-3 | | 4.0% by weight |
| 5-HB(F)B-3 | | 4.0% by weight |
| 2-HBB(F)-F | | 10.0% by weight |
| 3-HBB(F)-F | | 10.0% by weight |
| 5-HBB(F)-F | | 10.0% by weight |

Composition Example 13

| | | |
|---|---|---|
| V-HHVBB-3 | (Compound No. 41) | 6.0% by weight |
| 2V-HBVBH-2 | (Compound No. 52) | 6.0% by weight |
| 5-HB-F | | 3.0% by weight |
| 6-HB-F | | 3.0% by weight |
| 7-HB-F | | 3.0% by weight |
| 3-HHB-OCHF2 | | 4.0% by weight |
| 5-HHB-OCHF2 | | 4.0% by weight |
| 3-HHB(F,F)-OCHF2 | | 9.0% by weight |
| 5-HHB(F,F)-OCHF2 | | 9.0% by weight |
| 2-HHB-OCF3 | | 6.0% by weight |
| 3-HHB-OCF3 | | 6.0% by weight |
| 4-HHB-OCF3 | | 6.0% by weight |
| 5-HHB-OCF3 | | 6.0% by weight |
| 3-HH2B(F)-F | | 10.0% by weight |
| 5-HH2B(F)-F | | 10.0% by weight |
| 3-HHEB(F)-F | | 4.0% by weight |
| 5-HHEB(F)-F | | 5.0% by weight |

Composition Example 14

| | | |
|---|---|---|
| V-HVHBB-4 | (Compound No. 1) | 10.0% by weight |
| 4-HHEB(F)-F | | 5.0% by weight |
| 5-HHEB(F)-F | | 5.0% by weight |
| 2-BEB(F)-C | | 6.0% by weight |

-continued

| | | |
|---|---|---|
| 3-BEB(F)-C | | 8.0% by weight |
| 4-BEB(F)-C | | 6.0% by weight |
| 5-BEB(F)-C | | 8.0% by weight |
| 1O3-HB(F)-C | | 7.0% by weight |
| 3-HHEB(F)-F | | 4.0% by weight |
| 5-HHEB(F)-F | | 4.0% by weight |
| 2-HBEB(F)-C | | 4.0% by weight |
| 3-HBEB(F)-C | | 4.0% by weight |
| 4-HBEB(F)-C | | 4.0% by weight |
| 5-HBEB(F)-C | | 4.0% by weight |
| 3-HBTB-2 | | 6.0% by weight |
| V2-HH-3 | | 10.0% by weight |
| V2-HHB-1 | | 5.0% by weight |

Composition Example 15

| | | |
|---|---|---|
| 1V-HHVBB-3 | (Compound No. 50) | 10.0% by weight |
| V2-HB-C | | 8.0% by weight |
| 4-BB-2 | | 5.0% by weight |
| 3-BB-C | | 5.0% by weight |
| 5-BB-C | | 5.0% by weight |
| 2-HB(F)-C | | 5.0% by weight |
| 3-H2B-O2 | | 5.0% by weight |
| 5-H2B-O3 | | 10.0% by weight |
| 3-BEB-C | | 5.0% by weight |
| 5-HEB-O1 | | 6.0% by weight |
| 5-HEB-O3 | | 6.0% by weight |
| 5-BBB-C | | 3.0% by weight |
| 4-BPyB-C | | 3.0% by weight |
| 4-BPyB-5 | | 3.0% by weight |
| 5-HB2B-4 | | 4.0% by weight |
| 5-HBB2B-3 | | 4.0% by weight |
| V2-HH-1O1 | | 8.0% by weight |
| 1V2-HBB-3 | | 5.0% by weight |

Composition Example 16

| | | |
|---|---|---|
| V-HHVBH-3 | (Compound No. 41) | 9.0% by weight |
| 1V2-BEB(F,F)-C | | 5.0% by weight |
| 3-HB-C | | 25.0% by weight |
| 1-BTB-3 | | 5.0% by weight |
| 2-BTB-1 | | 8.0% by weight |
| 3-HB-O2 | | 5.0% by weight |
| 3-HH-4 | | 8.0% by weight |
| 3-HHB-1 | | 11.0% by weight |
| 3-H2BTB-2 | | 4.0% by weight |
| 3-H2BTB-3 | | 4.0% by weight |
| 3-H2BTB-4 | | 4.0% by weight |
| 3-HB(F)TB-2 | | 6.0% by weight |
| 3-HB(F)TB-3 | | 6.0% by weight |

Composition Example 17

| | | |
|---|---|---|
| V-HHVHB-3 | (Compound No. 41) | 6.0% by weight |
| 2O1-BEB(F)-C | | 5.0% by weight |
| 3O1-BEB(F)-C | | 15.0% by weight |
| 4O1-BEB(F)-C | | 13.0% by weight |
| 5O1-BEB(F)-C | | 13.0% by weight |
| 2-HHB(F)-C | | 15.0% by weight |
| 3-HHB(F)-C | | 15.0% by weight |
| 3-HB(F)TB-2 | | 4.0% by weight |
| 3-HB(F)TB-3 | | 4.0% by weight |

-continued

| | | |
|---|---|---|
| 3-HB(F)TB-4 | | 4.0% by weight |
| 3-HHB-1 | | 2.0% by weight |
| 3-HHB-O1 | | 4.0% by weight |

Composition Example 18

| | | |
|---|---|---|
| V-HHVHB-3 | (Compound No. 41) | 5.0% by weight |
| 5-PyB-F | | 4.0% by weight |
| 3-PyB(F)-F | | 4.0% by weight |
| 2-BB-C | | 5.0% by weight |
| 4-BB-C | | 4.0% by weight |
| 5-BB-C | | 5.0% by weight |
| 3-HB-O2 | | 3.0% by weight |
| 2-PyB-2 | | 2.0% by weight |
| 3-PyB-2 | | 2.0% by weight |
| 4-PyB-2 | | 2.0% by weight |
| 6-PyB-O5 | | 3.0% by weight |
| 6-PyB-O6 | | 3.0% by weight |
| 6-PyB-O7 | | 3.0% by weight |
| 6-PyB-O8 | | 3.0% by weight |
| 3-PyBB-F | | 6.0% by weight |
| 4-PyBB-F | | 6.0% by weight |
| 5-PyBB-F | | 6.0% by weight |
| 3-HHB-1 | | 6.0% by weight |
| 2-H2BTB-2 | | 4.0% by weight |
| 2-H2BTB-3 | | 4.0% by weight |
| 2-B2BTB-4 | | 5.0% by weight |
| 3-H2BTB-2 | | 5.0% by weight |
| 3-H2BTB-3 | | 5.0% by weight |
| 3-H2BTB-4 | | 5.0% by weight |

Composition Example 19

| | | |
|---|---|---|
| V-HVHBB-4 | (Compound No. 1) | 5.0% by weight |
| V-HHVHB-3 | (Compound No. 41) | 7.0% by weight |
| 3-HB-C | | 18.0% by weight |
| 7-HB-C | | 3.0% by weight |
| 1O1-HB-C | | 10.0% by weight |
| 3-HB(F)-C | | 10.0% by weight |
| 3-HB-O2 | | 5.0% by weight |
| 2-PyB-2 | | 2.0% by weight |
| 3-PyB-2 | | 2.0% by weight |
| 4-PyB-2 | | 2.0% by weight |
| 1O1-HH-3 | | 5.0% by weight |
| 2-BTB-O1 | | 6.0% by weight |
| 3-HHB-1 | | 2.0% by weight |
| 3-HHB-F | | 2.0% by weight |
| 3-HHB-3 | | 8.0% by weight |
| 3-H2BTB-2 | | 3.0% by weight |
| 2-PyBH-3 | | 4.0% by weight |
| 3-PyBH-3 | | 3.0% by weight |
| 3-PyBB-2 | | 3.0% by weight |

Composition Example 20

| | | |
|---|---|---|
| V-HVHBB-4 | (Compound No. 1) | 4.0% by weight |
| V-HHVHB-3 | (Compound No. 41) | 6.0% by weight |
| V-HHVHB(F)-F | (Compound No. 44) | 4.0% by weight |
| 2O1-BEB(F)-C | | 5.0% by weight |
| 3O1-BEB(F)-C | | 12.0% by weight |
| 5O1-BEB(F)-C | | 4.0% by weight |
| 1V2-BEB(F,F)-C | | 10.0% by weight |
| 3-HH-EMe | | 10.0% by weight |
| 3-HB-O2 | | 18.0% by weight |
| 3-HB-O4 | | 6.0% by weight |

-continued

| | | |
|---|---|---|
| 7-HEB-F | | 2.0% by weight |
| 3-HHEB-F | | 2.0% by weight |
| 3-HBEB-F | | 4.0% by weight |
| 2O1-HBEB(F)-C | | 2.0% by weight |
| 3-HB(F)EB(F)-C | | 2.0% by weight |
| 3-HBEB(F,F)-C | | 2.0% by weight |
| 3-HHB-O1 | | 3.0% by weight |
| 3-HEBEB-F | | 2.0% by weight |
| 3-HEBEB-1 | | 2.0% by weight |

Composition Example 21

| | | |
|---|---|---|
| V-HVHBB-4 | (Compound No. 1) | 5.0% by weight |
| V-HHVHB-3 | (Compound No. 41) | 12.0% by weight |
| V-HHVHB(F)-F | | 10.0% by weight |
| 2O1-BEB(F)-C | | 5.0% by weight |
| 3O1-BEB(F)-C | | 12.0% by weight |
| 5O1-BEB(F)-C | | 4.0% by weight |
| 1V2-BEB(F,F)-C | | 16.0% by weight |
| 3-HB-C | | 10.0% by weight |
| 3-HB-O2 | | 10.0% by weight |
| 3-HH-4 | | 3.0% by weight |
| 3-HBEB-F | | 4.0% by weight |
| 3-H2BTB-4 | | 4.0% by weight |
| 3-HB(F)TB-2 | | 5.0% by weight |

Composition Example 22

| | | |
|---|---|---|
| V-HVHBB-4 | (Compound No. 1) | 5.0% by weight |
| V-HHVHB-3 | (Compound No. 41) | 14.0% by weight |
| 2-BEB-C | | 10.0% by weight |
| 5-BB-C | | 12.0% by weight |
| 7-BB-C | | 7.0% by weight |
| 3-HB-O2 | | 14.0% by weight |
| 1-BTB-3 | | 7.0% by weight |
| 2-BTB-1 | | 5.0% by weight |
| 1O-BEB-2 | | 10.0% by weight |
| 1O-BEB-5 | | 12.0% by weight |
| 2-HHB-1 | | 4.0% by weight |

Composition Example 23

| | | |
|---|---|---|
| V-HHVHB-3 | (Compound No. 41) | 2.0% by weight |
| V-HHVHB(F)-F | (Compound No. 44) | 5.0% by weight |
| 2-HHB(F)-F | | 17.0% by weight |
| 3-HHB(F)-F | | 17.0% by weight |
| 5-HHB(F)-F | | 16.0% by weight |
| 2-H2HB(F)-F | | 10.0% by weight |
| 3-H2HB(F)-F | | 5.0% by weight |
| 5-H2HB(F)-F | | 3.0% by weight |
| 2-HBB(F)-F | | 6.0% by weight |
| 3-HBB(F)-F | | 6.0% by weight |
| 5-HBB(F)-F | | 13.0% by weight |

Composition Example 24

| | | |
|---|---|---|
| V-HHVHB(F)-F | (Compound No. 44) | 7.0% by weight |
| 7-HB(F,F)-F | | 3.0% by weight |
| 3-HB-O2 | | 7.0% by weight |
| 2-HHB(F)-F | | 10.0% by weight |

-continued

| | |
|---|---|
| 3-HHB(F)-F | 10.0% by weight |
| 5-HHB(F)-F | 10.0% by weight |
| 2-HBB(F)-F | 9.0% by weight |
| 3-HBB(F)-F | 9.0% by weight |
| 5-HBB(F)-F | 16.0% by weight |
| 2-HBB-F | 4.0% by weight |
| 3-HBB(F,F)-F | 5.0% by weight |
| 5-HBB(F,F)-F | 10.0% by weight |

Composition Example 25

| | | |
|---|---|---|
| V-HVHBB-4 | (Compound No. 1) | 4.0% by weight |
| V-HHVHB(F)-F | (Compound No. 44) | 3.0% by weight |
| 3-HHB(F,F)-F | | 9.0% by weight |
| 3-H2HB(F,F)-F | | 8.0% by weight |
| 4-H2HB(F,F)-F | | 8.0% by weight |
| 5-H2HB(F,F)-F | | 8.0% by weight |
| 3-HBB(F,F)-F | | 21.0% by weight |
| 5-HBB(F,F)-F | | 20.0% by weight |
| 3-H2BB(F,F)-F | | 10.0% by weight |
| 5-HHEBB-F | | 2.0% by weight |
| 3-HH2BB(F,F)-F | | 3.0% by weight |
| 1O1-HBBH-4 | | 4.0% by weight |

Composition Example 26

| | | |
|---|---|---|
| V-HHVHB(F)-F | (Compound No. 44) | 9.0% by weight |
| 7-HB(F,F)-F | | 3.0% by weight |
| 3-H2HB(F,F)-F | | 7.0% by weight |
| 5-H2HB(F,F)-F | | 8.0% by weight |
| 3-HHB(F,F)-F | | 10.0% by weight |
| 4-HHB(F,F)-F | | 5.0% by weight |
| 3-HH2B(F,F)-F | | 6.0% by weight |
| 3-HBB(F,F)-F | | 15.0% by weight |
| 5-HBB(F,F)-F | | 15.0% by weight |
| 3-HBEB(F,F)-F | | 2.0% by weight |
| 4-HBEB(F,F)-F | | 2.0% by weight |
| 5-HBEB(F,F)-F | | 2.0% by weight |
| 3-HHEB(F,F)-F | | 10.0% by weight |
| 4-HHEB(F,F)-F | | 3.0% by weight |
| 5-HHEB(F,F)-F | | 3.0% by weight |

The present invention will be described in more detail with reference to Examples below. In the Examples, C indicates crystal; $S_A$, smectic phase A; $S_B$, smectic phase B; $S_X$, smectic phase structure of which has not yet been defined; N, nematic phase; and Iso, isotropic phase, and unit of phase transition temperature is ° C.

EXAMPLE 1

Preparation of (E)-4-(trans-4-(2-(trans-4-vinylcyclohexyl)vinyl)cyclohexyl)-4'-butylbiphenyl (Compound expressed by the general formula (1) wherein Ra is $CH_2=CH-$, Rb is $C_4H_9-$, both $A_1$ and $A_2$ are trans-1,4-cyclohexylene group, both $A_3$ and $A_4$ are 1,4-phenylene group, $Z_1$ is $-CH=CH-$, both $Z_2$ and $Z_3$ are single bond; Compound No. 1)

[First Step]

Preparation of 4-vinylcyclohexanecarbaldehyde

To a mixture of 25.2 g (70.5 mmol) of methyltriphenylphosphonium bromide with 125 ml of tetrahydrofuran (THF) was added 7.9 g (70.5 mmol) of potassium-tert-butoxide (t-BuOK) while being kept at a temperature lower than −20° C. and stirred at the same temperature for 1 hour. Then, 50 ml of solution of 10.0 g (58.8 mmol) of methyl 4-formylcyclohexanecarboxylate in THF was added dropwise to the reaction solution while being kept at a temperature lower than −20° C. and stirred at the same temperature for 2 hours. After finishing of the reaction, 50 ml of water was added to the reaction mixture and then the product was extracted with 200 ml of toluene. The organic layer thus obtained was washed with water thrice and then dried over anhydrous magnesium sulfate. The solvent was distilled off under a reduced pressure and the residue thus obtained was subjected to silica gel column chromatography (eluent: toluene) to obtain 6.8 g of a crude methyl 4-vinylcyclohexanecarboxylate.

To a solution of 6.8 g (40.4 mmol) of the crude product described above in 30 ml of toluene was added dropwise 42 ml (42.4 mmol) of DIBAL while being kept at a temperature lower than −60° C., stirred at the same temperature for 5 hours, and then stirred at room temperature for 1 hour. Then, 50 ml of saturated aqueous ammonium chloride solution and 100 ml of 6N hydrochloric acid were added to the solution, stirred at room temperature for 1 hour, and then the product was extracted with 150 ml of toluene. The organic layer thus obtained was washed with saturated aqueous sodium chloride solution thrice and dried over anhydrous magnesium sulfate. The solvent was distilled off under a reduced pressure to obtain 5.4 g of a crude 4-vinyl-1-hydroxymethylcyclohexane.

Next, 15 ml of solution of 5.4 g of the crude 4-vinyl-1-hydroxymethylcyclohexane in dichloromethane was added dropwise to a mixture of 9.1 g (42.1 mmol) of pyridinium chlorochromate and 50 ml of dichloromethane while being cooled with ice and stirred for 12 hours. The reaction mixture was filtered, the solvent was distilled off under a reduced pressure, and the residue thus obtained was subjected to silica gel column chromatography (eluent: toluene) to obtain 2.1 g of a crude 4-vinylcyclohexane-carbaldehyde. As the result of analysis of this product by gas chromatography, it was found out to be a mixture of cis/trans=31/69.

[Second Step]

Preparation of (E)-4-(trans-4-(2-(trans-4-vinylcyclohexyl)vinyl)cyclohexyl)-4'-butylbiphenyl To 50 ml of solution of 11.6 g (18.0 mmol) of the trans-4-(4'-butylbiphenyl-4-yl) cyclohexylmethyltriphenylphosphonium bromide prepared by reacting 4-(trans-4-bromomethylcyclohexyl)-4'-butylbiphenyl with triphenylphosphine, in THF was added 2.0 g (18.0 mmol) of t-BuOK while being kept at a temperature lower than −20° C. and then stirred at the same temperature for 1 hour.

Next, 15 ml of solution of 2.1 g (15.0 mmol) of the 4-vinylcyclohexanecarbaldehyde obtained by the first step, in THF was added dropwise to the mixture while being kept at a temperature lower than −20° C. and stirred at the same temperature for 2 hours. After finishing of the reaction, 100 ml of water was added to the reaction mixture and the product was extracted with 200 ml of toluene. The organic layer thus obtained was washed with water thrice and then dried over anhydrous magnesium sulfate. The solvent was distilled off under a reduced pressure and the residue was subjected to silica gel column chromatography (eluent: toluene) to obtain 3.8 g of a crude 4-(trans-4-(2-(4-vinylcyclohexyl)vinyl)cyclohexyl)-4'-butylbiphenyl.

A mixture prepared by adding 3.3 g (16.5 mmol) of sodium benzenesulfinate dihydrate, 2.7 ml of 6N hydrochloric acid, and 25 ml of mixed solvent of toluene/ethanol (1/1) to 3.5 g (8.3 mmol) of the crude 4-(trans-4-(2-(4-vinylcyclohexyl)vinyl)cyclohexyl)-4'-butylbiphenyl was refluxed for 95 hours. Water in an amount of 50 ml was added to the reaction mixture, and the mixture was extracted with 100 ml of toluene, washed with water thrice, and dried over anhydrous magnesium sulfate. The solvent was distilled off under a reduced pressure, and the residue was subjected to silica gel column chromatography (eluent: toluene/heptane=1/9) to obtain 2.8 g of a crude (E)-4-(trans-4-(2-(trans-4-vinylcyclohexyl)vinyl)cyclohexyl)-4'-butylbiphenyl. This product was recrystallized from a mixed solvent of ethanol/ethyl acetate to obtain 0.7 g of the subjective compound.

This compound exhibited liquid crystal phase and its transition temperatures were as follows:

C lower than 0° C., $S_X$ 241.2 N 335.5 Iso

Also, each spectrum datum well supported its structure.

Mass spectrum: 426 ($M^+$)

$^1$H-NMR (CDCl$_3$, δ (ppm) 0.94–2.75 (m, 29H), 4.82–5.09 (m, 1H), 5.34–5.42 (m, 2H), 5.62–5.98 (m, 2H), 7.21–7.54 (m, 8H)

Following compounds (No. 2 to No. 40) can be prepared according to the method of Example 1.

(No. 2)

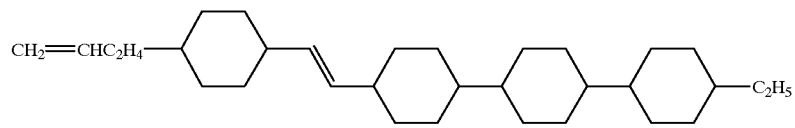

(No. 3)

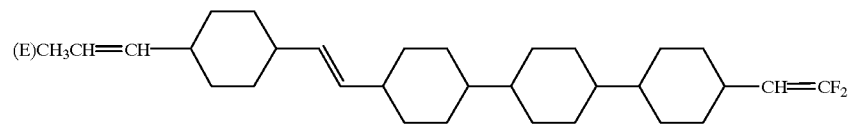

(No. 4)

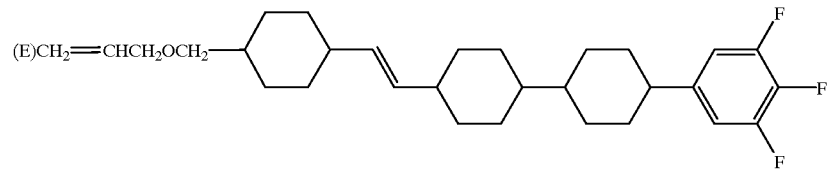

(No. 5)

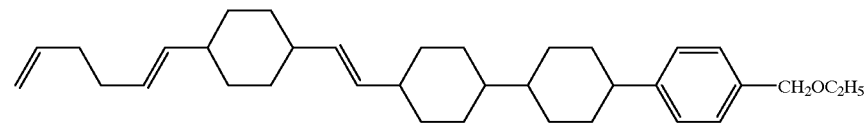

(No. 6)

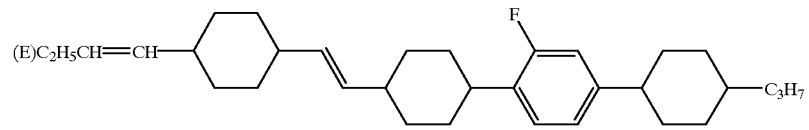

(No. 7)

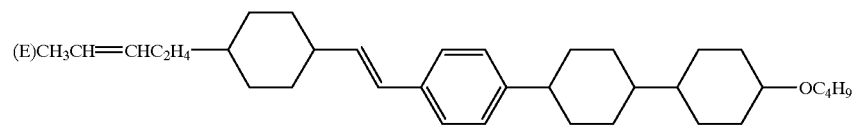

(No. 8)

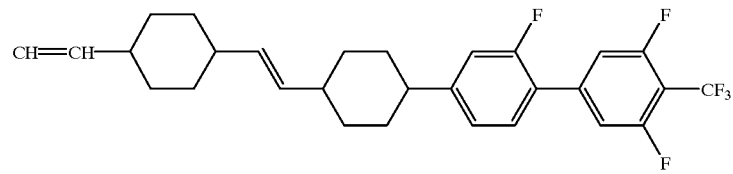

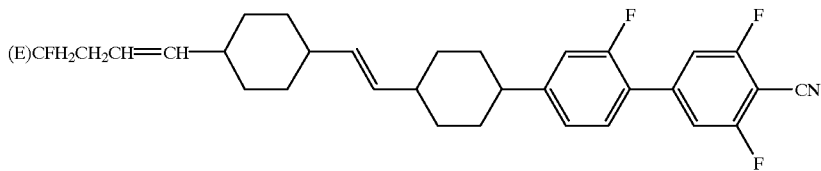
(No. 9)
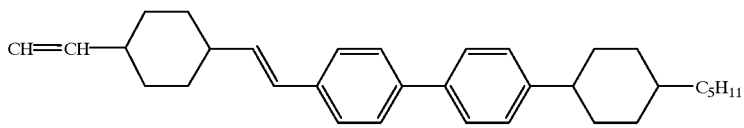
(No. 10)
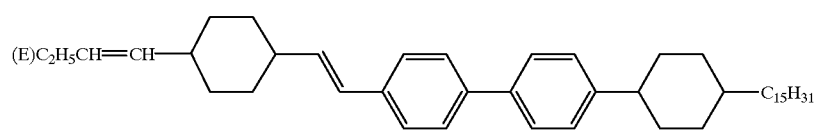
(No. 11)
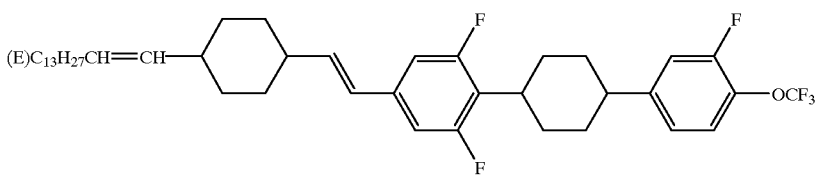
(No. 12)
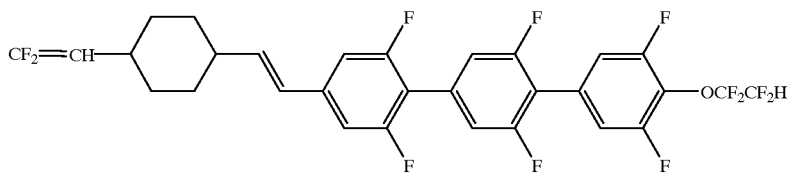
(No. 13)
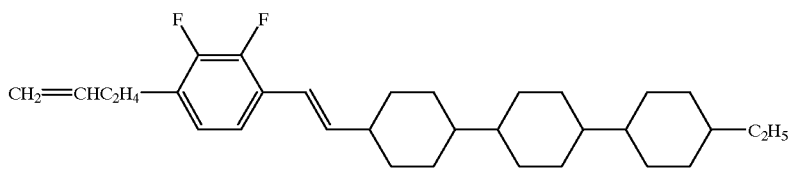
(No. 14)
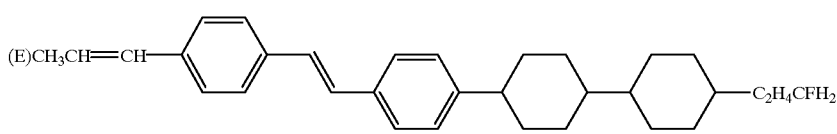
(No. 15)
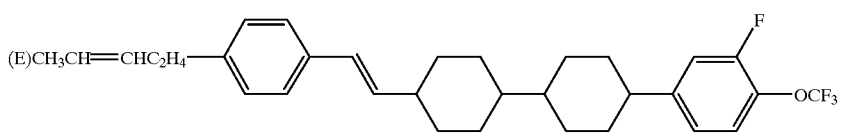
(No. 16)

-continued
(No. 17)
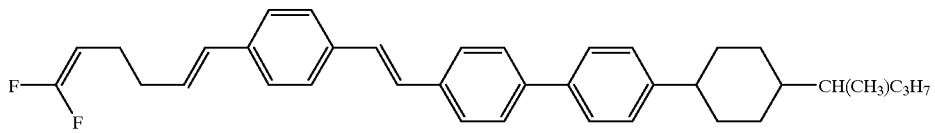
(No. 18)
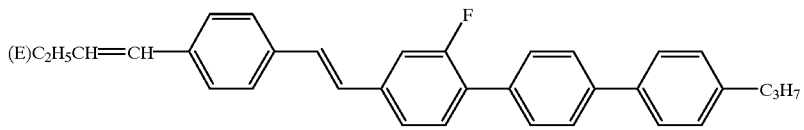
(No. 19)
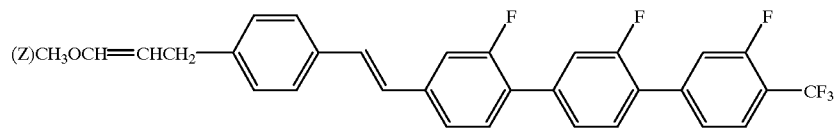
(No. 20)
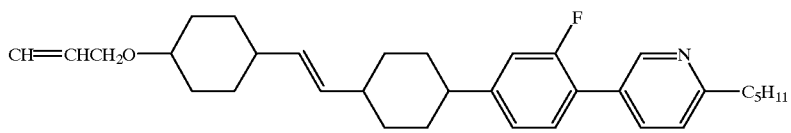
(No. 21)
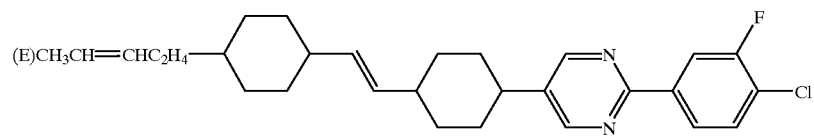
(No. 22)
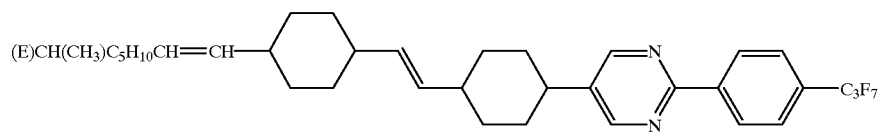
(No. 23)
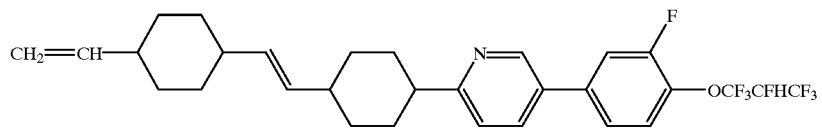
(No. 24)
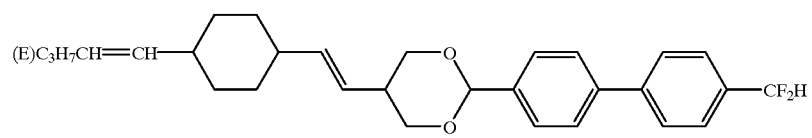
(No. 25)
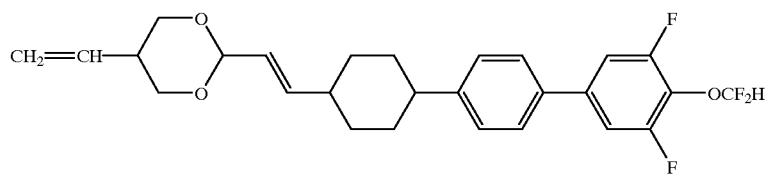

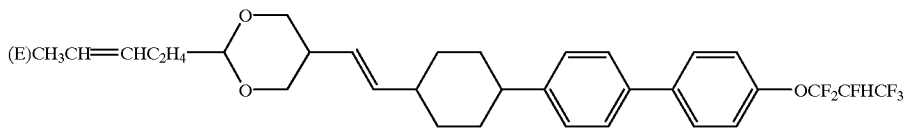
(No. 26)
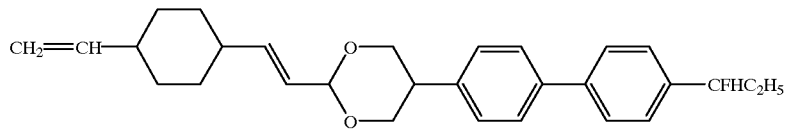
(No. 27)
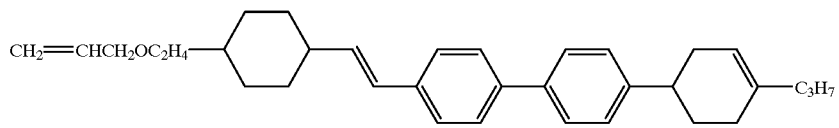
(No. 28)
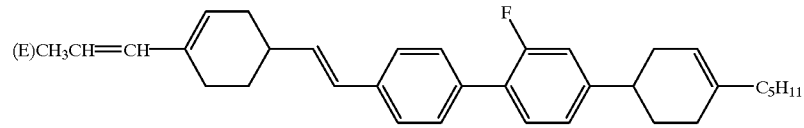
(No. 29)
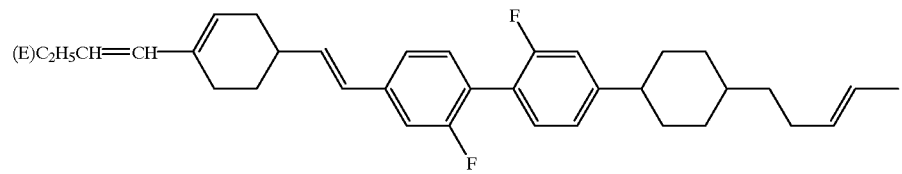
(No. 30)
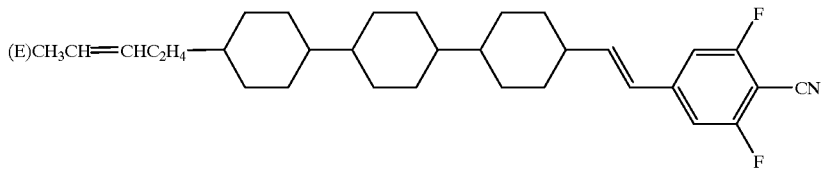
(No. 31)
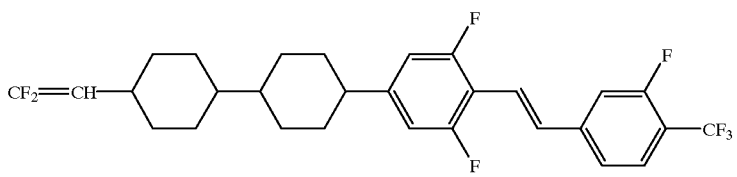
(No. 32)
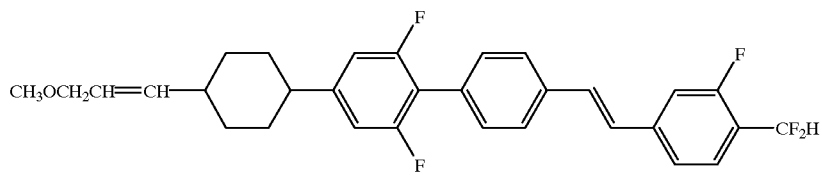
(No. 33)

(No. 34)
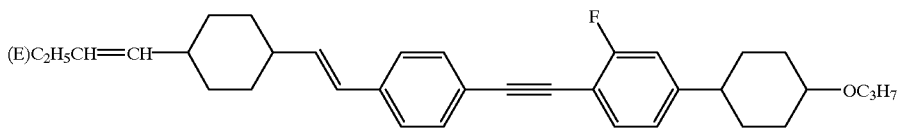

(No. 35)
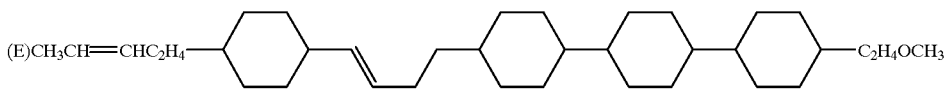

(No. 36)
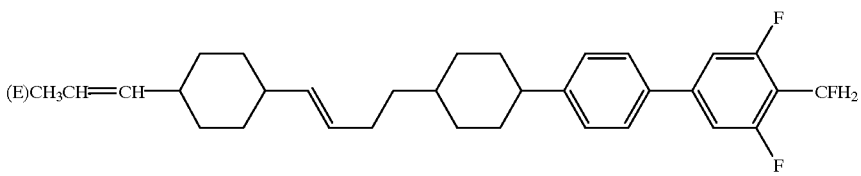

(No. 37)
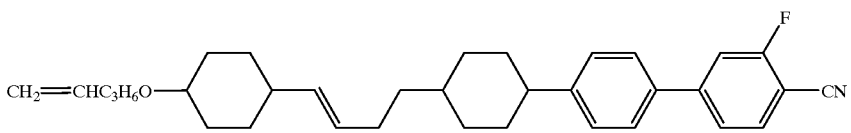

(No. 38)
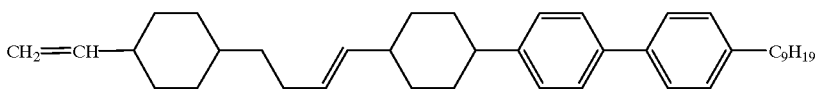

(No. 39)
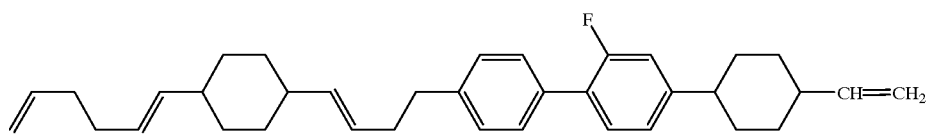

(No. 40)
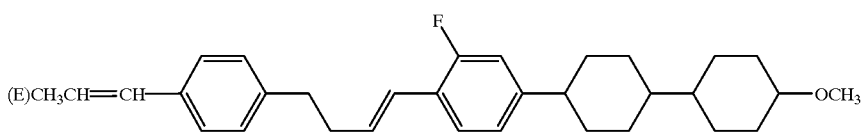

EXAMPLE 2

Preparation of (E)-4-(trans-4-(2-(trans-4-(trans-4-vinylcyclohexyl)cyclohexyl)vinyl)cyclohexyl)propylbenzene (Compound expressed by the general formula (1) wherein Ra is $CH_2=CH-$, Rb is $C_3H_7-$, $A_1$, $A_2$, and $A_3$ are trans-1,4-cyclohexylene group, $Z_2$ is $-CH=CH-$, and both $Z_1$ and $Z_3$ are single bond; Compound No. 41)

To 80 ml of solution of 15.1 g (25.0 mmol) of 4-(4-propylphenyl)cyclohexylmethyltriphenylphosphonium iodide prepared by reacting (4-iodomethylcyclohexyl)-4-propylbenzene with triphenylphosphine, in THF was added 2.6 g (23.3 mmol) of t-BuOK while being kept at a temperature lower than −20° C. and stirred at the same temperature for 1 hour.

Next, to this mixture was added dropwise 30 ml of solution of 3.0 g (13.4 mmol) of the 4-(4-vinylcyclohexyl)cyclohexanecarbaldehyde obtained by a method similar to the method of the first step in Example 1 (that is, subjected to the Wittig reaction, reduction, and then oxidation reaction using methyl 4-(4-formylcyclohexyl)cyclohexanecarboxylate instead of methyl 4-formylcyclohexanecarboxylate), in THF while being kept at a temperature lower than −20° C. and stirred at the same temperature for 2 hours.

After finishing of the reaction, 100 ml of water was added to the reaction mixture and extracted with 200 ml of toluene. The organic layer thus obtained was washed with water thrice and dried over anhydrous magnesium sulfate. The solvent was distilled off under a reduced pressure and the residue was subjected to silica gel column chromatography (eluent: toluene) to obtain 6.1 g of a crude 4-(trans-4-(2-(trans-4-(trans-4-vinylcyclohexyl)cyclohexyl)vinyl)cyclohexyl)propylbenzene.

A mixture prepared by adding 5.9 g (29.5 mmol) of sodium benzenesulfinate dihydrate, 5 ml of 6N hydrochloric acid, and 40 ml of mixed solvent of toluene/ethanol (1/1) to 6.1 g (14.5 mmol) of the crude 4-(trans-4-(2-(trans-4-(trans-4-vinylcyclohexyl)cyclohexyl)vinyl)cyclohexyl)propylbenzene was refluxed for 40 hours. Water in an amount of 30 ml was added to the reaction mixture, extracted with 150 ml of toluene, washed with water thrice, and then dried over anhydrous magnesium sulfate. The solvent was distilled off under a reduced pressure and the residue was subjected to silica gel column chromatography (eluent: heptane/toluene=95/5) to obtain 3.8 g of a crude (E)-4-(trans-4-(2-(trans-4-(trans-4-vinylcyclohexyl)cyclohexyl)-vinyl)cyclohexyl)propylbenzene. This product was recrystallized from a mixed solvent of ethanol/ethyl acetate to obtain 1.1 g of the subjective compound.

This compound exhibited liquid crystal phase and its transition temperatures were as follows:

C lower than 0° C. SB 242.8 N 310.1 Iso

Also, each spectrum datum well supported its structure.

Mass spectrum: 418 (M$^+$)

$^1$H-NMR (CDCl$_3$, δ (ppm) 0.85–2.63 (m, 37H), 4.82–5.03 (m, 2H), 5.33–5.35 (m, 2H), 5.59–5.78 (m, 1H), 7.10 (s, 4H)

Following compounds (No. 42 to No. 75) can be prepared according to the method of Example 2.

(No. 42)
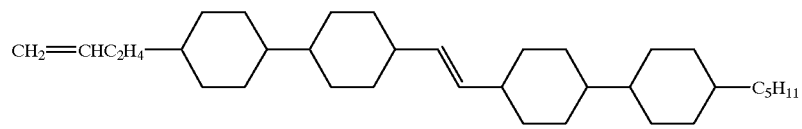

(No. 43)
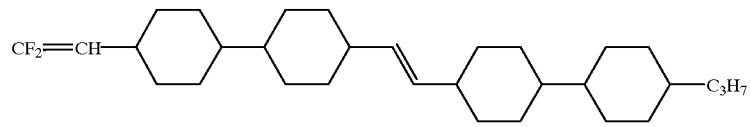

(No. 44)
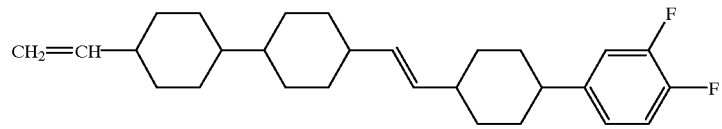

(No. 45)
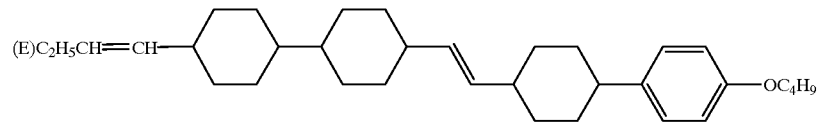

(No. 46)
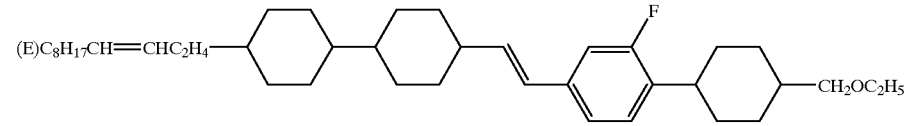

(No. 47)
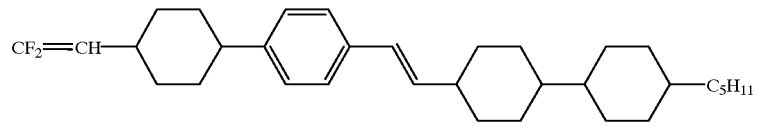

(No. 48)
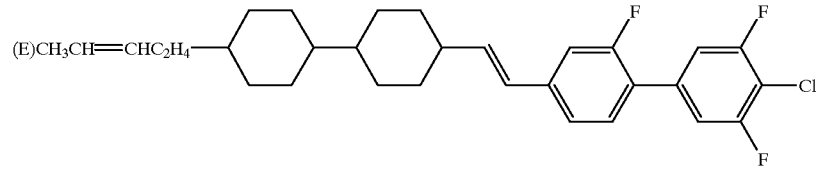

-continued
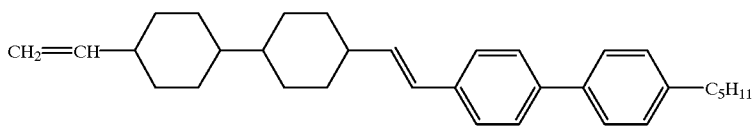
(No. 49)
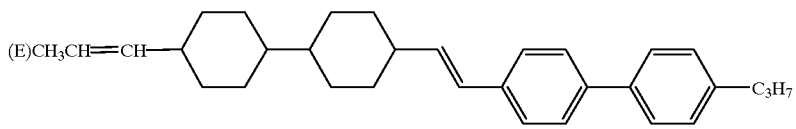
(No. 50)
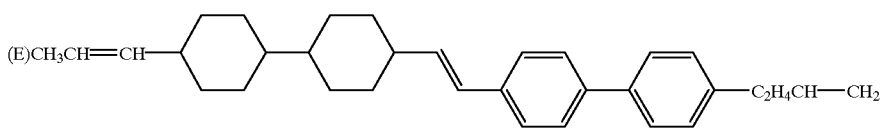
(No. 51)
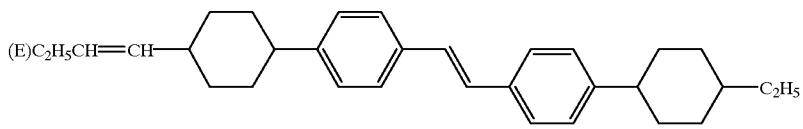
(No. 52)
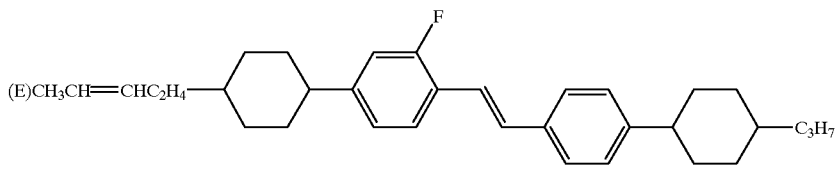
(No. 53)
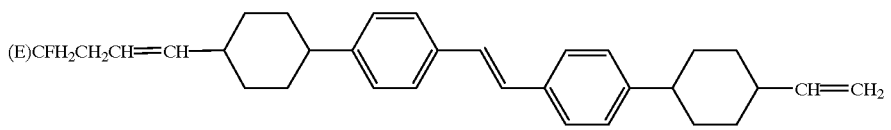
(No. 54)
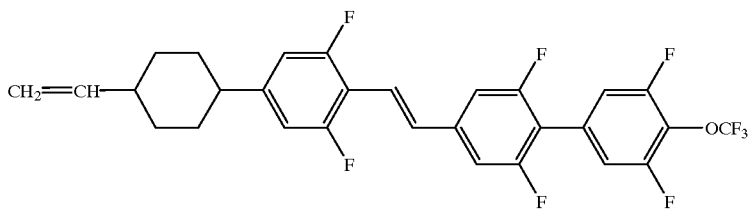
(No. 55)
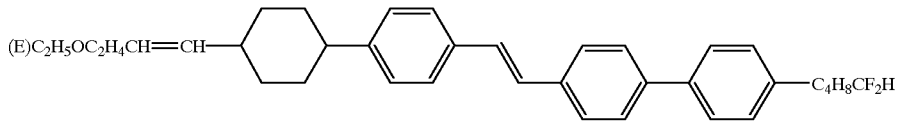
(No. 56)
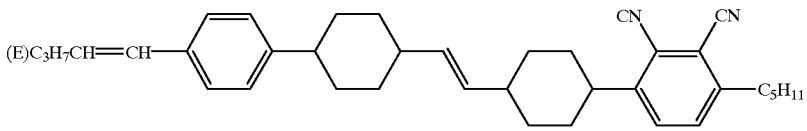
(No. 57)

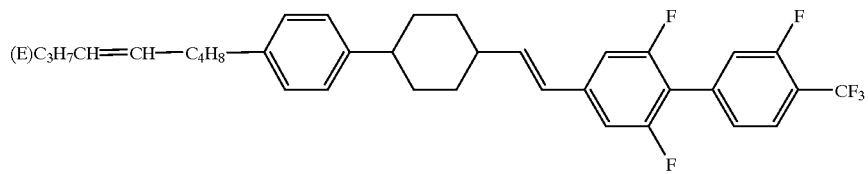
(No. 58)
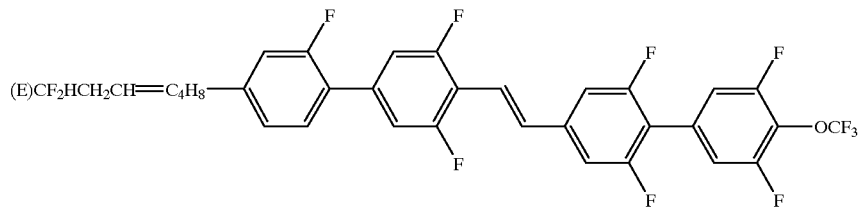
(No. 59)
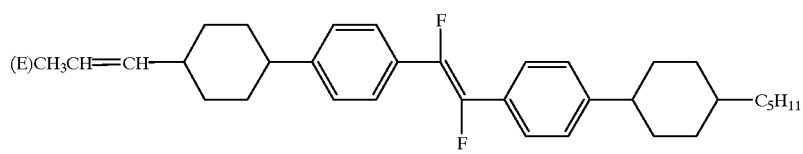
(No. 60)
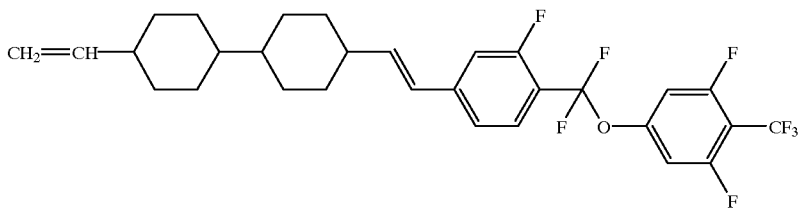
(No. 61)
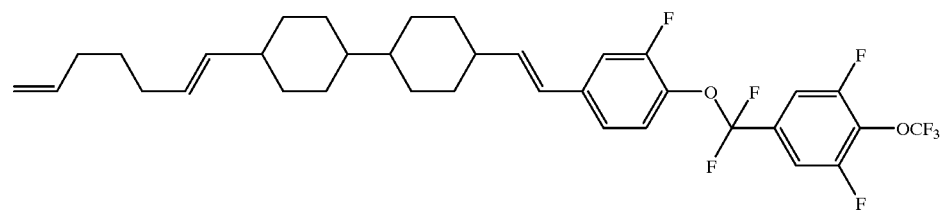
(No. 62)
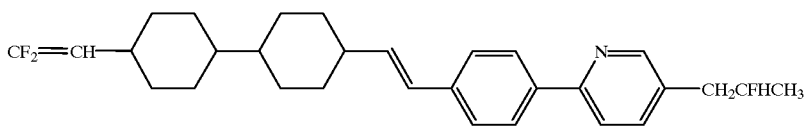
(No. 63)
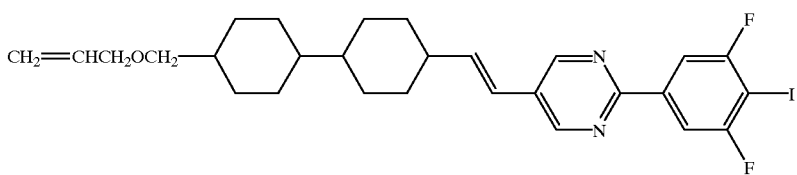
(No. 64)

(No. 65)
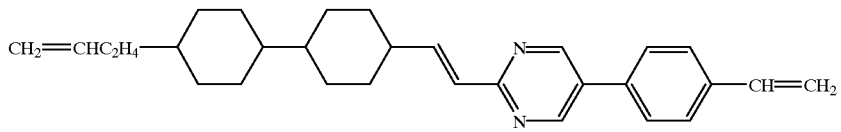
(No. 66)
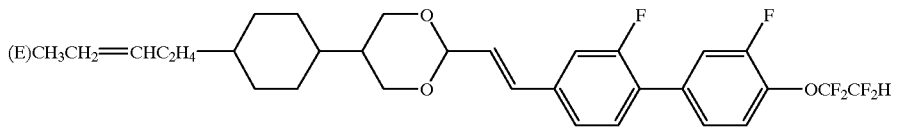
(No. 67)
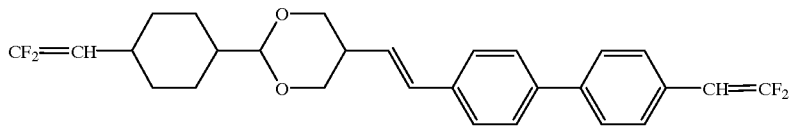
(No. 68)
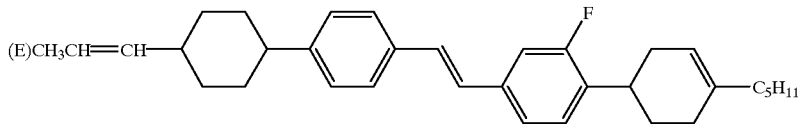
(No. 69)
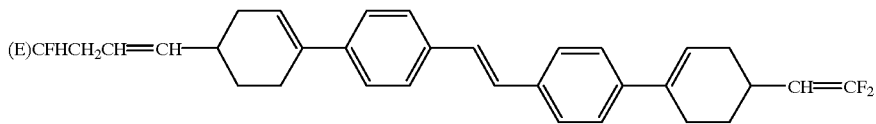
(No. 70)
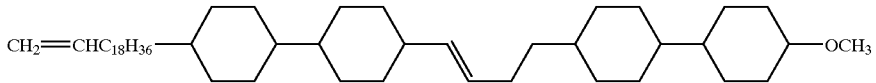
(No. 71)
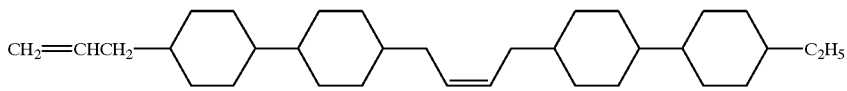
(No. 72)
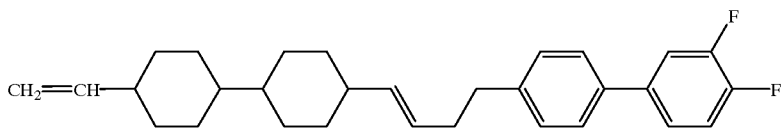
(No. 73)
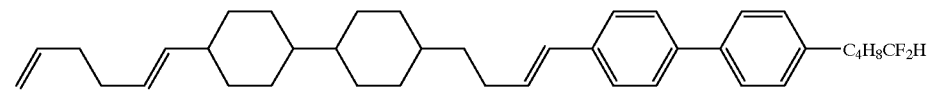
(No. 74)
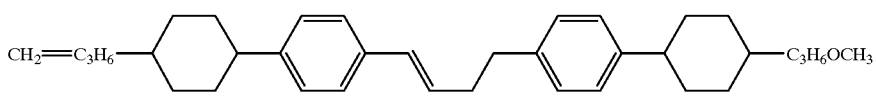

-continued

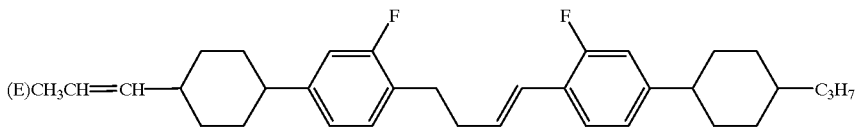

(No. 75)

Examples in which the compounds of the present invention were used as component of liquid crystal compositions are shown below. In each Use Examples, NI indicates transition temperature (° C.) of nematic phase-isotropic phase; Δε, dielectric anisotropy value; Δn, optical anisotropy value; η, viscosity at 20° C. (mpa·s); and $V_{10}$, threshold voltage (V).

EXAMPLE 3

(Use Example 1)

Liquid crystal composition (A) consisting of the following cyanophenylcyclohexane type liquid crystalline compounds in the amount shown below 4-(trans-4-propylcyclohexyl)benzonitrile 24% by weight 4-(trans-4-pentylcyclohexyl)benzonitrile 36% by weight 4-(trans-4-heptylcyclohexyl)benzonitrile 25% by weight 4-(trans-4-pentylcyclohexyl)-4'-cyanobiphenyl 15% by weight had the following physical properties:

NI: 71.7, Δε: 11.0, Δn: 0.137, η: 26.7, $V_{10}$: 1.78 (at a cell thickness of 9 μm)

Value of physical properties of liquid crystal composition (B) consisting of 85% by weight of the liquid crystal composition (A) described above and 15% by weight of the (E)-4-butyl-4'-(trans-4-(2-(trans-4-vinylcyclohexyl)vinyl)-cyclohexyl) biphenyl (Compound No. 1) obtained in Example 1 were as follows:

NI: 97.9, Δε: 10.0, Δn: 0.144, η: 30.1, $V_{10}$ at a cell thickness of 8.9 μm: 1.97

While this liquid crystal composition (B) was left in a freezer at −20° C., development of smectic phase or separation of crystals was not observed even more than 60 days.

Comparative Example 1

Value of physical properties of liquid crystal composition (C) consisting of 85% by weight of the liquid crystal composition (A) described above and 15% by weight of a known compound 4-(trans-4-propylcyclohexyl)-4'-(trans-4-pentylcyclohexyl) biphenyl described in Japanese Patent Publication No. Sho 62-46527 were as follows:

NI: 100.2, Δε: 9.5, Δn: 0.143, η: 31.8, $V_{10}$: 2.02 (at a cell thickness of 8.7 μm)

From this fact, it was found out that the compounds of the present invention are excellent both in viscosity and threshold voltage compared with known compounds of similar structure.

Comparative Example 2

Value of physical properties of liquid crystal composition (D) comprising 95% by weight of the liquid crystal composition (A) described above and 5% by weight of a known 4-ethyl-4"-(trans-4-pentylcyclohexyl) terphenyl described in Japanese Patent Publication No. Hei 2-1811 were as follows:

NI: 81.2, Δε: 9.8, Δn: 0.144, η: 31.4, $V_{10}$ at a cell thickness of 8.7 μm: 1.78

This compound was able to dissolve only 5% in liquid crystal composition (A) at room temperature. From this fact, it was found out that the compounds of the present invention are excellent both in mutual solubility and viscosity compared with known compounds of similar structure.

The compounds used in Example 1, Comparative Example 1, or Comparative Example 2 each described above had phase transition temperatures as follows:

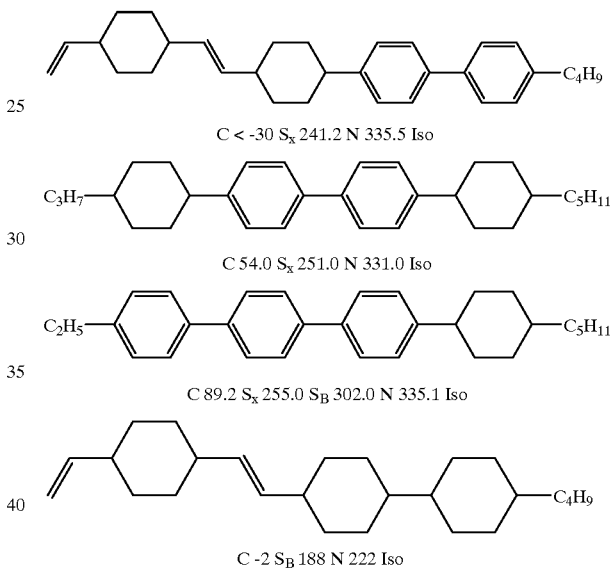

From this fact, it can be seen that the compounds of the present invention have a wider temperature range of liquid crystal phase by about 110 to 140° C. compared with known compounds and that nematic phase of the compounds of the present invention is wider by more than 30° C. in particular.

EXAMPLE 4

(Use Example 2)

Value of physical properties of the liquid crystal composition of Composition Example 16 were as follows:

NI: 101.2, Δε: 7.2, Δn: 0.164, η: 15.5, $V_{10}$: 2.15

While this liquid crystal composition was left in a freezer at −20° C., development of smectic phase or separation of crystals was not observed even more than 60 days.

Liquid crystal composition prepared by dissolving 0.8 part by weight of an optically active compound CM-33 in 100 parts by weight of the liquid crystal composition of this example had a pitch of 10.7 μm.

EXAMPLE 5

(Use Example 3)

Value of physical properties of the liquid crystal composition of Composition Example 17 were as follows:

NI: 97.9, Δε: 31.2, Δn: 0.152, η: 88.4, $V_{10}$: 0.91

While this liquid crystal composition was left in a freezer at −20° C., development of smectic phase or separation of crystals was not observed even more than 60 days.

EXAMPLE 6

(Use Example 4)

Value of physical properties of the liquid crystal composition of Composition Example 18 were as follows:

NI: 96.0, Δε: 6.6, Δn: 0.203, η: 34.7, $V_{10}$: 2.28

While this liquid crystal composition was left in a freezer at −20° C., development of smectic phase or separation of crystals was not observed even more than 60 days.

EXAMPLE 7

(Use Example 5)

Value of physical properties of the liquid crystal composition of Composition Example 19 were as follows:

NI: 86.5, Δε: 8.2, Δn: 0.143, η: 19.0, $V_{10}$: 1.79

While this liquid crystal composition was left in a freezer at −20° C., development of smectic phase or separation of crystals was not observed even more than 60 days.

EXAMPLE 8

(Use Example 6)

Value of physical properties of the liquid crystal composition of Composition Example 20 were as follows:

NI: 78.8, Δε: 23.3, Δn: 0.119, η: 36.2, $V_{10}$: 0.98

While this liquid crystal composition was left in a freezer at −20° C., development of smectic phase or separation of crystals was not observed even more than 60 days.

EXAMPLE 9

(Use Example 7)

Value of physical properties of the liquid crystal composition of Composition Example 21 were as follows:

NI: 92.7, Δε: 30.6, Δn: 0.127, η: 46.3, $V_{10}$: 0.92

While this liquid crystal composition was left in a freezer at −20° C., development of smectic phase or separation of crystals was not observed even more than 60 days.

EXAMPLE 10

(Use Example 8)

Value of physical properties of the liquid crystal composition of Composition Example 22 were as follows:

NI: 68.7, Δε: 6.6, Δn: 0.154, η: 19.1, $V_{10}$: 1.80

While this liquid crystal composition was left in a freezer at −20° C., development of smectic phase or separation of crystals was not observed even more than 60 days.

EXAMPLE 11

(Use Example 9)

Value of physical properties of the liquid crystal composition of Composition Example 23 were as follows:

NI: 108.2, Δε: 5.2, Δn: 0.094, η: 27.0, $V_{10}$: 2.24

While this liquid crystal composition was left in a freezer at −20° C., development of smectic phase or separation of crystals was not observed even more than 60 days.

Liquid crystal composition prepared by dissolving 0.3 part by weight of an optically active compound CN in 100 parts by weight of the liquid crystal composition of this example had a pitch of 77 μm.

EXAMPLE 12

(Use Example 10)

Value of physical properties of the liquid crystal composition of Composition Example 24 were as follows:

NI: 88.9, Δε: 6.2, Δn: 0.111, η: 26.1, $V_{10}$: 1.95

While this liquid crystal composition was left in a freezer at −20° C., development of smectic phase or separation of crystals was not observed even more than 60 days.

EXAMPLE 13

(Use Example 11)

Value of physical properties of the liquid crystal composition of Composition Example 25 were as follows:

NI: 99.2, Δε: 8.8, Δn: 0.114, η: 34.1, $V_{10}$: 1.79

While this liquid crystal composition was left in a freezer at −20° C., development of smectic phase or separation of crystals was not observed even more than 60 days.

EXAMPLE 14

(Use Example 12)

Value of physical properties of the liquid crystal composition of Composition Example 26 were as follows:

NI: 85.5, Δε: 11.1, Δn: 0.093, η: 32.8, $V_{10}$: 1.74

While this liquid crystal composition was left in a freezer at −20° C., development of smectic phase or separation of crystals was not observed even more than 60 days.

INDUSTRIAL APPLICABILITY

Liquid crystalline compounds of the present invention are wide in temperature range of liquid crystal phase, low in viscosity, and improved in miscibility with other liquid crystal materials. Also, novel liquid crystalline compounds having desired physical properties can be provided by selecting proper six-membered ring, substituent and/or bonding group for molecule constituting element.

Accordingly, novel liquid crystal compositions which have such a characteristic that they have a wide temperature range of liquid crystal phase, are low in viscosity, and are excellent in stability and miscibility with other liquid crystal materials, and additionally which meet other required physical properties can be provided by using the compounds of the present invention as component of liquid crystal compositions; and excellent liquid crystal display devices using the liquid crystal composition therein can be provided.

What is claimed is:

1. A liquid crystalline compound expressed by the general formula (1)

$$Ra-A_1-Z_1-A_2-Z_2-A_3-Z_3-A_4-Rb \quad (1)$$

wherein Ra represents an alkenyl group having 2 to 20 carbon atoms or an alkyl group having 1 to 20 carbon atoms, any methylene group (—$CH_2$—) in the alkenyl or alkyl group may be replaced by —O—, —S—, —CO—, —CH=CH—, or —C≡C—, but in no case are adjacent methylene groups replaced by —O— and/or —S—, and any hydrogen atom in Ra may be replaced by a halogen atom; Rb represents Ra, a halogen atom, or cyano group provided that at least one of Ra and Rb represents a group having double bond; $A_1$, $A_2$, $A_3$, and $A_4$ independently represent trans-1,4-cyclohexylene group, 1,4-phenylene group in which any hydrogen atom on the ring may be replaced by fluorine atom or cyano group, cyclohexenediyl group, pyridine-2,5-diyl group, pyrimidine-2,5-diyl group, or 1,3-dioxane-2,5-diyl group; $Z_1$, $Z_2$, and $Z_3$ independently represent an alkenylene group having 2 to 4 carbon atoms, —(CH$_2$)$_2$—, —COO—, —OCO—, —C≡C—, —CH$_2$O—, —OCH$_2$—, or single bond, any hydrogen atom in the groups may be replaced by a halogen atom, provided that at least one of $Z_1$, $Z_2$, $Z_3$ represents an alkenylene group having 2 to 4 carbon atoms, none of rings $A_1$ to $A_4$ adjacent to the alkenylene group is 1,4-phenylene group, and when all of rings $A_1$, $A_2$, and $A_3$, or all of rings $A_2$, $A_3$, and $A_4$ are trans-1,4-cyclohexylene group, then $Z_2$ is not an alkenylene group.

2. The liquid crystalline compound according to claim 1 wherein Ra is an alkenyl group.

3. The liquid crystalline compound according to claim 2 wherein $Z_1$ is an alkenylene group having 2 to 4 carbon atoms.

4. The liquid crystalline compound according to claim 2 wherein $Z_2$ is an alkenylene group having 2 to 4 carbon atoms.

5. The liquid crystalline compound according to claim 2 wherein $Z_3$ is an alkenylene group having 2 to 4 carbon atoms.

6. The liquid crystalline compound according to claim 3 wherein $A_1$, $A_2$, $A_3$, and $A_4$ are independently trans-1,4-cyclohexylene group, or 1,4-phenylene group in which any hydrogen atom on the ring may be replaced by fluorine atom or cyano group.

7. The liquid crystalline compound according to claim 4 wherein $A_1$, $A_2$, $A_3$, and $A_4$ are independently trans-1,4-cyclohexylene group, or 1,4-phenylene group in which any hydrogen atom on the ring may be replaced by fluorine atom or cyano group.

8. The liquid crystalline compound according to claim 5 wherein $A_1$, $A_2$, $A_3$, and $A_4$ are independently trans-1,4-cyclohexylene group, or 1,4-phenylene group in which any hydrogen atom on the ring may be replaced by fluorine atom or cyano group.

9. A liquid crystal composition comprising at least one liquid crystalline compound defined in any one of claims 1 to 8.

10. A liquid crystal composition comprising, as a first component, at least one liquid crystalline compound defined in any one of claims 1 to 8, and as a second component, at least one compound selected from the group consisting of the compounds expressed by any one of the general formulas (2), (3), and (4)

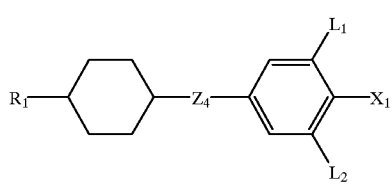

(2)

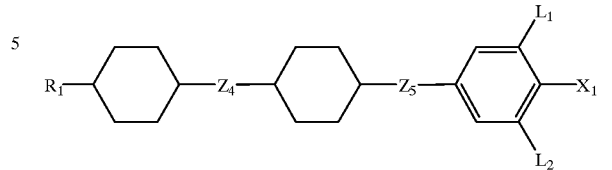

(3)

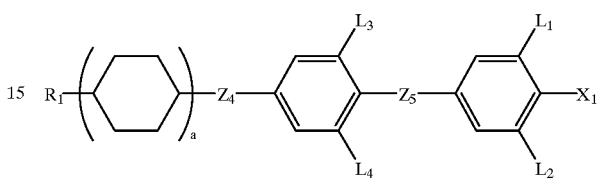

(4)

wherein $R_1$ represents an alkyl group having 1 to 10 carbon atoms; $X_1$ represents F, Cl, OCF$_3$, OCF$_2$H, CF$_3$, CF$_2$H, or CFH$_2$; $L_1$, $L_2$, $L_3$, and $L_4$ independently represent H or F; $Z_4$ and $Z_5$ independently represent —(CH$_2$)$_2$—, —CH=CH—, or single bond; and a is 1 or 2.

11. A liquid crystal composition comprising, as a first component, at least one liquid crystalline compound defined in any one of claims 1 to 8, and as a second component, at least one compound selected from the group consisting of the compounds expressed by any one of the general formulas (5), (6), (7), (8), and (9),

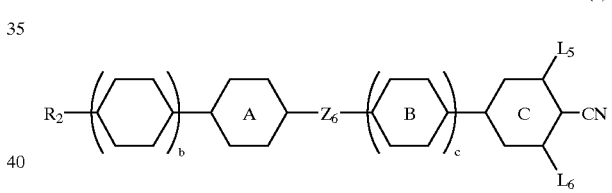

(5)

wherein $R_2$ represents F, an alkyl group having 1 to 10 carbon atoms, or an alkenyl group having 2 to 10 carbon atoms, any methylene group (—CH$_2$—) in the groups may be replaced by oxygen atom, but in no case are two or more methylene groups continuously replaced by oxygen atom; ring A represents trans-1,4-cyclohexylene group, 1,4-phenylene group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —(CH$_2$)$_2$—, —COO—, or single bond; $L_5$ and $L_6$ independently represent H or F; and b and c are independently 0 or 1,

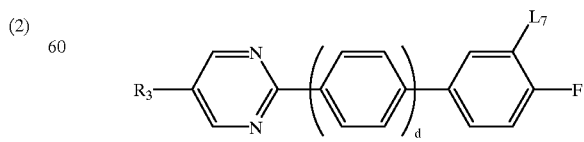

(6)

wherein $R_3$ represents an alkyl group having 1 to 10 carbon atom; $L_7$ represents H or F; and d is 0 or 1, (7)

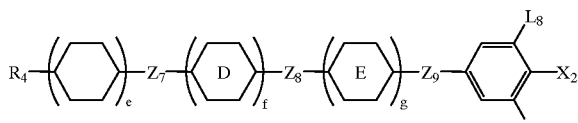

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or single bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$; and e, f, and g are independently 0 or 1, (8)

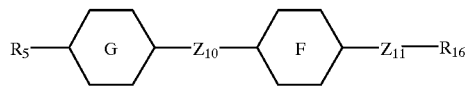

wherein $R_5$ and $R_6$ independently represent an alkyl group having 1 to 10 carbon atoms or an alkenyl group having 2 to 10 carbon atoms, any methylene group (—$CH_2$—) in the alkyl or alkenyl group may be replaced by oxygen atom (—O—), but in no case are two or more methylene groups continuously replaced by oxygen atom; ring G represents trans-1,4-cyclohexylene group, 1,4-phenylene group, or pyrimidine-2,5-diyl group; ring F represents trans-1,4-cyclohexylene group or 1,4-phenylene group; $Z_{10}$ represents —C≡C—, —COO—, —($CH_2$)$_2$—, —CH=CH—C≡C—, or single bond; and $Z_{11}$ represents —COO— or single bond, (9)

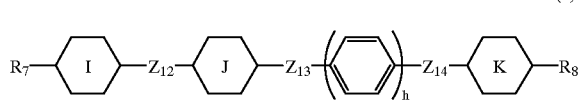

wherein $R_7$ and $R_8$ independently represent an alkyl group having 1 to 10 carbon atoms or an alkenyl group having 2 to 10 carbon atoms, any methylene group (—$CH_2$—) in the alkyl or alkenyl group may be replaced by oxygen atom (—O—), but in no case are two or more methylene groups continuously replaced by oxygen atom; ring I represents trans-1,4-cyclohexylene group, 1,4-phenylene group, or pyrimidine-2,5-diyl group; ring J represents trans-1,4-cyclohexylene group, 1,4-phenylene group in which any hydrogen atom or the ring may be replaced by F, or pyrimidine-2,5-diyl group; ring K represents trans-1,4-cyclohexylene group or 1,4-phenylene group; $Z_{12}$ and $Z_{14}$ independently represent —COO—, —($CH_{22}$—, or single bond; $Z_{13}$ represents —CH=CH—, —C≡C—, —COO—, or single bond; and h is 0 or 1.

12. A liquid crystal display device comprising a liquid crystal composition defined in claim 9.

13. A liquid crystal composition comprising, as a first component, at least one liquid crystalline compound defined in any one of claims 1 to 8, as a part of a second component, at least one compound selected from the group consisting of the compounds expressed by any one of the general formulas (2), (3), and (4)

(2)

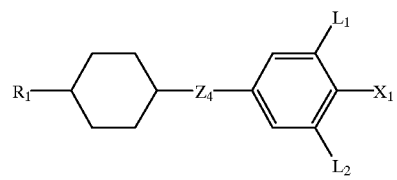

(3)

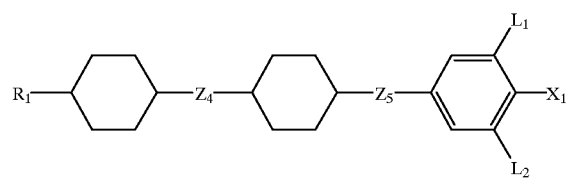

(4)

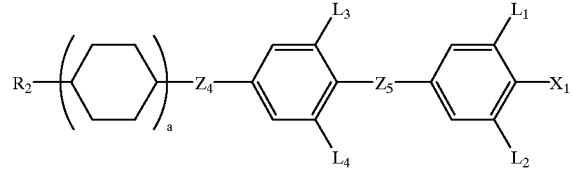

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$, and $L_4$ independently represent H or F; $Z_4$ and $Z_5$ independently represent —($CH_2$)$_2$—, —CH=CH—, or single bond; and a is 1 or 2, and as another part of the second component, at least one compound selected from the group consisting of the compounds expressed by any one of the general formulas (5), (6), (7), (8), and (9)

(5)

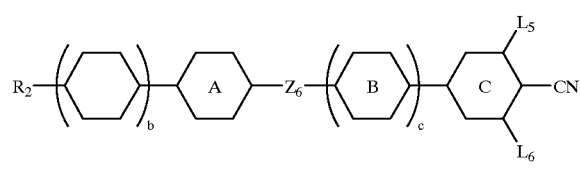

wherein $R_2$ represents F, an alkyl group having 1 to 10 carbon atoms, or an alkenyl group having 2 to 10 carbon atoms, any methylene group (—$CH_2$—) in the groups may be replaced by oxygen atom, but in no case are two or more methylene groups continuously replaced by oxygen atom; ring A represents trans-1,4-cyclohexylene group, 1,4-phenylene group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —($CH_2$)$_2$—, —COO—, or single bond; $L_5$ and $L_6$ independently represent H or F; and b and c are independently 0 or 1, (6)

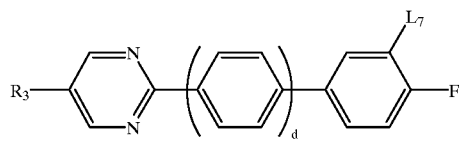

wherein R₃ represents an alkyl group having 1 to 10 carbon atom; L₇ represents H or F; and d is 0 or 1, (7)

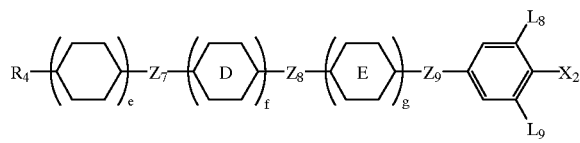

wherein R₄ represents an alkyl group having 1 to 10 carbon atoms; ring D and ring E independently represent trans-1,4-cyclohexylene group or 1,4-phenylene group; Z₇ and Z₈ independently represent —COO— or single bond; Z₉ represents —COO— or —C≡C—; L₈ and L₉ independently represent H or F; X₂ represents F, OCF₃, OCF₂H, CF₃, CF₂H, or CFH₂; and e, f, and g are independently 0 or 1, (8)

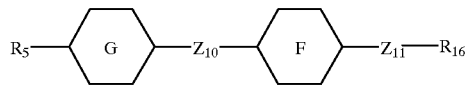

wherein R₅ and R₆ independently represent an alkyl group having 1 to 10 carbon atoms or an alkenyl group having 2 to 10 carbon atoms, any methylene group (—CH₂—) in the alkyl or alkenyl group may be replaced by oxygen atom (—O—), but in no care are two or more methylene groups continuously replaced by oxygen atom; ring G represents trans-1,4-cyclohexylene group, 1,4-phenylene group, or pyrimidine-2,5-diyl group; ring F represents trans-1,4-cyclohexylene group or 1,4-phenylene group; Z₁₀ represents —C≡C—, —COO—, —(CH₂)₂—, —CH=CH—C≡C—, or single bond; and Z₁₁ represents —COO— or single bond, (9)

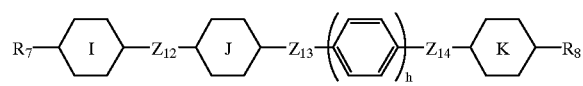

wherein R₇ and R₈ independently represent an alkyl group having 1 to 10 carbon atoms or an alkenyl group having 2 to 10 carbon atoms, any methylene group (—CH₂—) in the alkyl or alkenyl group may be replaced by oxygen atom (—O—), but in no case are two or more methylene groups continuously replaced by oxygen atom; ring I represents trans-1,4-cyclohexylene group, 1,4-phenylene group, or pyrimidine-2,5-diyl group; ring J represents trans-1,4-cyclohexylene group, 1,4-phenylene group in which any hydrogen atom on the ring may be replaced by F, or pyrimidine-2,5-diyl group; ring K represents trans-1,4-cyclohexylene group or 1,4-phenylene group; Z₁₂ and Z₁₄ independently represent —COO—, —(CH₂)₂—, or single bond; Z₁₃ represents —CH=CH—, —C≡C—, —COO—, or single bond; and h is 0 or 1.

14. A liquid crystal display device comprising a liquid crystal composition defined in claim 10.

15. A liquid crystal display device comprising a liquid crystal composition defined in claim 11.

16. A liquid crystal display device comprising a liquid crystal composition defined in claim 13.

* * * * *